US011628169B2

(12) United States Patent
Kurita et al.

(10) Patent No.: US 11,628,169 B2
(45) Date of Patent: Apr. 18, 2023

(54) THERAPEUTIC DRUG FOR MOTOR COMPLICATIONS IN PARKINSON'S DISEASE

(71) Applicant: Sumitomo Pharma Co., Ltd., Osaka (JP)

(72) Inventors: Mitsumasa Kurita, Osaka (JP); Yuki Ikeda, Osaka (JP); Mitsuhiro Nakato, Osaka (JP)

(73) Assignee: SUMITOMO PHARMA CO., LTD., Osaka (JP)

( * ) Notice: Subject to any disclaimer, the term of this patent is extended or adjusted under 35 U.S.C. 154(b) by 0 days.

(21) Appl. No.: 17/461,024

(22) Filed: Aug. 30, 2021

(65) Prior Publication Data
US 2022/0062282 A1 Mar. 3, 2022

(30) Foreign Application Priority Data
Aug. 31, 2020 (JP) .............................. JP2020-145967

(51) Int. Cl.
*A61K 31/506* (2006.01)
*A61P 25/16* (2006.01)
(52) U.S. Cl.
CPC ............ *A61K 31/506* (2013.01); *A61P 25/16* (2018.01)
(58) Field of Classification Search
CPC ............................... A61K 31/506; A61P 25/16
See application file for complete search history.

(56) References Cited

U.S. PATENT DOCUMENTS

| 4,507,303 | A | | 3/1985 | Ishizumi | |
|---|---|---|---|---|---|
| 5,817,331 | A | * | 10/1998 | Kenealy | A61K 31/506 514/252.19 |
| 10,758,535 | B1 | | 9/2020 | Kurita | |
| 2006/0110434 | A1 | | 5/2006 | Yamaguchi | |
| 2006/0193900 | A1 | | 8/2006 | Yasukochi | |
| 2007/0232629 | A1 | | 10/2007 | Yamaguchi | |
| 2014/0243350 | A1 | | 8/2014 | Hansen | |
| 2021/0060015 | A1 | | 3/2021 | Kurita | |
| 2022/0193075 | A1 | | 6/2022 | Kurita et al. | |

FOREIGN PATENT DOCUMENTS

| EP | 1743645 | 1/2007 |
|---|---|---|
| JP | 11-228414 | 2/1998 |
| WO | WO2008044336 | 2/2010 |
| WO | WO2013156035 | 10/2013 |
| WO | WO2020127954 | 6/2020 |
| WO | WO2021166987 | 8/2021 |

OTHER PUBLICATIONS

Jankovic et al. J. Neurol. Neurosurg. Psychiatry., 2020, vol. 0, pp. 1-14.*
Hikiji et al., "A case of tandospirone citrate responsive Parkinson's disease with psychotic symptoms and diurnal fluctuation," Japanese Journal of Psychiatric Treatment, 14(11):1271-1274 (1999) (Abstract Translation).
Iderberg et al., "Activity of serotonin 5-HT(1A) receptor 'biased agonists' in rat models of Parkinson's disease and L-DOPA-induced dyskinesia.," Neuropharmacology, 93:52-67 (2015).
Ishibashi et al., "Antiparkinsonian actions of a selective 5-HT1A agonist, tandospirone, in rats," Advances in Neuroregulation and Neuroprotection; 369-378 (2005).
Ishibashi et al., "Antiparkinsonian actions of a selective 5-HT1A agonist, tandospirone, in rats," Biogenic Amines 18(3-6):329-338 (2004).
Ishibashi et al., "Effect of a selective 5-HT1A agonist tandospirone on abnormal involuntary movements in rat L-DOPA-induced dyskinesia model," Journal of Pharmacological Sciences, 101:110 (2006).
Kannari et al., "Tandospirone citrate, a selective 5-HT1A agonist, alleviates L-DOPA-induced dyskinesia in patients with Parkinson's disease," Brain Nerve 54(2):133-137 (2002) (Abstract Translation).
Kitanaka et al., "Decreased striatal dopamine level accompanied by the increase in the duration of the stereotypy after treatment with 2-phenylethylamine in combination with 1-deprenyl in mice," Journal of Pharmacological Sciences, 100:192 (2006).
Matsubara et al., "Tandospirone, a 5-HT1A agonist, ameliorates movement disorder via non-dopaminergic systems in rats with unilateral 6-hydroxydopamine-generated lesions," Brain Research 1112(1):126-133 (2006).
Nomoto et al., "A 5-HT1A receptor agonist, tandospirone improves gait disturbance of patients with Parksinson's disease," The Journal of Movement Disorder and Disability 7(2):65-70 (1997) (Abstract Translation).

(Continued)

*Primary Examiner* — Samira J Jean-Louis
(74) *Attorney, Agent, or Firm* — Haley Guiliano LLP; James F. Haley, Jr.; Brian M. Gummow

(57) ABSTRACT

The present disclosure provides a therapeutic drug that is useful for the treatment of motor fluctuations (e.g., wearing-off) in Parkinson's disease. In particular, the present disclosure provides a composition and method for treating, improving, suppressing the progression, or preventing motor complications in Parkinson's disease, especially motor fluctuation, comprising tandospirone or a pharmaceutically acceptable salt thereof, wherein the tandospirone or a pharmaceutically acceptable salt thereof is parenterally administered.

24 Claims, 26 Drawing Sheets

(56) References Cited

OTHER PUBLICATIONS

Yoshino et al., "Tandospirone potentiates the fluoxetine-induced increases in extracellular dopamine via 5-HT(1A) receptors in the rat medial frontal cortex," Neurochemistry International, 40(4):355-360 (2002).
Huang et al., "Role of tandospirone, a 5-HT1A receptor partial agonist, in the treatment of central nervous system disorders and underlying mechanisms," Oncotarget 8(60):102705-102270 (2017).
Kannari et al., "Tandospirone citrate, a selective 5-HT1A agonist, alleviates L-DOPA-induced dyskinesia in patients with Parkinson's disease," Brain Nerve 54(2):133-137 (2002) (with English Translation of complete document).
Nomoto et al., "A 5-HT1A receptor agonist, tandospirone improves gait disturbance of patients with Parksinson's disease," The Journal of Movement Disorder and Disability 7(2):65-70 (1997) (with English Translation of complete document).

* cited by examiner

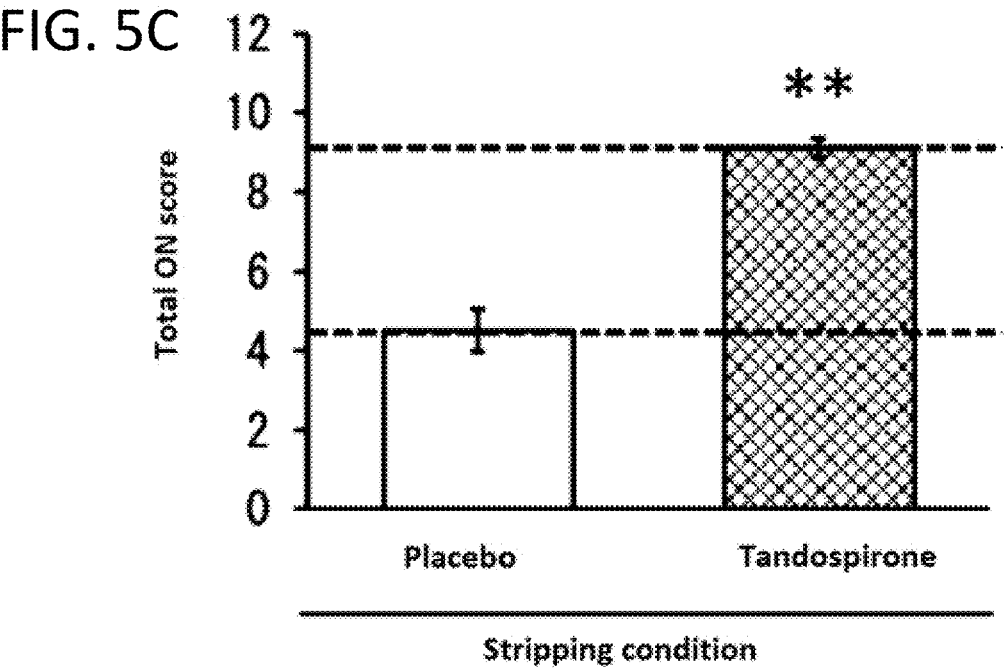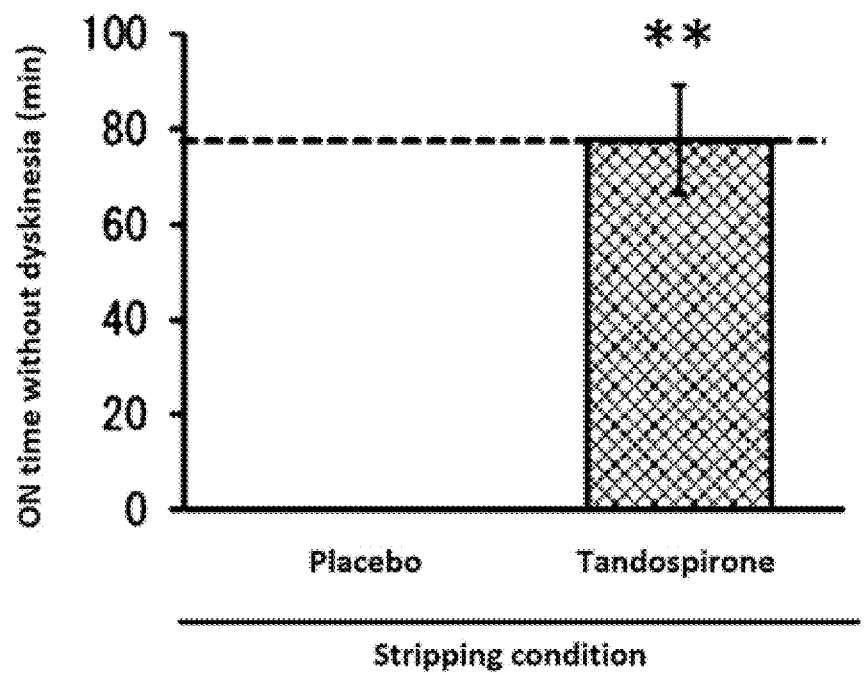

THERAPEUTIC DRUG FOR MOTOR COMPLICATIONS IN PARKINSON'S DISEASE

CROSS REFERENCE TO RELATED APPLICATIONS

This application claims priority pursuant to 35 U.S.C. § 119 to Japanese Patent Application No. 2020-145967, filed Aug. 31, 2020. Japanese Patent Application No. 2020-145967 is incorporated by reference herein in its entirety.

TECHNICAL FIELD

The present disclosure relates to a formulation for treating or preventing motor complications such as motor fluctuations in Parkinson's disease by parenteral administration (e.g., transdermal administration), comprising tandospirone or a pharmaceutically acceptable salt or prodrug thereof that is useful as a medicament as an active ingredient, or a method of treating the same.

BACKGROUND ART

Parkinson's disease is a progressive neurodegenerative disease with a primary symptom of extrapyramidal function abnormality. Pathologically, loss of dopaminergic neurons and alpha-synuclein deposition in the substantia nigra pars compacta are observed. Clinically, various motor symptoms such as akinesia, tremor, rigidity, and loss of postural reflexes are exhibited.

Parkinson's disease therapy is fundamentally a drug therapy intended to supplement intracerebral dopamine. A drug comprising levodopa (L-dopa), which is a dopamine precursor, is used as the first-line drug for the initial therapy of Parkinson's disease. However, motor complications such as motor fluctuations in parkinsonian symptoms, Parkinson's disease levodopa induced dyskinesia (hereinafter, also referred to as "PD-LID"), and dystonia are manifested in almost all patients undergoing levodopa therapy with the progression in pathological conditions.

Known representative symptoms of motor fluctuations include wearing-off, on-off phenomenon, no-on phenomenon, delayed on phenomenon, and the like. In particular, wearing-off is a symptom in which a deterioration in the ability to retain dopamine in the synaptic cleft due to progression in pathological conditions, as described above, leads to a change in the intracerebral dopamine concentration in accordance with the blood levodopa concentration, resulting in a reduction in the period of retaining the effect of levodopa with the blood concentration below the safe therapeutic range.

The frequency of developing PD-LID in 5 years after the initial levodopa therapy is 30 to 50%. The frequency increases with the progression of the pathological condition and reaches 50 to 100% in 10 years after the initial therapy. Peak-dose dyskinesia is known as an exemplary symptom of PD-LID, which is an involuntary movement manifested in the face, tongue, neck, limbs, body trunk, or the like when the blood levodopa concentration is high.

Patent Literature 1 has a disclosure on transdermally absorbed tandospirone agents.

CITATION LIST

Patent Literature

[Patent Literature 1] Japanese Laid-Open Publication No. 11-228414

SUMMARY OF INVENTION

Solution to Problem

As a result of diligent studies, the inventors have discovered that tandospirone or a pharmaceutically acceptable salt thereof possesses both an action of suppressing a rapid increase in the dopamine level in the striatum synaptic cleft under various circumstances such as upon administration of levodopa in Parkinson's disease and an action of delaying a decrease thereof over time. The inventors have also discovered that a preferred technology for the treatment, improvement, suppression of progression (delay or suppression), or prevention of motor complications in levodopa therapy for Parkinson's disease can be provided. The inventors further discovered that a useful technology for treatment, improvement, suppression of progression, or prevention with a high effect of improving motor complications found in Parkinson's disease can be provided, as compared to oral administration, by parenterally administering (e.g., transdermal administration, intradermal administration, subcutaneous administration, intramuscular administration, or the like). Examples of targets of improvement in such motor complications include motor fluctuations such as wearing-off, on-off phenomenon, no-on phenomenon, and delayed on phenomenon, dyskinesia in Parkinson's disease such as levodopa induced dyskinesia (PD-LID), and the like.

The present disclosure primarily provides explanations associated with levodopa therapy, but it is understood that the present disclosure is similarly applied to instances due to other causes.

It is also critical to control non-motor symptoms in therapy of Parkinson's disease or the like. The composition of the present disclosure also has an advantage of having no adverse effect on non-motor symptoms in the treatment of motor complications such as improvement of dyskinesia in comparison to other therapeutic drugs (e.g., extended release amantadine formulation or the like) for motor symptoms in Parkinson's disease. Depending on the patient, an improvement in non-motor symptoms can also be expected in addition to an effect of improving motor complications such as improving dyskinesia and motor fluctuations.

Examples of the non-motor symptoms include psychiatric symptoms, sleep disorders, sensory disturbance, pain, olfactory dysfunction, autonomic nervous system symptoms, and the like. Examples of psychiatric symptoms include depression, anxiety, apathy, excitation, irascibility, hallucination, delusion, cognitive dysfunction, and the like. Examples of sleep disorders include daytime hypersomnia, insomnia, restless legs syndrome, REM sleep behavior disorder, and the like. Examples of autonomic nervous system symptoms include constipation, dysuria, orthostatic hypotension, and the like.

The composition of the present disclosure is expected not to exacerbate especially depression, anxiety, irascibility, restless legs syndrome, REM sleep behavior disorder, or hallucination, and is expected to have an effect of improving depression, anxiety, irascibility, restless legs syndrome, or REM sleep behavior disorder in comparison to other therapeutic drugs (e.g., extended release amantadine formulation or the like) for motor symptoms in Parkinson's disease.

Specifically, the present disclosure comprises the following.

[Item H1]

A composition for treating, improving, or preventing motor complications, comprising tandospirone or a pharmaceutically acceptable salt thereof, wherein the tandospirone or a pharmaceutically acceptable salt thereof is parenterally administered.

[Item H1B]

A composition for treating, improving, or preventing dyskinesia, comprising tandospirone or a pharmaceutically acceptable salt thereof, wherein the tandospirone or a pharmaceutically acceptable salt thereof is parenterally administered.

[Item H1C]

A composition for treating, improving, or preventing dyskinesia in a subject, comprising tandospirone or a pharmaceutically acceptable salt thereof, wherein the tandospirone or a pharmaceutically acceptable salt thereof is parenterally administered, and the subject is undergoing drug therapy for Parkinson's disease.

[Item H1D]

A composition for treating, improving, or preventing dyskinesia in a subject, comprising tandospirone or a pharmaceutically acceptable salt thereof, wherein the tandospirone or a pharmaceutically acceptable salt thereof is parenterally administered, and the subject is undergoing levodopa therapy.

[Item H1E-1]

A composition for reducing OFF time in a subject who is a Parkinson's disease patient, comprising tandospirone or a pharmaceutically acceptable salt thereof, wherein the tandospirone or a pharmaceutically acceptable salt thereof is parenterally administered, and the subject is undergoing drug therapy.

[Item H1E] A composition for reducing OFF time in a subject who is a Parkinson's disease patient, comprising tandospirone or a pharmaceutically acceptable salt thereof, wherein the tandospirone or a pharmaceutically acceptable salt thereof is parenterally administered, and the subject is undergoing drug therapy.

[Item H1F]

A composition for reducing OFF time and increasing ON time in a subject who is a Parkinson's disease patient, comprising tandospirone or a pharmaceutically acceptable salt thereof, wherein the tandospirone or a pharmaceutically acceptable salt thereof is parenterally administered, and the subject is undergoing drug therapy.

[Item H1G]

A composition for reducing a non-response time (OFF time) and increasing ON time without troublesome dyskinesia in a Parkinson's disease patient, comprising tandospirone or a pharmaceutically acceptable salt thereof, wherein the tandospirone or a pharmaceutically acceptable salt thereof is parenterally administered, and the subject is undergoing drug therapy.

[Item H1H]

A composition for reducing a non-response time (OFF time) and increasing an antiparkinsonian action effective time (ON time) without troublesome dyskinesia in a Parkinson's disease patient, comprising tandospirone or a pharmaceutically acceptable salt thereof, wherein the tandospirone or a pharmaceutically acceptable salt thereof is parenterally administered, and the subject is undergoing levodopa therapy.

[Item H2]

A composition for treating, improving, or preventing motor complications in Parkinson's disease, comprising tandospirone or a pharmaceutically acceptable salt thereof, wherein the tandospirone or a pharmaceutically acceptable salt thereof is parenterally administered.

[Item H3]

A composition for treating, improving, or preventing motor complications in Parkinson's disease, comprising tandospirone or a pharmaceutically acceptable salt thereof, wherein the tandospirone or a pharmaceutically acceptable salt thereof is parenterally administered, and the subject is undergoing drug therapy for Parkinson's disease.

[Item H4]

A composition for treating, improving, or preventing motor complications in Parkinson's disease, comprising tandospirone or a pharmaceutically acceptable salt thereof, wherein the tandospirone or a pharmaceutically acceptable salt thereof is parenterally administered, and the subject is undergoing drug therapy selected from the group consisting of drug therapy for Parkinson's disease using a levodopa containing formulation, a levodopa metabolite inhibitor, or a dopamine receptor agonist and therapy using an adjunct agent for Parkinson's disease.

[Item H5]

A composition for treating, improving, or preventing motor complications in Parkinson's disease, comprising tandospirone or a pharmaceutically acceptable salt thereof, wherein the tandospirone or a pharmaceutically acceptable salt thereof is parenterally administered, and the subject is undergoing dopamine replacement therapy for Parkinson's disease.

[Item H6]

A composition for treating, improving, or preventing motor complications in Parkinson's disease, comprising tandospirone or a pharmaceutically acceptable salt thereof, wherein the tandospirone or a pharmaceutically acceptable salt thereof is parenterally administered, and the subject is undergoing levodopa therapy for Parkinson's disease.

[Item H7]

A composition for treating, improving, or preventing motor complications in Parkinson's disease, comprising tandospirone or a pharmaceutically acceptable salt thereof, wherein an effective amount of the tandospirone or a pharmaceutically acceptable salt thereof is parenterally administered, and wherein the composition sustainably maintains a dopamine level in a striatal synaptic cleft, suppresses a rapid change in a dopamine level, and/or suppresses intermittent dopamine receptor stimulation in a subject.

[Item H8]

The composition of any one of the preceding items, which is administered so that a rebound symptom does not manifest in the subject.

[Item H9]

The composition of any one of the preceding items, wherein the motor complications comprise motor fluctuations.

[Item H10]

The composition of any one of the preceding items, wherein the parenteral administration is selected from transdermal administration, intradermal administration, subcutaneous administration, intramuscular administration, and a combination thereof.

[Item H11]

The composition of any one of the preceding items, wherein the parenteral administration has sustainability or is sustainably administered.

[Item H12]

The composition of any one of the preceding items, wherein the parenteral administration comprises transdermal administration.

[Item H13]

The composition of any one of the preceding items, wherein the treatment, improvement, or prevention improves motor complications without exacerbating a dyskinesia symptom in Parkinson's disease.

[Item H14]

The composition of any one of the preceding items, wherein the treatment, improvement, or prevention improves motor complications without exacerbating a levodopa induced dyskinesia (PD-LID) symptom.

[Item H15]

The composition of any one of the preceding items, wherein the treatment, improvement, or prevention improves motor fluctuations without exacerbating a dyskinesia symptom in Parkinson's disease.

[Item H16]

The composition of any one of the preceding items, wherein the treatment, improvement, or prevention improves motor fluctuations without exacerbating a levodopa induced dyskinesia (PD-LID) symptom.

[Item H17]

The composition of any one of the preceding items, wherein the treatment, improvement, or prevention improves motor complications or motor fluctuations without exacerbating a dyskinesia symptom in Parkinson's disease.

[Item H18]

The composition of any one of the preceding items, wherein the treatment, improvement, or prevention improves motor complications or motor fluctuations without a rebound symptom of a levodopa induced dyskinesia (PD-LID).

[Item H19]

The composition of any one of the preceding items, wherein the motor fluctuations comprise a wearing-off phenomenon, an on-off phenomenon, a no-on phenomenon, a delayed on phenomenon, and a combination thereof.

[Item H20]

The composition of any one of the preceding items, wherein treatment, improvement, or prevention of the motor fluctuations comprises prolongation of an antiparkinsonian action effective time (ON-time), a reduction of a non-response time (OFF-time), or a combination thereof.

[Item H21]

The composition of any one of the preceding items, wherein the motor complications further comprise a dyskinesia symptom in Parkinson's disease.

[Item H22]

The composition of any one of the preceding items, wherein the motor complications further comprise levodopa induced dyskinesia (PD-LID).

[Item H23]

The composition of any one of the preceding items, wherein a dyskinesia symptom in Parkinson's disease comprises peak-dose dyskinesia, diphasic dyskinesia, and a combination thereof.

[Item H24]

The composition of any one of the preceding items, wherein levodopa induced dyskinesia (PD-LID) comprises peak-dose dyskinesia, diphasic dyskinesia, and a combination thereof.

[Item H25]

The composition of any one of the preceding items, wherein the treatment, improvement, or prevention improves motor fluctuations without a dyskinesia symptom.

[Item H26]

The composition of any one of the preceding items, wherein the treatment, improvement, or prevention improves motor fluctuations without a troublesome dyskinesia symptom.

[Item H27]

A composition for accomplishing improvement or prevention of a dyskinesia symptom in a Parkinson's disease patient, reduction of a period of dyskinesia manifestation in a Parkinson's disease patient, or a combination thereof, comprising tandospirone or a pharmaceutically acceptable salt thereof, wherein the composition does not exacerbate motor fluctuations, and the tandospirone or a pharmaceutically acceptable salt thereof is parenterally administered.

[Item H28]

The composition of any one of the preceding items for accomplishing improvement or prevention of a levodopa induced dyskinesia (PD-LID) symptom, reduction of a period of levodopa induced dyskinesia (PD-LID) manifestation, or a combination thereof.

[Item H29]

A composition for accomplishing improvement or prevention of a dyskinesia symptom in a Parkinson's disease patient, reduction of a period of dyskinesia manifestation in a Parkinson's disease patient, or a combination thereof, comprising tandospirone or a pharmaceutically acceptable salt thereof, wherein the composition does not reduce an antiparkinsonian action effective time (ON-time) associated with levodopa therapy for Parkinson's disease by a clinically significant period or longer, and/or does not prolong a non-response time (OFF-time) to a clinically significant period or longer, and wherein the tandospirone or a pharmaceutically acceptable salt thereof is parenterally administered.

[Item H30]

The composition of any one of the preceding items for accomplishing improvement or prevention of a levodopa induced dyskinesia (PD-LID) symptom, reduction of a period of levodopa induced dyskinesia (PD-LID) manifestation, or a combination thereof, wherein the composition does not reduce an antiparkinsonian action effective time (ON-time) associated with levodopa therapy for Parkinson's disease by a clinically significant period or longer, and/or does not prolong a non-response time (OFF-time) to a clinically significant period or longer.

[Item H31]

The composition of any one of the preceding items, wherein the reduction of a non-response time (OFF-time) is by a clinically significant period or longer.

[Item H32]

The composition of any one of the preceding items, wherein the reduction of a non-response time (OFF-time) is by a sufficient period to attain clinical effect.

[Item H33]

A composition for accomplishing prolongation of an antiparkinsonian action effective time (ON-time) in Parkinson's disease, reduction of a non-response time (OFF-time), improvement or prevention of a dyskinesia symptom, reduction of a period of dyskinesia manifestation, or a combination thereof, comprising tandospirone or a pharmaceutically acceptable salt thereof, wherein the tandospirone or a pharmaceutically acceptable salt thereof is parenterally administered.

[Item H34]

A composition for accomplishing prolongation of an antiparkinsonian action effective time (ON-time) associated with levodopa therapy for Parkinson's disease, reduction of a non-response time (OFF-time), improvement or prevention of a levodopa induced dyskinesia (PD-LID) symptom, reduction of a period of levodopa induced dyskinesia (PD-LID) manifestation, or a combination thereof, comprising tandospirone or a pharmaceutically acceptable salt thereof, wherein the tandospirone or a pharmaceutically acceptable salt thereof is parenterally administered.

[Item H35]

The composition of any one of the preceding items, wherein improvement of the motor fluctuations is a clinically significant improvement or greater.

[Item H36]

The composition of any one of the preceding items, wherein improvement of the motor fluctuations is to a sufficient level to attain a clinical effect.

[Item H37]

The composition of any one of the preceding items, which is a transdermally administered formulation.

[Item H38]

The composition of any one of the preceding items, which is provided as an adhesive formulation.

[Item H39]

The composition of any one of the preceding items, wherein the transdermally administered formulation is a tape/patch.

[Item H40]

The composition of any one of the preceding items, wherein a drug dosage of the tandospirone or a pharmaceutically acceptable salt thereof is 0.1 to 500 mg per day as a free form of tandospirone.

[Item H41]

The composition of any one of the preceding items, wherein a drug dosage of the tandospirone or a pharmaceutically acceptable salt thereof is 3 to 250 mg per day as a free form of tandospirone.

[Item H42]

The composition of any one of the preceding items, wherein an amount of drug penetration for the tandospirone or a pharmaceutically acceptable salt thereof is 0.1 to 100 mg per day as a free form of tandospirone.

[Item H43]

The composition of any one of the preceding items, wherein an amount of drug penetration for the tandospirone or a pharmaceutically acceptable salt thereof is 1 to 60 mg per day as a free form of tandospirone.

[Item H44]

The composition of any one of the preceding items, wherein the tandospirone or a pharmaceutically acceptable salt thereof is provided as a transdermally administered formulation, and a total applied area per dose is 1 to 100 cm$^2$.

[Item H45]

The composition of any one of the preceding items, wherein the tandospirone or a pharmaceutically acceptable salt thereof is provided as a transdermally administered formulation, and a total applied area per dose is 9 to 60 cm$^2$.

[Item H46]

The composition of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item H47]

The composition of any one of the preceding items, wherein the tandospirone or a pharmaceutically acceptable salt thereof is administered so that a human blood (plasma) tandospirone concentration is 0.5 to 15 ng/mL for 12 hours or longer per day.

[Item H48]

The composition of any one of the preceding items, wherein the tandospirone or a pharmaceutically acceptable salt thereof is administered so that a human blood (plasma) tandospirone concentration is 0.05 to 20 ng/mL for 12 hours to 30 hours after a single administration of the tandospirone or a pharmaceutically acceptable salt thereof.

[Item H49]

The composition of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item H50]

The composition of any one of the preceding items, wherein the tandospirone or a pharmaceutically acceptable salt thereof is administered so that a human blood (plasma) tandospirone concentration is 0.1 to 15 ng/mL for 8 to 16 hours after administration of the tandospirone or a pharmaceutically acceptable salt thereof.

[Item H51]

The composition of any one of the preceding items, wherein the tandospirone or a pharmaceutically acceptable salt thereof is administered so that a human blood (plasma) tandospirone concentration is 10 to 100% of a maximum blood concentration after administration for 8 to 16 hours after administration of the tandospirone or a pharmaceutically acceptable salt thereof.

[Item H52]

The composition of any one of the preceding items, wherein the tandospirone or a pharmaceutically acceptable salt thereof is administered so that a ratio of a minimum concentration, with respect to a maximum blood concentration after administration as 100%, is 10 to 95% for a human blood (plasma) tandospirone concentration for 8 to 16 hours after administration of the tandospirone or a pharmaceutically acceptable salt thereof, and wherein the maximum blood concentration after administration is 1 to 15 ng/mL.

[Item H53]

The composition of any one of the preceding items, wherein the tandospirone or a pharmaceutically acceptable salt thereof is administered so that a ratio of a minimum concentration, with respect to a maximum blood concentration after administration as 100%, is 10 to 95% for a human blood (plasma) tandospirone concentration for 8 to 16 hours after administration of the tandospirone or a pharmaceutically acceptable salt thereof.

[Item H54]

The composition of any one of the preceding items, wherein the tandospirone or a pharmaceutically acceptable salt thereof is administered so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% after administration of the tandospirone or a pharmaceutically acceptable salt thereof.

[Item H55]

The composition of any one of the preceding items, wherein the tandospirone or a pharmaceutically acceptable salt thereof is administered so that an amount of change in striatal [$^{11}$C] raclopride receptor binding from before levodopa administration to 1 hour after administration (amount of change B/1h) after administering the tandospirone or a pharmaceutically acceptable salt thereof is less than 10%.
[Item H56]
The composition of any one of the preceding items, provided as an adjunct of levodopa.
[Item H57]
The composition of any one of the preceding items, which is used with levodopa in the same formulation or concomitantly as separate formulations.
[Item H58]
A medicament for treating or preventing Parkinson's disease without accompanying or by minimizing motor complications, comprising a combination of tandospirone or a pharmaceutically acceptable salt thereof and (1) levodopa or (2) levodopa and a metabolizing enzyme inhibitor of levodopa, wherein the tandospirone or a pharmaceutically acceptable salt thereof is parenterally administered.
[Item H59]
The medicament of any one of the preceding items, wherein the motor complications comprise motor fluctuations.
[Item H60]
The medicament of any one of the preceding items, wherein the motor complications further comprise dyskinesia.
[Item H61]
The medicament of any one of the preceding items, wherein the motor complications further comprise drug induced dyskinesia.
[Item H62]
The medicament of any one of the preceding items, wherein the motor complications further comprise levodopa induced dyskinesia (PD-LID).
[Item H63]
The medicament of any one of the preceding items, wherein the tandospirone or a pharmaceutically acceptable salt thereof and the (1) or (2) are administered simultaneously or at different times.
[Item H64]
A medicament for treating or preventing Parkinson's disease without accompanying or by minimizing motor complications, comprising (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt thereof, wherein the tandospirone or a pharmaceutically acceptable salt thereof is parenterally administered.
[Item H65]
The medicament of any one of the preceding items, wherein the motor complications comprise dyskinesia.
[Item H66]
The medicament of any one of the preceding items, wherein the motor complications comprise drug induced dyskinesia.
[Item H67]
The medicament of any one of the preceding items, wherein the motor complications comprise levodopa induced dyskinesia (PD-LID).
[Item H68]
The medicament of any one of the preceding items, wherein the tandospirone or a pharmaceutically acceptable salt thereof and the (1) or (2) are administered simultaneously or at different times.

[Item H69]
A composition for improving the exacerbation in quality of response to levodopa therapy of a Parkinson's disease patient, comprising tandospirone or a pharmaceutically acceptable salt thereof, wherein the tandospirone or a pharmaceutically acceptable salt thereof is parenterally administered.
[Item H70]
The composition of any one of the preceding items, wherein the improvement comprises an improvement of motor fluctuations.
[Item H71]
The composition of any one of the preceding items, wherein the improvement comprises an improvement of dyskinesia.
[Item H72]
The composition of any one of the preceding items, wherein the improvement comprises an improvement of drug induced dyskinesia.
[Item H73]
The composition of any one of the preceding items, wherein the improvement comprises an improvement of levodopa induced dyskinesia (PD-LID).
[Item J1]
Use for the manufacture of a medicament for treating, improving, or preventing motor complications, comprising tandospirone or a pharmaceutically acceptable salt thereof, wherein the tandospirone or a pharmaceutically acceptable salt thereof is parenterally administered.
[Item J1B]
Use for the manufacture of a medicament for treating, improving, or preventing dyskinesia, comprising tandospirone or a pharmaceutically acceptable salt thereof, wherein the tandospirone or a pharmaceutically acceptable salt thereof is parenterally administered.
[Item J1C]
Use for the manufacture of a medicament for treating, improving, or preventing dyskinesia in a subject, comprising tandospirone or a pharmaceutically acceptable salt thereof, wherein the tandospirone or a pharmaceutically acceptable salt thereof is parenterally administered, and the subject is undergoing drug therapy for Parkinson's disease.
[Item J1D]
Use for the manufacture of a medicament for treating, improving, or preventing dyskinesia in a subject, comprising tandospirone or a pharmaceutically acceptable salt thereof, wherein the tandospirone or a pharmaceutically acceptable salt thereof is parenterally administered, and the subject is undergoing levodopa therapy.
[Item J1E-1]
Use for the manufacture of a medicament for reducing OFF time in a subject who is a Parkinson's disease patient, comprising tandospirone or a pharmaceutically acceptable salt thereof, wherein the tandospirone or a pharmaceutically acceptable salt thereof is parenterally administered, and the subject is undergoing drug therapy.
[Item J1E]
Use for the manufacture of a medicament for reducing OFF time in a subject who is a Parkinson's disease patient, comprising tandospirone or a pharmaceutically acceptable salt thereof, wherein the tandospirone or a pharmaceutically acceptable salt thereof is parenterally administered, and the subject is undergoing drug therapy.
[Item J1F]
Use for the manufacture of a medicament for reducing OFF time and increasing ON time in a subject who is a Parkinson's disease patient, comprising tandospirone or a pharmaceutically acceptable salt thereof, wherein the tandospirone or a pharmaceutically acceptable salt thereof is parenterally administered, and the subject is undergoing drug therapy.

[Item J1G]

Use for the manufacture of a medicament for reducing a non-response time (OFF time) and increasing ON time without troublesome dyskinesia in a Parkinson's disease patient, comprising tandospirone or a pharmaceutically acceptable salt thereof, wherein the tandospirone or a pharmaceutically acceptable salt thereof is parenterally administered, and the subject is undergoing drug therapy.

[Item J1H]

Use for the manufacture of a medicament for reducing a non-response time (OFF time) and increasing an antiparkinsonian action effective time (ON time) without troublesome dyskinesia in a Parkinson's disease patient, comprising tandospirone or a pharmaceutically acceptable salt thereof, wherein the tandospirone or a pharmaceutically acceptable salt thereof is parenterally administered, and the subject is undergoing levodopa therapy.

[Item J2]

Use for the manufacture of a medicament for treating, improving, or preventing motor complications in Parkinson's disease, comprising tandospirone or a pharmaceutically acceptable salt thereof, wherein the tandospirone or a pharmaceutically acceptable salt thereof is parenterally administered.

[Item J3]

Use for the manufacture of a medicament for treating, improving, or preventing motor complications in Parkinson's disease, comprising tandospirone or a pharmaceutically acceptable salt thereof, wherein the tandospirone or a pharmaceutically acceptable salt thereof is parenterally administered, and the subject is undergoing drug therapy for Parkinson's disease.

[Item J4]

Use for the manufacture of a medicament for treating, improving, or preventing motor complications in Parkinson's disease, comprising tandospirone or a pharmaceutically acceptable salt thereof, wherein the tandospirone or a pharmaceutically acceptable salt thereof is parenterally administered, and the subject is undergoing drug therapy selected from the group consisting of drug therapy for Parkinson's disease using a levodopa containing formulation, a levodopa metabolite inhibitor, or a dopamine receptor agonist and therapy using an adjunct agent for Parkinson's disease.

[Item J5]

Use for the manufacture of a medicament for treating, improving, or preventing motor complications in Parkinson's disease, comprising tandospirone or a pharmaceutically acceptable salt thereof, wherein the tandospirone or a pharmaceutically acceptable salt thereof is parenterally administered, and the subject is undergoing dopamine replacement therapy for Parkinson's disease.

[Item J6]

Use for the manufacture of a medicament for treating, improving, or preventing motor complications in Parkinson's disease, comprising tandospirone or a pharmaceutically acceptable salt thereof, wherein the tandospirone or a pharmaceutically acceptable salt thereof is parenterally administered, and the subject is undergoing levodopa therapy for Parkinson's disease.

[Item J7]

Use for the manufacture of a medicament for treating, improving, or preventing motor complications in Parkinson's disease, comprising tandospirone or a pharmaceutically acceptable salt thereof, wherein an effective amount of the tandospirone or a pharmaceutically acceptable salt thereof is parenterally administered, and wherein the medicament sustainably maintains a dopamine level in a striatal synaptic cleft, suppresses a rapid change in a dopamine level, and/or suppresses intermittent dopamine receptor stimulation in a subject.

[Item J8]

The use of any one of the preceding items, wherein the medicament is administered so that a rebound symptom does not manifest in the subject.

[Item J9]

The use of any one of the preceding items, wherein the motor complications comprise motor fluctuations.

[Item J10]

The use of any one of the preceding items, wherein the parenteral administration is selected from transdermal administration, intradermal administration, subcutaneous administration, intramuscular administration, and a combination thereof.

[Item J11]

The use of any one of the preceding items, wherein the parenteral administration has sustainability or is sustainably administered.

[Item J12]

The use of any one of the preceding items, wherein the parenteral administration comprises transdermal administration.

[Item J13]

The use of any one of the preceding items, wherein the treatment, improvement, or prevention improves motor complications without exacerbating a dyskinesia symptom in Parkinson's disease.

[Item J14]

The use of any one of the preceding items, wherein the treatment, improvement, or prevention improves motor complications without exacerbating a levodopa induced dyskinesia (PD-LID) symptom.

[Item J15]

The use of any one of the preceding items, wherein the treatment, improvement, or prevention improves motor fluctuations without exacerbating a dyskinesia symptom in Parkinson's disease.

[Item J16]

The use of any one of the preceding items, wherein the treatment, improvement, or prevention improves motor fluctuations without exacerbating a levodopa induced dyskinesia (PD-LID) symptom.

[Item J17]

The use of any one of the preceding items, wherein the treatment, improvement, or prevention improves motor complications or motor fluctuations without exacerbating a dyskinesia symptom in Parkinson's disease.

[Item J18]

The use of any one of the preceding items, wherein the treatment, improvement, or prevention improves motor complications or motor fluctuations without a rebound symptom of a levodopa induced dyskinesia (PD-LID).

[Item J19]

The use of any one of the preceding items, wherein the motor fluctuations comprise a wearing-off phenomenon, an on-off phenomenon, a no-on phenomenon, a delayed on phenomenon, and a combination thereof.

[Item J20]

The use of any one of the preceding items, wherein treatment, improvement, or prevention of the motor fluctuations comprises prolongation of an antiparkinsonian action effective time (ON-time), a reduction of a non-response time (OFF-time), or a combination thereof.

[Item J21]

The use of any one of the preceding items, wherein the motor complications further comprise a dyskinesia symptom in Parkinson's disease.

[Item J22]

The use of any one of the preceding items, wherein the motor complications further comprise levodopa induced dyskinesia (PD-LID).

[Item J23]

The use of any one of the preceding items, wherein a dyskinesia symptom in Parkinson's disease comprises peak-dose dyskinesia, diphasic dyskinesia, and a combination thereof.

[Item J24]

The use of any one of the preceding items, wherein levodopa induced dyskinesia (PD-LID) comprises peak-dose dyskinesia, diphasic dyskinesia, and a combination thereof.

[Item J25]

The use of any one of the preceding items, wherein the treatment, improvement, or prevention improves motor fluctuations without a dyskinesia symptom.

[Item J26]

The use of any one of the preceding items, wherein the treatment, improvement, or prevention improves motor fluctuations without a troublesome dyskinesia symptom.

[Item J27]

Use for the manufacture of a medicament for accomplishing improvement or prevention of a dyskinesia symptom in a Parkinson's disease patient, reduction of a period of dyskinesia manifestation in a Parkinson's disease patient, or a combination thereof, comprising tandospirone or a pharmaceutically acceptable salt thereof, wherein the use does not exacerbate motor fluctuations, and the tandospirone or a pharmaceutically acceptable salt thereof is parenterally administered.

[Item J28]

The use of any one of the preceding items for accomplishing improvement or prevention of a levodopa induced dyskinesia (PD-LID) symptom, reduction of a period of levodopa induced dyskinesia (PD-LID) manifestation, or a combination thereof.

[Item J29]

Use for the manufacture of a medicament for accomplishing improvement or prevention of a dyskinesia symptom in a Parkinson's disease patient, reduction of a period of dyskinesia manifestation in a Parkinson's disease patient, or a combination thereof, comprising tandospirone or a pharmaceutically acceptable salt thereof, wherein the use does not reduce an antiparkinsonian action effective time (ON-time) associated with levodopa therapy for Parkinson's disease by a clinically significant period or longer, and/or does not prolong a non-response time (OFF-time) to a clinically significant period or longer, and wherein the tandospirone or a pharmaceutically acceptable salt thereof is parenterally administered.

[Item J30]

The use of any one of the preceding items, wherein the use is for accomplishing improvement or prevention of a levodopa induced dyskinesia (PD-LID) symptom, reduction of a period of levodopa induced dyskinesia (PD-LID) manifestation, or a combination thereof, wherein the use does not reduce an antiparkinsonian action effective time (ON-time) associated with levodopa therapy for Parkinson's disease by a clinically significant period or longer, and/or does not prolong a non-response time (OFF-time) to a clinically significant period or longer.

[Item J31]

The use of any one of the preceding items, wherein the reduction of a non-response time (OFF-time) is by a clinically significant period or longer.

[Item J32]

The use of any one of the preceding items, wherein the reduction of a non-response time (OFF-time) is by a sufficient period to attain clinical effect.

[Item J33]

Use for the manufacture of a medicament for accomplishing prolongation of an antiparkinsonian action effective time (ON-time) in Parkinson's disease, reduction of a non-response time (OFF-time), improvement or prevention of a dyskinesia symptom, reduction of a period of dyskinesia manifestation, or a combination thereof, comprising tandospirone or a pharmaceutically acceptable salt thereof, wherein the tandospirone or a pharmaceutically acceptable salt thereof is parenterally administered.

[Item J34]

Use for the manufacture of a medicament for accomplishing prolongation of an antiparkinsonian action effective time (ON-time) associated with levodopa therapy for Parkinson's disease, reduction of a non-response time (OFF-time), improvement or prevention of a levodopa induced dyskinesia (PD-LID) symptom, reduction of a period of levodopa induced dyskinesia (PD-LID) manifestation, or a combination thereof, comprising tandospirone or a pharmaceutically acceptable salt thereof, wherein the tandospirone or a pharmaceutically acceptable salt thereof is parenterally administered.

[Item J35]

The use of any one of the preceding items, wherein improvement of the motor fluctuations is a clinically significant improvement or greater.

[Item J36]

The use of any one of the preceding items, wherein improvement of the motor fluctuations is to a sufficient level to attain a clinical effect.

[Item J37]

The use of any one of the preceding items, wherein the medicament is a transdermally administered formulation.

[Item J38]

The use of any one of the preceding items, wherein the medicament is provided as an adhesive formulation.

[Item J39]

The use of any one of the preceding items, wherein the transdermally administered formulation is a tape/patch.

[Item J40]

The use of any one of the preceding items, wherein a drug dosage of the tandospirone or a pharmaceutically acceptable salt thereof is 0.1 to 500 mg per day as a free form of tandospirone.

[Item J41]

The use of any one of the preceding items, wherein a drug dosage of the tandospirone or a pharmaceutically acceptable salt thereof is 3 to 250 mg per day as a free form of tandospirone.

[Item J42]

The use of any one of the preceding items, wherein an amount of drug penetration for the tandospirone or a pharmaceutically acceptable salt thereof is 0.1 to 100 mg per day as a free form of tandospirone.

[Item J43]

The use of any one of the preceding items, wherein an amount of drug penetration for the tandospirone or a pharmaceutically acceptable salt thereof is 1 to 60 mg per day as a free form of tandospirone.

[Item J44]

The use of any one of the preceding items, wherein the tandospirone or a pharmaceutically acceptable salt thereof is provided as a transdermally administered formulation, and a total applied area per dose is 1 to 100 cm$^2$.

[Item J45]

The use of any one of the preceding items, wherein the tandospirone or a pharmaceutically acceptable salt thereof is provided as a transdermally administered formulation, and a total applied area per dose is 9 to 60 cm$^2$.

[Item J46]

The use of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item J47]

The use of any one of the preceding items, wherein the tandospirone or a pharmaceutically acceptable salt thereof is administered so that a human blood (plasma) tandospirone concentration is 0.5 to 15 ng/mL for 12 hours or longer per day.

[Item J48]

The use of any one of the preceding items, wherein the tandospirone or a pharmaceutically acceptable salt thereof is administered so that a human blood (plasma) tandospirone concentration is 0.05 to 20 ng/mL for 12 hours to 30 hours after a single administration of the tandospirone or a pharmaceutically acceptable salt thereof.

[Item J49]

The use of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item J50]

The use of any one of the preceding items, wherein the tandospirone or a pharmaceutically acceptable salt thereof is administered so that a human blood (plasma) tandospirone concentration is 0.1 to 15 ng/mL for 8 to 16 hours after administration of the tandospirone or a pharmaceutically acceptable salt thereof.

[Item J51]

The use of any one of the preceding items, wherein the tandospirone or a pharmaceutically acceptable salt thereof is administered so that a human blood (plasma) tandospirone concentration is 10 to 100% of a maximum blood concentration after administration for 8 to 16 hours after administration of the tandospirone or a pharmaceutically acceptable salt thereof.

[Item J52]

The use of any one of the preceding items, wherein the tandospirone or a pharmaceutically acceptable salt thereof is administered so that a ratio of a minimum concentration, with respect to a maximum blood concentration after administration as 100%, is 10 to 95% for a human blood (plasma) tandospirone concentration for 8 to 16 hours after administration of the tandospirone or a pharmaceutically acceptable salt thereof, and wherein the maximum blood concentration after administration is 1 to 15 ng/mL.

[Item J53]

The use of any one of the preceding items, wherein the tandospirone or a pharmaceutically acceptable salt thereof is administered so that a ratio of a minimum concentration, with respect to a maximum blood concentration after administration as 100%, is 10 to 95% for a human blood (plasma) tandospirone concentration for 8 to 16 hours after administration of the tandospirone or a pharmaceutically acceptable salt thereof.

[Item J54]

The use of any one of the preceding items, wherein the tandospirone or a pharmaceutically acceptable salt thereof is administered so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% after administration of the tandospirone or a pharmaceutically acceptable salt thereof.

[Item J55]

The use of any one of the preceding items, wherein the tandospirone or a pharmaceutically acceptable salt thereof is administered so that an amount of change in striatal [$^{11}$C] raclopride receptor binding from before levodopa administration to 1 hour after administration (amount of change B/1 h) after administering the tandospirone or a pharmaceutically acceptable salt thereof is less than 10%.

[Item J56]

The use of any one of the preceding items, wherein the medicament is provided as an adjunct of levodopa.

[Item J57]

The use of any one of the preceding items, wherein the medicament is used with levodopa in the same formulation or concomitantly as separate formulations.

[Item J58]

Use of a combination of tandospirone or a pharmaceutically acceptable salt thereof and (1) levodopa or (2) levodopa and a metabolizing enzyme inhibitor of levodopa for the manufacture of a medicament for treating or preventing Parkinson's disease without accompanying or by minimizing motor complications, wherein the tandospirone or a pharmaceutically acceptable salt thereof is parenterally administered.

[Item J59]

The use of any one of the preceding items, wherein the motor complications comprise motor fluctuations.

[Item J60]

The use of any one of the preceding items, wherein the motor complications further comprise dyskinesia.

[Item J61]

The use of any one of the preceding items, wherein the motor complications further comprise drug induced dyskinesia.

[Item J62]

The use of any one of the preceding items, wherein the motor complications further comprise levodopa induced dyskinesia (PD-LID).

[Item J63]

The use of any one of the preceding items, wherein the tandospirone or a pharmaceutically acceptable salt thereof and the (1) or (2) are administered simultaneously or at different times.

[Item J64]

Use for the manufacture of a medicament for treating or preventing Parkinson's disease without accompanying or by minimizing motor complications, wherein the medicament comprises (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt thereof, wherein the tandospirone or a pharmaceutically acceptable salt thereof is parenterally administered.

[Item J65]

The use of any one of the preceding items, wherein the motor complications comprise dyskinesia.

[Item J66]

The use of any one of the preceding items, wherein the motor complications comprise drug induced dyskinesia.

[Item J67]

The use of any one of the preceding items, wherein the motor complications comprise levodopa induced dyskinesia (PD-LID).

[Item J68]

The use of any one of the preceding items, wherein the tandospirone or a pharmaceutically acceptable salt thereof and the (1) or (2) are administered simultaneously or at different times.

[Item J69]

Use for improving the exacerbation in quality of response to levodopa therapy of a Parkinson's disease patient, comprising tandospirone or a pharmaceutically acceptable salt thereof, wherein the tandospirone or a pharmaceutically acceptable salt thereof is parenterally administered.

[Item J70]

The use of any one of the preceding items, wherein the improvement comprises an improvement of motor fluctuations.

[Item J71]

The use of any one of the preceding items, wherein the improvement comprises an improvement of dyskinesia.

[Item J72]

The use of any one of the preceding items, wherein the improvement comprises an improvement of drug induced dyskinesia.

[Item J73]

The use of any one of the preceding items, wherein the improvement comprises an improvement of levodopa induced dyskinesia (PD-LID).

[Item K1]

Tandospirone or a pharmaceutically acceptable salt thereof for treating, improving, or preventing motor complications, wherein the tandospirone or a pharmaceutically acceptable salt thereof is parenterally administered.

[Item K1B]

Tandospirone or a pharmaceutically acceptable salt thereof for treating, improving, or preventing dyskinesia, wherein the tandospirone or a pharmaceutically acceptable salt thereof is parenterally administered.

[Item K1C]

Tandospirone or a pharmaceutically acceptable salt thereof for treating, improving, or preventing dyskinesia in a subject, wherein the tandospirone or a pharmaceutically acceptable salt thereof is parenterally administered, and the subject is undergoing drug therapy for Parkinson's disease.

[Item K1D]

Tandospirone or a pharmaceutically acceptable salt thereof for treating, improving, or preventing dyskinesia in a subject, wherein the tandospirone or a pharmaceutically acceptable salt thereof is parenterally administered, and the subject is undergoing levodopa therapy.

[Item K1E-1]

Tandospirone or a pharmaceutically acceptable salt thereof for reducing OFF time in a subject who is a Parkinson's disease patient, wherein the tandospirone or a pharmaceutically acceptable salt thereof is parenterally administered, and the subject is undergoing drug therapy.

[Item K1E]

Tandospirone or a pharmaceutically acceptable salt thereof for reducing OFF time in a subject who is a Parkinson's disease patient, wherein the tandospirone or a pharmaceutically acceptable salt thereof is parenterally administered, and the subject is undergoing drug therapy.

[Item K1F]

Tandospirone or a pharmaceutically acceptable salt thereof for reducing OFF time and increasing ON time in a subject who is a Parkinson's disease patient, wherein the tandospirone or a pharmaceutically acceptable salt thereof is parenterally administered, and the subject is undergoing drug therapy.

[Item K1G]

Tandospirone or a pharmaceutically acceptable salt thereof for reducing a non-response time (OFF time) and increasing ON time without troublesome dyskinesia in a Parkinson's disease patient, wherein the tandospirone or a pharmaceutically acceptable salt thereof is parenterally administered, and the subject is undergoing drug therapy.

[Item K1H]

Tandospirone or a pharmaceutically acceptable salt thereof for reducing a non-response time (OFF time) and increasing an antiparkinsonian action effective time (ON time) without troublesome dyskinesia in a Parkinson's disease patient, wherein the tandospirone or a pharmaceutically acceptable salt thereof is parenterally administered, and the subject is undergoing levodopa therapy.

[Item K2]

Tandospirone or a pharmaceutically acceptable salt thereof for treating, improving, or preventing motor complications in Parkinson's disease, wherein the tandospirone or a pharmaceutically acceptable salt thereof is parenterally administered.

[Item K3]

Tandospirone or a pharmaceutically acceptable salt thereof for treating, improving, or preventing motor complications in Parkinson's disease, wherein the tandospirone or a pharmaceutically acceptable salt thereof is parenterally administered, and the subject is undergoing drug therapy for Parkinson's disease.

[Item K4]

Tandospirone or a pharmaceutically acceptable salt thereof for treating, improving, or preventing motor complications in Parkinson's disease, wherein the tandospirone or a pharmaceutically acceptable salt thereof is parenterally administered, and the subject is undergoing drug therapy selected from the group consisting of drug therapy for Parkinson's disease using a levodopa containing formulation, a levodopa metabolite inhibitor, or a dopamine receptor agonist and therapy using an adjunct agent for Parkinson's disease.

[Item K5]

Tandospirone or a pharmaceutically acceptable salt thereof for treating, improving, or preventing motor complications in Parkinson's disease, wherein the tandospirone or a pharmaceutically acceptable salt thereof is parenterally administered, and the subject is undergoing dopamine replacement therapy for Parkinson's disease.

[Item K6]

Tandospirone or a pharmaceutically acceptable salt thereof for treating, improving, or preventing motor complications in Parkinson's disease, wherein the tandospirone or a pharmaceutically acceptable salt thereof is parenterally administered, and the subject is undergoing levodopa therapy for Parkinson's disease.

[Item K7]

Tandospirone or a pharmaceutically acceptable salt thereof for treating, improving, or preventing motor complications in Parkinson's disease, wherein an effective amount of the tandospirone or a pharmaceutically acceptable salt thereof is parenterally administered, and wherein the tandospirone or a pharmaceutically acceptable salt thereof sustainably maintains a dopamine level in a striatal synaptic cleft, suppresses a rapid change in a dopamine level, and/or suppresses intermittent dopamine receptor stimulation in a subject.

[Item K8]

The tandospirone or a pharmaceutically acceptable salt thereof of any one of the preceding items, which is administered so that a rebound symptom does not manifest in the subject.

[Item K9]

The tandospirone or a pharmaceutically acceptable salt thereof of any one of the preceding items, wherein the motor complications comprise motor fluctuations.

[Item K10]

The tandospirone or a pharmaceutically acceptable salt thereof of any one of the preceding items, wherein the parenteral administration is selected from transdermal administration, intradermal administration, subcutaneous administration, intramuscular administration, and a combination thereof.

[Item K11]

The tandospirone or a pharmaceutically acceptable salt thereof of any one of the preceding items, wherein the parenteral administration has sustainability or is sustainably administered.

[Item K12]

The tandospirone or a pharmaceutically acceptable salt thereof of any one of the preceding items, wherein the parenteral administration comprises transdermal administration.

[Item K13]

The tandospirone or a pharmaceutically acceptable salt thereof of any one of the preceding items, wherein the treatment, improvement, or prevention improves motor complications without exacerbating a dyskinesia symptom in Parkinson's disease.

[Item K14]

The tandospirone or a pharmaceutically acceptable salt thereof of any one of the preceding items, wherein the treatment, improvement, or prevention improves motor complications without exacerbating a levodopa induced dyskinesia (PD-LID) symptom.

[Item K15]

The tandospirone or a pharmaceutically acceptable salt thereof of any one of the preceding items, wherein the treatment, improvement, or prevention improves motor fluctuations without exacerbating a dyskinesia symptom in Parkinson's disease.

[Item K16]

The tandospirone or a pharmaceutically acceptable salt thereof of any one of the preceding items, wherein the treatment, improvement, or prevention improves motor fluctuations without exacerbating a levodopa induced dyskinesia (PD-LID) symptom.

[Item K17]

The tandospirone or a pharmaceutically acceptable salt thereof of any one of the preceding items, wherein the treatment, improvement, or prevention improves motor complications or motor fluctuations without exacerbating a dyskinesia symptom in Parkinson's disease.

[Item K18]

The tandospirone or a pharmaceutically acceptable salt thereof of any one of the preceding items, wherein the treatment, improvement, or prevention improves motor complications or motor fluctuations without a rebound symptom of a levodopa induced dyskinesia (PD-LID).

[Item K19]

The tandospirone or a pharmaceutically acceptable salt thereof of any one of the preceding items, wherein the motor fluctuations comprise a wearing-off phenomenon, an on-off phenomenon, a no-on phenomenon, a delayed on phenomenon, and a combination thereof.

[Item K20]

The tandospirone or a pharmaceutically acceptable salt thereof of any one of the preceding items, wherein treatment, improvement, or prevention of the motor fluctuations comprises prolongation of an antiparkinsonian action effective time (ON-time), a reduction of a non-response time (OFF-time), or a combination thereof.

[Item K21]

The tandospirone or a pharmaceutically acceptable salt thereof of any one of the preceding items, wherein the motor complications further comprise a dyskinesia symptom in Parkinson's disease.

[Item K22]

The tandospirone or a pharmaceutically acceptable salt thereof of any one of the preceding items, wherein the motor complications further comprise levodopa induced dyskinesia (PD-LID).

[Item K23]

The tandospirone or a pharmaceutically acceptable salt thereof of any one of the preceding items, wherein a dyskinesia symptom in Parkinson's disease comprises peak-dose dyskinesia, diphasic dyskinesia, and a combination thereof.

[Item K24]

The tandospirone or a pharmaceutically acceptable salt thereof of any one of the preceding items, wherein levodopa induced dyskinesia (PD-LID) comprises peak-dose dyskinesia, diphasic dyskinesia, and a combination thereof.

[Item K25]

The tandospirone or a pharmaceutically acceptable salt thereof of any one of the preceding items, wherein the treatment, improvement, or prevention improves motor fluctuations without a dyskinesia symptom.

[Item K26]

The tandospirone or a pharmaceutically acceptable salt thereof of any one of the preceding items, wherein the treatment, improvement, or prevention improves motor fluctuations without a troublesome dyskinesia symptom.

[Item K27]

Tandospirone or a pharmaceutically acceptable salt thereof for accomplishing improvement or prevention of a dyskinesia symptom in a Parkinson's disease patient, reduction of a period of dyskinesia manifestation in a Parkinson's disease patient, or a combination thereof, wherein the tandospirone or a pharmaceutically acceptable salt thereof does not exacerbate motor fluctuations, and the tandospirone or a pharmaceutically acceptable salt thereof is parenterally administered.

[Item K28]

The tandospirone or a pharmaceutically acceptable salt thereof of any one of the preceding items for accomplishing improvement or prevention of a levodopa induced dyskinesia (PD-LID) symptom, reduction of a period of levodopa induced dyskinesia (PD-LID) manifestation, or a combination thereof.

[Item K29]

Tandospirone or a pharmaceutically acceptable salt thereof for accomplishing improvement or prevention of a dyskinesia symptom in a Parkinson's disease patient, reduction of a period of dyskinesia manifestation in a Parkinson's disease patient, or a combination thereof, wherein the tandospirone or a pharmaceutically acceptable salt thereof does not reduce an antiparkinsonian action effective time (ON-time) associated with levodopa therapy for Parkinson's disease by a clinically significant period or longer, and/or does not prolong a non-response time (OFF-time) to a clinically significant period or longer, and wherein the tandospirone or a pharmaceutically acceptable salt thereof is parenterally administered.

[Item K30]

The tandospirone or a pharmaceutically acceptable salt thereof of any one of the preceding items for accomplishing improvement or prevention of a levodopa induced dyskinesia (PD-LID) symptom, reduction of a period of levodopa induced dyskinesia (PD-LID) manifestation, or a combination thereof, wherein the tandospirone or a pharmaceutically acceptable salt thereof does not reduce an antiparkinsonian action effective time (ON-time) associated with levodopa therapy for Parkinson's disease by a clinically significant period or longer, and/or does not prolong a non-response time (OFF-time) to a clinically significant period or longer.

[Item K31]

The tandospirone or a pharmaceutically acceptable salt thereof of any one of the preceding items, wherein the reduction of a non-response time (OFF-time) is by a clinically significant period or longer.

[Item K32]

The tandospirone or a pharmaceutically acceptable salt thereof of any one of the preceding items, wherein the reduction of a non-response time (OFF-time) is by a sufficient period to attain clinical effect.

[Item K33]

Tandospirone or a pharmaceutically acceptable salt thereof for accomplishing prolongation of an antiparkinsonian action effective time (ON-time) in Parkinson's disease, reduction of a non-response time (OFF-time), improvement or prevention of a dyskinesia symptom, reduction of a period of dyskinesia manifestation, or a combination thereof, wherein the tandospirone or a pharmaceutically acceptable salt thereof is parenterally administered.

[Item K34]

Tandospirone or a pharmaceutically acceptable salt thereof for accomplishing prolongation of an antiparkinsonian action effective time (ON-time) associated with levodopa therapy for Parkinson's disease, reduction of a non-response time (OFF-time), improvement or prevention of a levodopa induced dyskinesia (PD-LID) symptom, reduction of a period of levodopa induced dyskinesia (PD-LID) manifestation, or a combination thereof, wherein the tandospirone or a pharmaceutically acceptable salt thereof is parenterally administered.

[Item K35]

The tandospirone or a pharmaceutically acceptable salt thereof of any one of the preceding items, wherein improvement of the motor fluctuations is a clinically significant improvement or greater.

[Item K36]

The tandospirone or a pharmaceutically acceptable salt thereof of any one of the preceding items, wherein improvement of the motor fluctuations is to a sufficient level to attain a clinical effect.

[Item K37]

The tandospirone or a pharmaceutically acceptable salt thereof of any one of the preceding items, which is a transdermally administered formulation.

[Item K38]

The tandospirone or a pharmaceutically acceptable salt thereof of any one of the preceding items, which is provided as an adhesive formulation.

[Item K39]

The tandospirone or a pharmaceutically acceptable salt thereof of any one of the preceding items, wherein the transdermally administered formulation is a tape/patch.

[Item K40]

The tandospirone or a pharmaceutically acceptable salt thereof of any one of the preceding items, wherein a drug dosage of the tandospirone or a pharmaceutically acceptable salt thereof is 0.1 to 500 mg per day as a free form of tandospirone.

[Item K41]

The tandospirone or a pharmaceutically acceptable salt thereof of any one of the preceding items, wherein a drug dosage of the tandospirone or a pharmaceutically acceptable salt thereof is 3 to 250 mg per day as a free form of tandospirone.

[Item K42]

The tandospirone or a pharmaceutically acceptable salt thereof of any one of the preceding items, wherein an amount of drug penetration for the tandospirone or a pharmaceutically acceptable salt thereof is 0.1 to 100 mg per day as a free form of tandospirone.

[Item K43]

The tandospirone or a pharmaceutically acceptable salt thereof of any one of the preceding items, wherein an amount of drug penetration for the tandospirone or a pharmaceutically acceptable salt thereof is 1 to 60 mg per day as a free form of tandospirone.

[Item K44]

The tandospirone or a pharmaceutically acceptable salt thereof of any one of the preceding items, wherein the tandospirone or a pharmaceutically acceptable salt thereof is provided as a transdermally administered formulation, and a total applied area per dose is 1 to 100 $cm^2$.

[Item K45]

The tandospirone or a pharmaceutically acceptable salt thereof of any one of the preceding items, wherein the tandospirone or a pharmaceutically acceptable salt thereof is provided as a transdermally administered formulation, and a total applied area per dose is 9 to 60 $cm^2$.

[Item K46]

The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item K47]

The tandospirone or a pharmaceutically acceptable salt thereof of any one of the preceding items, wherein the tandospirone or a pharmaceutically acceptable salt thereof is administered so that a human blood (plasma) tandospirone concentration is 0.5 to 15 ng/mL for 12 hours or longer per day.

[Item K48]

The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 12 hours to 30 hours after a single administration of the tandospirone or a pharmaceutically acceptable salt thereof.

[Item K49]

The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item K50]

The tandospirone or a pharmaceutically acceptable salt thereof of any one of the preceding items, wherein the tandospirone or a pharmaceutically acceptable salt thereof is administered so that a human blood (plasma) tandospirone concentration is 0.1 to 15 ng/mL for 8 to 16 hours after administration of the tandospirone or a pharmaceutically acceptable salt thereof.

[Item K51]

The tandospirone or a pharmaceutically acceptable salt thereof of any one of the preceding items, wherein the tandospirone or a pharmaceutically acceptable salt thereof is administered so that a human blood (plasma) tandospirone concentration is 10 to 100% of a maximum blood concentration after administration for 8 to 16 hours after administration of the tandospirone or a pharmaceutically acceptable salt thereof.

[Item K52]

The tandospirone or a pharmaceutically acceptable salt thereof of any one of the preceding items, wherein the tandospirone or a pharmaceutically acceptable salt thereof is administered so that a ratio of a minimum concentration, with respect to a maximum blood concentration after administration as 100%, is 10 to 95% for a human blood (plasma) tandospirone concentration for 8 to 16 hours after administration of the tandospirone or a pharmaceutically acceptable salt thereof, and wherein the maximum blood concentration after administration is 1 to 15 ng/mL.

[Item K53]

The tandospirone or a pharmaceutically acceptable salt thereof of any one of the preceding items, wherein the tandospirone or a pharmaceutically acceptable salt thereof is administered so that a ratio of a minimum concentration, with respect to a maximum blood concentration after administration as 100%, is 10 to 95% for a human blood (plasma) tandospirone concentration for 8 to 16 hours after administration of the tandospirone or a pharmaceutically acceptable salt thereof.

[Item K54]

The tandospirone or a pharmaceutically acceptable salt thereof of any one of the preceding items, wherein the tandospirone or a pharmaceutically acceptable salt thereof is administered so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% after administration of the tandospirone or a pharmaceutically acceptable salt thereof.

[Item K55]

The tandospirone or a pharmaceutically acceptable salt thereof of any one of the preceding items, wherein the tandospirone or a pharmaceutically acceptable salt thereof is administered so that an amount of change in striatal $[^{11}C]$ raclopride receptor binding from before levodopa administration to 1 hour after administration (amount of change B/1 h) after administering the tandospirone or a pharmaceutically acceptable salt thereof is less than 10%.

[Item K56]

The tandospirone or a pharmaceutically acceptable salt thereof of any one of the preceding items, provided as an adjunct of levodopa.

[Item K57]

The tandospirone or a pharmaceutically acceptable salt thereof of any one of the preceding items, which is used with levodopa in the same formulation or concomitantly as separate formulations.

[Item K58]

Tandospirone or a pharmaceutically acceptable salt thereof as a combination tandospirone or a pharmaceutically acceptable salt thereof and (1) levodopa or (2) levodopa and a metabolizing enzyme inhibitor of levodopa for treating or preventing Parkinson's disease without accompanying or by minimizing motor complications, wherein the tandospirone or a pharmaceutically acceptable salt thereof is parenterally administered.

[Item K59]

The tandospirone or a pharmaceutically acceptable salt thereof of any one of the preceding items, wherein the motor complications comprise motor fluctuations.

[Item K60]

The tandospirone or a pharmaceutically acceptable salt thereof of any one of the preceding items, wherein the motor complications further comprise dyskinesia.

[Item K61]

The tandospirone or a pharmaceutically acceptable salt thereof of any one of the preceding items, wherein the motor complications further comprise drug induced dyskinesia.

[Item K62]

The tandospirone or a pharmaceutically acceptable salt thereof of any one of the preceding items, wherein the motor complications further comprise levodopa induced dyskinesia (PD-LID).

[Item K63]

The tandospirone or a pharmaceutically acceptable salt thereof of any one of the preceding items, wherein the tandospirone or a pharmaceutically acceptable salt thereof and the (1) or (2) are administered simultaneously or at different times.

[Item K64]

(1) levodopa or (2) levodopa and a metabolizing enzyme inhibitor of levodopa for treating or preventing Parkinson's disease without accompanying or by minimizing motor complications, wherein the (1) levodopa or (2) levodopa and a metabolizing enzyme inhibitor of levodopa is administered in combination with tandospirone or a pharmaceutically acceptable salt thereof, wherein the tandospirone or a pharmaceutically acceptable salt thereof is parenterally administered.

[Item K65]

The (1) levodopa or (2) levodopa and a metabolizing enzyme inhibitor of levodopa of any one of the preceding items, wherein the motor complications comprise dyskinesia.

[Item K66]

The (1) levodopa or (2) levodopa and a metabolizing enzyme inhibitor of levodopa of any one of the preceding items, wherein the motor complications comprise drug induced dyskinesia.

[Item K67]

The (1) levodopa or (2) levodopa and a metabolizing enzyme inhibitor of levodopa of any one of the preceding items, wherein the motor complications comprise levodopa induced dyskinesia (PD-LID).

[Item K68]

The (1) levodopa or (2) levodopa and a metabolizing enzyme inhibitor of levodopa of any one of the preceding items, wherein the tandospirone or a pharmaceutically acceptable salt thereof and the (1) or (2) are administered simultaneously or at different times.

[Item K69]

Tandospirone or a pharmaceutically acceptable salt thereof for improving the exacerbation in quality of response to levodopa therapy of a Parkinson's disease patient, wherein the tandospirone or a pharmaceutically acceptable salt thereof is parenterally administered.

[Item K70]

The tandospirone or a pharmaceutically acceptable salt thereof of any one of the preceding items, wherein the improvement comprises an improvement of motor fluctuations.

[Item K71]

The tandospirone or a pharmaceutically acceptable salt thereof of any one of the preceding items, wherein the improvement comprises an improvement of dyskinesia.

[Item K72]

The tandospirone or a pharmaceutically acceptable salt thereof of any one of the preceding items, wherein the improvement comprises an improvement of drug induced dyskinesia.

[Item K73]

The tandospirone or a pharmaceutically acceptable salt thereof of any one of the preceding items, wherein the improvement comprises an improvement of levodopa induced dyskinesia (PD-LID).

[Item L1]

A method for treating, improving, or preventing motor complications in a subject, comprising parenterally administering an effective amount of tandospirone or a pharmaceutically acceptable salt thereof.

[Item L1B]

A method for treating, improving, or preventing dyskinesia in a subject, comprising parenterally administering an effective amount of tandospirone or a pharmaceutically acceptable salt thereof.

[Item L1C]

A method for treating, improving, or preventing dyskinesia in a subject, comprising tandospirone or a pharmaceutically acceptable salt thereof, wherein the tandospirone or a pharmaceutically acceptable salt thereof is parenterally administered, and the subject is undergoing drug therapy for Parkinson's disease.

[Item L1D]

A method for treating, improving, or preventing dyskinesia in a subject, comprising parenterally administering an effective amount of tandospirone or a pharmaceutically acceptable salt thereof, wherein the subject is undergoing levodopa therapy.

[Item L1E-1]

A method for reducing OFF time in a subject who is a Parkinson's disease patient, comprising parenterally administering an effective amount of tandospirone or a pharmaceutically acceptable salt thereof, wherein the subject is undergoing drug therapy.

[Item L1E]

A method for reducing OFF time in a subject who is a Parkinson's disease patient, comprising parenterally administering an effective amount of tandospirone or a pharmaceutically acceptable salt thereof, wherein the subject is undergoing drug therapy.

[Item L1F]

A method for reducing OFF time and increasing ON time in a subject who is a Parkinson's disease patient, comprising parenterally administering an effective amount of tandospirone or a pharmaceutically acceptable salt thereof, wherein the subject is undergoing drug therapy.

[Item L1G]

A method for reducing a non-response time (OFF time) and increasing ON time without troublesome dyskinesia in a Parkinson's disease patient, comprising parenterally administering an effective amount of tandospirone or a pharmaceutically acceptable salt thereof, wherein the subject is undergoing drug therapy.

[Item L1H]

A method for reducing a non-response time (OFF time) and increasing an antiparkinsonian action effective time (ON time) without troublesome dyskinesia in a Parkinson's disease patient, comprising parenterally administering an effective amount of tandospirone or a pharmaceutically acceptable salt thereof, wherein the subject is undergoing levodopa therapy.

[Item L2]

A method for treating, improving, or preventing motor complications in Parkinson's disease, comprising parenterally administering an effective amount of tandospirone or a pharmaceutically acceptable salt thereof.

[Item L3]

A method for treating, improving, or preventing motor complications in Parkinson's disease, comprising parenterally administering an effective amount of tandospirone or a pharmaceutically acceptable salt thereof, wherein the subject is undergoing drug therapy for Parkinson's disease.

[Item L4]

A method for treating, improving, or preventing motor complications in Parkinson's disease, comprising parenterally administering an effective amount of tandospirone or a pharmaceutically acceptable salt thereof, wherein the subject is undergoing drug therapy selected from the group consisting of drug therapy for Parkinson's disease using a levodopa containing formulation, a levodopa metabolite inhibitor, or a dopamine receptor agonist and therapy using an adjunct agent for Parkinson's disease.

[Item L5]

A method for treating, improving, or preventing motor complications in Parkinson's disease, comprising parenterally administering an effective amount of tandospirone or a pharmaceutically acceptable salt thereof, wherein the subject is undergoing dopamine replacement therapy for Parkinson's disease.

[Item L6]

A method for treating, improving, or preventing motor complications in Parkinson's disease, comprising parenterally administering an effective amount of tandospirone or a pharmaceutically acceptable salt thereof, wherein the subject is undergoing levodopa therapy for Parkinson's disease.

[Item L7]

A method for treating, improving, or preventing motor complications in Parkinson's disease, comprising parenterally administering an effective amount of tandospirone or a pharmaceutically acceptable salt thereof, wherein the method sustainably maintains a dopamine level in a striatal synaptic cleft, suppresses a rapid change in a dopamine level, and/or suppresses intermittent dopamine receptor stimulation in a subject.

[Item L8]

The method of any one of the preceding items, administering so that a rebound symptom does not manifest in the subject.

[Item L9]

The method of any one of the preceding items, wherein the motor complications comprise motor fluctuations.

[Item L10]

The method of any one of the preceding items, wherein the parenteral administration is selected from transdermal administration, intradermal administration, subcutaneous administration, intramuscular administration, and a combination thereof.

[Item L11]

The method of any one of the preceding items, wherein the parenteral administration has sustainability or is sustainably administered.

[Item L12]

The method of any one of the preceding items, wherein the parenteral administration comprises transdermal administration.

[Item L13]

The method of any one of the preceding items, wherein the treatment, improvement, or prevention improves motor complications without exacerbating a dyskinesia symptom in Parkinson's disease.

[Item L14]

The method of any one of the preceding items, wherein the treatment, improvement, or prevention improves motor complications without exacerbating a levodopa induced dyskinesia (PD-LID) symptom.

[Item L15]

The method of any one of the preceding items, wherein the treatment, improvement, or prevention improves motor fluctuations without exacerbating a dyskinesia symptom in Parkinson's disease.

[Item L16]

The method of any one of the preceding items, wherein the treatment, improvement, or prevention improves motor fluctuations without exacerbating a levodopa induced dyskinesia (PD-LID) symptom.

[Item L17]

The method of any one of the preceding items, wherein the treatment, improvement, or prevention improves motor complications or motor fluctuations without exacerbating a dyskinesia symptom in Parkinson's disease.

[Item L18]

The method of any one of the preceding items, wherein the treatment, improvement, or prevention improves motor complications or motor fluctuations without a rebound symptom of a levodopa induced dyskinesia (PD-LID).

[Item L19]

The method of any one of the preceding items, wherein the motor fluctuations comprise a wearing-off phenomenon, an on-off phenomenon, a no-on phenomenon, a delayed on phenomenon, and a combination thereof.

[Item L20]

The method of any one of the preceding items, wherein treatment, improvement, or prevention of the motor fluctuations comprises prolongation of an antiparkinsonian action effective time (ON-time), a reduction of a non-response time (OFF-time), or a combination thereof.

[Item L21]

The method of any one of the preceding items, wherein the motor complications further comprise a dyskinesia symptom in Parkinson's disease.

[Item L22]

The method of any one of the preceding items, wherein the motor complications further comprise levodopa induced dyskinesia (PD-LID).

[Item L23]

The method of any one of the preceding items, wherein a dyskinesia symptom in Parkinson's disease comprises peak-dose dyskinesia, diphasic dyskinesia, and a combination thereof.

[Item L24]

The method of any one of the preceding items, wherein levodopa induced dyskinesia (PD-LID) comprises peak-dose dyskinesia, diphasic dyskinesia, and a combination thereof.

[Item L25]

The method of any one of the preceding items, wherein the treatment, improvement, or prevention improves motor fluctuations without a dyskinesia symptom.

[Item L26]

The method of any one of the preceding items, wherein the treatment, improvement, or prevention improves motor fluctuations without a troublesome dyskinesia symptom.

[Item L27]

A method for accomplishing improvement or prevention of a dyskinesia symptom in a Parkinson's disease patient, reduction of a period of dyskinesia manifestation in a Parkinson's disease patient, or a combination thereof, comprising parenterally administering an effective amount of tandospirone or a pharmaceutically acceptable salt thereof, wherein the method does not exacerbate motor fluctuations.

[Item L28]

The method of any one of the preceding items for accomplishing improvement or prevention of a levodopa induced dyskinesia (PD-LID) symptom, reduction of a period of levodopa induced dyskinesia (PD-LID) manifestation, or a combination thereof.

[Item L29]

A method for accomplishing improvement or prevention of a dyskinesia symptom in a Parkinson's disease patient, reduction of a period of dyskinesia manifestation in a Parkinson's disease patient, or a combination thereof, comprising parenterally administering an effective amount of tandospirone or a pharmaceutically acceptable salt thereof, wherein the method does not reduce an antiparkinsonian action effective time (ON-time) associated with levodopa therapy for Parkinson's disease by a clinically significant period or longer, and/or does not prolong a non-response time (OFF-time) to a clinically significant period or longer.

[Item L30]

The method of any one of the preceding items for accomplishing improvement or prevention of a levodopa induced dyskinesia (PD-LID) symptom, reduction of a period of levodopa induced dyskinesia (PD-LID) manifestation, or a combination thereof, wherein the method does not reduce an antiparkinsonian action effective time (ON-time) associated with levodopa therapy for Parkinson's disease by a clinically significant period or longer, and/or does not prolong a non-response time (OFF-time) to a clinically significant period or longer.

[Item L31]

The method of any one of the preceding items, wherein the reduction of a non-response time (OFF-time) is by a clinically significant period or longer.

[Item L32]

The method of any one of the preceding items, wherein the reduction of a non-response time (OFF-time) is by a sufficient period to attain clinical effect.

[Item L33]

A method for accomplishing prolongation of an antiparkinsonian action effective time (ON-time) in Parkinson's disease, reduction of a non-response time (OFF-time), improvement or prevention of a dyskinesia symptom, reduction of a period of dyskinesia manifestation, or a combination thereof, comprising parenterally administering an effective amount of tandospirone or a pharmaceutically acceptable salt thereof.

[Item L34]

A method for accomplishing prolongation of an antiparkinsonian action effective time (ON-time) associated with levodopa therapy for Parkinson's disease, reduction of a non-response time (OFF-time), improvement or prevention of a levodopa induced dyskinesia (PD-LID) symptom, reduction of a period of levodopa induced dyskinesia (PD-LID) manifestation, or a combination thereof, comprising parenterally administering an effective amount of tandospirone or a pharmaceutically acceptable salt thereof.

[Item L35]

The method of any one of the preceding items, wherein improvement of the motor fluctuations is a clinically significant improvement or greater.

[Item L36]

The method of any one of the preceding items, wherein improvement of the motor fluctuations is to a sufficient level to attain a clinical effect.

[Item L37]

The method of any one of the preceding items, which is a transdermally administered formulation.

[Item L38]

The method of any one of the preceding items, which is provided as an adhesive formulation.

[Item L39]

The method of any one of the preceding items, wherein the transdermally administered formulation is a tape/patch.

[Item L40]

The method of any one of the preceding items, wherein a drug dosage of the tandospirone or a pharmaceutically acceptable salt thereof is 0.1 to 500 mg per day as a free form of tandospirone.

[Item L41]

The method of any one of the preceding items, wherein a drug dosage of the tandospirone or a pharmaceutically acceptable salt thereof is 3 to 250 mg per day as a free form of tandospirone.

[Item L42]

The method of any one of the preceding items, wherein an amount of drug penetration for the tandospirone or a pharmaceutically acceptable salt thereof is 0.1 to 100 mg per day as a free form of tandospirone.

[Item L43]

The method of any one of the preceding items, wherein an amount of drug penetration for the tandospirone or a pharmaceutically acceptable salt thereof is 1 to 60 mg per day as a free form of tandospirone.

[Item L44]

The method of any one of the preceding items, wherein the tandospirone or a pharmaceutically acceptable salt thereof is provided as a transdermally administered formulation, and a total applied area per dose is 1 to 100 cm$^2$.

[Item L45]

The method of any one of the preceding items, wherein the tandospirone or a pharmaceutically acceptable salt thereof is provided as a transdermally administered formulation, and a total applied area per dose is 9 to 60 cm$^2$.

[Item L46]

The method of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item L47]

The method of any one of the preceding items, wherein the tandospirone or a pharmaceutically acceptable salt thereof is administered so that a human blood (plasma) tandospirone concentration is 0.5 to 15 ng/mL for 12 hours or longer per day.

[Item L48]

The method of any one of the preceding items, wherein the tandospirone or a pharmaceutically acceptable salt thereof is administered so that a human blood (plasma) tandospirone concentration is 0.05 to 20 ng/mL for 12 hours to 30 hours after a single administration of the tandospirone or a pharmaceutically acceptable salt thereof.

[Item L49]

The method of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item L50]

The method of any one of the preceding items, wherein the tandospirone or a pharmaceutically acceptable salt thereof is administered so that a human blood (plasma) tandospirone concentration is 0.1 to 15 ng/mL for 8 to 16 hours after administration of the tandospirone or a pharmaceutically acceptable salt thereof.

[Item L51]

The method of any one of the preceding items, wherein the tandospirone or a pharmaceutically acceptable salt thereof is administered so that a human blood (plasma) tandospirone concentration is 10 to 100% of a maximum blood concentration after administration for 8 to 16 hours after administration of the tandospirone or a pharmaceutically acceptable salt thereof.

[Item L52]

The method of any one of the preceding items, wherein the tandospirone or a pharmaceutically acceptable salt thereof is administered so that a ratio of a minimum concentration, with respect to a maximum blood concentration after administration as 100%, is 10 to 95% for a human blood (plasma) tandospirone concentration for 8 to 16 hours after administration of the tandospirone or a pharmaceutically acceptable salt thereof, and wherein the maximum blood concentration after administration is 1 to 15 ng/mL.

[Item L53]

The method of any one of the preceding items, wherein the tandospirone or a pharmaceutically acceptable salt thereof is administered so that a ratio of a minimum concentration, with respect to a maximum blood concentration after administration as 100%, is 10 to 95% for a human blood (plasma) tandospirone concentration for 8 to 16 hours after administration of the tandospirone or a pharmaceutically acceptable salt thereof.

[Item L54]
The method of any one of the preceding items, wherein the tandospirone or a pharmaceutically acceptable salt thereof is administered so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% after administration of the tandospirone or a pharmaceutically acceptable salt thereof.

[Item L55]
The method of any one of the preceding items, wherein the tandospirone or a pharmaceutically acceptable salt thereof is administered so that an amount of change in striatal [$^{11}$C] raclopride receptor binding from before levodopa administration to 1 hour after administration (amount of change B/1 h) after administering the tandospirone or a pharmaceutically acceptable salt thereof is less than 10%

[Item L56]
The method of any one of the preceding items, which provides an adjunct of levodopa.

[Item L57]
The method of any one of the preceding items, which uses levodopa in the same formulation or concomitantly as separate formulations.

[Item L58]
A method for treating or preventing Parkinson's disease without accompanying or by minimizing motor complications, comprising administering an effective amount of a combination of tandospirone or a pharmaceutically acceptable salt thereof and (1) levodopa or (2) levodopa and a metabolizing enzyme inhibitor of levodopa, wherein the tandospirone or a pharmaceutically acceptable salt thereof is parenterally administered.

[Item L59]
The method of any one of the preceding items, wherein the motor complications comprise motor fluctuations.

[Item L60]
The method of any one of the preceding items, wherein the motor complications further comprise dyskinesia.

[Item L61]
The method of any one of the preceding items, wherein the motor complications further comprise drug induced dyskinesia.

[Item L62]
The method of any one of the preceding items, wherein the motor complications further comprise levodopa induced dyskinesia (PD-LID).

[Item L63]
The method of any one of the preceding items, wherein the tandospirone or a pharmaceutically acceptable salt thereof and the (1) or (2) are administered simultaneously or at different times.

[Item L64]
A method for treating or preventing Parkinson's disease without accompanying or by minimizing motor complications, comprising administering (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt thereof, wherein the tandospirone or a pharmaceutically acceptable salt thereof is parenterally administered.

[Item L65]
The method of any one of the preceding items, wherein the motor complications comprise dyskinesia.

[Item L66]
The method of any one of the preceding items, wherein the motor complications comprise drug induced dyskinesia.

[Item L67]
The method of any one of the preceding items, wherein the motor complications comprise levodopa induced dyskinesia (PD-LID).

[Item L68]
The method of any one of the preceding items, wherein the tandospirone or a pharmaceutically acceptable salt thereof and the (1) or (2) are administered simultaneously or at different times.

[Item L69]
A method for improving the exacerbation in quality of response to levodopa therapy of a Parkinson's disease patient, comprising parenterally administering an effective amount of tandospirone or a pharmaceutically acceptable salt thereof to a Parkinson's disease patient.

[Item L70]
The method of any one of the preceding items, wherein the improvement comprises an improvement of motor fluctuations.

[Item L71]
The method of any one of the preceding items, wherein the improvement comprises an improvement of dyskinesia.

[Item L72]
The method of any one of the preceding items, wherein the improvement comprises an improvement of drug induced dyskinesia.

[Item L73]
The method of any one of the preceding items, wherein the improvement comprises an improvement of levodopa induced dyskinesia (PD-LID).

[Item 1]
A composition for treating, improving, or preventing motor complications associated with levodopa therapy for Parkinson's disease, comprising tandospirone or a pharmaceutically acceptable salt thereof, wherein the tandospirone or a pharmaceutically acceptable salt thereof is parenterally administered.

[Item 2]
The composition of item 1, wherein the motor complications comprise motor fluctuations.

[Item 3]
The composition of item 1 or 2, wherein the parenteral administration is selected from transdermal administration, intradermal administration, subcutaneous administration, intramuscular administration, and a combination thereof.

[Item 4]
The composition of any one of the preceding items, wherein the parenteral administration has sustainability or is sustainably administered.

[Item 5]
The composition of any one of the preceding items, wherein the parenteral administration comprises transdermal administration.

[Item 6]
The composition of any one of the preceding items, wherein the treatment, improvement, or prevention improves motor complications without exacerbating a levodopa induced dyskinesia (PD-LID) symptom.

[Item 7]
The composition of any one of the preceding items, wherein the treatment, improvement, or prevention improves motor fluctuations without exacerbating a levodopa induced dyskinesia (PD-LID) symptom.

[Item 8]

The composition of any one of the preceding items, wherein motor complications or motor fluctuations are improved without a rebound symptom of levodopa induced dyskinesia (PD-LID).

[Item 9]

The composition of any one of the preceding items, wherein the motor fluctuations comprise a wearing-off phenomenon, an on-off phenomenon, a no-on phenomenon, a delayed on phenomenon, and a combination thereof.

[Item 10]

The composition of any one of the preceding items, wherein treatment, improvement, or prevention of the motor fluctuations comprises prolongation of an antiparkinsonian action effective time (ON-time), a reduction of a non-response time (OFF-time), or a combination thereof.

[Item 11]

The composition of any one of the preceding items, wherein the motor complications further comprise levodopa induced dyskinesia (PD-LID).

[Item 12]

The composition of any one of the preceding items, wherein levodopa induced dyskinesia (PD-LID) comprises peak-dose dyskinesia, diphasic dyskinesia, and a combination thereof.

[Item 13]

The composition of any one of the preceding items, wherein the treatment, improvement, or prevention improves motor fluctuations without a dyskinesia symptom.

[Item 14]

The composition of any one of the preceding items, wherein the treatment, improvement, or prevention improves motor fluctuations without a troublesome dyskinesia symptom.

[Item 15]

A composition for accomplishing improvement or prevention of a levodopa induced dyskinesia (PD-LID) symptom, reduction of a period of levodopa induced dyskinesia (PD-LID) manifestation, or a combination thereof, comprising tandospirone or a pharmaceutically acceptable salt thereof, wherein the composition does not exacerbate motor fluctuations, and the tandospirone or a pharmaceutically acceptable salt thereof is parenterally administered.

[Item 16]

A composition for accomplishing improvement or prevention of a levodopa induced dyskinesia (PD-LID) symptom, reduction of a period of levodopa induced dyskinesia (PD-LID) manifestation, or a combination thereof, comprising tandospirone or a pharmaceutically acceptable salt thereof, wherein the composition does not reduce an antiparkinsonian action effective time (ON-time) associated with levodopa therapy for Parkinson's disease by a clinically significant period or longer, and/or does not prolong a non-response time (OFF-time) to a clinically significant period or longer, and wherein the tandospirone or a pharmaceutically acceptable salt thereof is parenterally administered.

[Item 17]

The composition of any one of the preceding items, wherein the reduction of a non-response time (OFF-time) is by a clinically significant period or longer.

[Item 18]

The composition of any one of the preceding items, wherein the reduction of a non-response time (OFF-time) is by a sufficient period to attain clinical effect.

[Item 19]

A composition for accomplishing prolongation of an antiparkinsonian action effective time (ON-time) associated with levodopa therapy for Parkinson's disease, reduction of a non-response time (OFF-time), improvement or prevention of a levodopa induced dyskinesia (PD-LID) symptom, reduction of a period of levodopa induced dyskinesia (PD-LID) manifestation, or a combination thereof, comprising tandospirone or a pharmaceutically acceptable salt thereof, wherein the tandospirone or a pharmaceutically acceptable salt thereof is parenterally administered.

[Item 20]

The composition of any one of the preceding items, wherein improvement of the motor fluctuations is a clinically significant improvement or greater.

[Item 21]

The composition of any one of the preceding items, wherein improvement of the motor fluctuations is to a sufficient level to attain a clinical effect.

[Item 22]

The composition of any one of the preceding items, which is a transdermally administered formulation.

[Item 23]

The composition of any one of the preceding items, which is provided as an adhesive formulation.

[Item 24]

The composition of any one of the preceding items, wherein the transdermally administered formulation is a tape/patch.

[Item 25]

The composition of any one of the preceding items, wherein a drug dosage of the tandospirone or a pharmaceutically acceptable salt thereof is 0.1 to 180 mg per day as a free form of tandospirone.

[Item 26]

The composition of any one of the preceding items, wherein an amount of drug penetration for the tandospirone or a pharmaceutically acceptable salt thereof is 0.1 to 20 mg per day as a free form of tandospirone.

[Item 27]

The composition of any one of the preceding items, wherein the tandospirone or a pharmaceutically acceptable salt thereof is provided as a transdermally administered formulation, and a total applied area per dose is 1 to 100 $cm^2$.

[Item 28]

The composition of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item 29]

The composition of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item 30]

The composition of any one of the preceding items, provided as an adjunct of levodopa.

[Item 31]

The composition of any one of the preceding items, which is used with levodopa in the same formulation or concomitantly as separate formulations.

[Item 32]

A medicament for treating or preventing Parkinson's disease without accompanying or by minimizing motor complications, comprising a combination of tandospirone or a pharmaceutically acceptable salt thereof and (1) levodopa or (2) levodopa and a metabolizing enzyme inhibitor of levodopa, wherein the tandospirone or a pharmaceutically acceptable salt thereof is parenterally administered.

[Item 33]

The medicament of any one of the preceding items, wherein the motor complications comprise motor fluctuations.

[Item 34]

The medicament of any one of the preceding items, wherein the motor complications further comprise levodopa induced dyskinesia (PD-LID).

[Item 35]

The medicament of any one of the preceding items, wherein the tandospirone or a pharmaceutically acceptable salt thereof and the (1) or (2) are administered simultaneously or at different times.

[Item 36]

A medicament for treating or preventing Parkinson's disease without accompanying or by minimizing motor complications, comprising (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt thereof, wherein the tandospirone or a pharmaceutically acceptable salt thereof is parenterally administered.

[Item 37]

The medicament of any one of the preceding items, wherein the motor complications further comprise levodopa induced dyskinesia (PD-LID).

[Item 38]

The medicament of any one of the preceding items, wherein the tandospirone or a pharmaceutically acceptable salt thereof and the (1) or (2) are administered simultaneously or at different times.

[Item 39]

A composition for improving the exacerbation in quality of response to levodopa therapy of a Parkinson's disease patient, comprising tandospirone or a pharmaceutically acceptable salt thereof, wherein the tandospirone or a pharmaceutically acceptable salt thereof is parenterally administered.

[Item 40]

The composition of any one of the preceding items, wherein the improvement comprises an improvement of motor fluctuations.

[Item 41]

The composition of any one of the preceding items, wherein the improvement comprises an improvement of levodopa induced dyskinesia (PD-LID).

[Item 42]

The medicament or composition of any one of the preceding items, wherein the tandospirone or a pharmaceutically acceptable salt thereof is a free form of tandospirone.

[Item 1A]

A composition for treating, improving, or preventing motor fluctuations associated with levodopa therapy for Parkinson's disease, comprising tandospirone or a pharmaceutically acceptable salt thereof, wherein the composition is parenterally administered.

[Item 2A]

The composition of item 1A, wherein the parenteral administration is selected from transdermal administration, intradermal administration, subcutaneous administration, intramuscular administration, and a combination thereof.

[Item 3A]

The composition of item 1A or 2A, wherein the parenteral administration has sustainability or is sustainably administered.

[Item 4A]

The composition of any one of the preceding items, wherein the parenteral administration has a low variation in blood concentration.

[Item 5A]

The composition of any one of the preceding items, wherein the parenteral administration comprises transdermal administration.

[Item 6A]

The composition of any one of the preceding items, wherein the treatment, improvement, or prevention improves motor fluctuations without exacerbating dyskinesia.

[Item 7A]

The composition of any one of the preceding items, wherein the motor fluctuations in a parkinsonian symptom comprise a wearing-off phenomenon, an on-off phenomenon, a no-on phenomenon, a delayed on phenomenon, and a combination thereof.

[Item 8A]

The composition of any one of the preceding items, wherein treatment, improvement, or prevention of the motor fluctuations comprises prolongation of an antiparkinsonian action effective time (ON-time), reduction of a non-response time (OFF-time), or a combination thereof.

[Item 9A] The composition of any one of the preceding items, wherein the reduction of an OFF-time is by a clinically significant period or longer.

[Item 10A]

The composition of any one of the preceding items, wherein the reduction of an OFF-time is by a sufficient period to attain a clinical effect.

[Item 11A]

The composition of any one of the preceding items, wherein improvement of the motor fluctuations is a clinically significant improvement or greater.

[Item 12A]

The composition of any one of the preceding items, wherein improvement of the motor fluctuations is to a sufficient level to attain a clinical effect.

[Item 13A]

The composition of any one of the preceding items, which is a transdermally administered formulation.

[Item 14A]

The composition of any one of the preceding items, which is provided as an adhesive formulation.

[Item 15A]

The composition of any one of the preceding items, wherein the transdermally administered formulation is a tape/patch.

[Item 16A]

The composition of any one of the preceding items, wherein a drug dosage of the tandospirone or a pharmaceutically acceptable salt thereof is 0.1 to 180 mg per day as a free form of tandospirone.

[Item 17A]

The composition of any one of the preceding items, wherein an amount of drug penetration for the tandospirone or a pharmaceutically acceptable salt thereof is 0.1 to 20 mg per day as a free form of tandospirone.

[Item 18A]

The composition of any one of the preceding items, wherein the tandospirone or a pharmaceutically acceptable salt thereof is provided as a transdermally administered formulation, and a total applied area per dose is 1 to 100 cm².

[Item 19A]

The composition of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item 20A]

The composition of any one of the preceding items, which is further used for treating, improving, or preventing levodopa induced dyskinesia (PD-LID).

[Item 21A]

The composition of any one of the preceding items, wherein levodopa induced dyskinesia (PD-LID) comprises peak-dose dyskinesia, diphasic dyskinesia, and a combination thereof.

[Item 22A]

The composition of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item 23A]

The composition of any one of the preceding items, provided as an adjunct of levodopa.

[Item 24A]

The composition of any one of the preceding items, which is used with levodopa in the same formulation or concomitantly as separate formulations.

[Item 25A]

A medicament for treating or preventing Parkinson's disease without accompanying or by minimizing motor fluctuations, the medicament comprising a combination of tandospirone or a pharmaceutically acceptable salt thereof and (1) levodopa or (2) levodopa and a metabolizing enzyme inhibitor of levodopa.

[Item 26A]

The medicament of any one of the preceding items, wherein the tandospirone or a pharmaceutically acceptable salt thereof and the (1) or (2) are administered simultaneously or at different times.

[Item 27A]

A medicament for treating or preventing Parkinson's disease without accompanying or by minimizing motor fluctuations, the medicament comprising (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt thereof.

[Item 28A]

The medicament of any one of the preceding items, wherein the tandospirone or a pharmaceutically acceptable salt thereof and the (1) or (2) are administered simultaneously or at different times.

[Item 29A]

A composition for improving the exacerbation in quality of response to levodopa therapy of a Parkinson's disease patient, comprising tandospirone or a pharmaceutically acceptable salt thereof, wherein the improvement comprises an improvement of motor fluctuations.

[Item 30A]

The medicament or composition of any one of the preceding items, wherein the tandospirone or a pharmaceutically acceptable salt thereof is a free form of tandospirone.

[Item A1]

A method for treating, improving, or preventing motor complications associated with levodopa therapy for Parkinson's disease, comprising parenterally administering an effective amount of tandospirone or a pharmaceutically acceptable salt thereof to a subject.

[Item A2]

The method of item A1, wherein the motor complications comprise motor fluctuations.

[Item A3]

The method of item A1 or A2, wherein the parenteral administration is selected from transdermal administration, intradermal administration, subcutaneous administration, intramuscular administration, and a combination thereof.

[Item A4]

The method of any one of the preceding items, wherein the parenteral administration has sustainability or is sustainably administered.

[Item A5]

The method of any one of the preceding items, wherein the parenteral administration comprises transdermal administration.

[Item A6]

The method of any one of the preceding items, wherein the treatment, improvement, or prevention improves motor complications without exacerbating a levodopa induced dyskinesia (PD-LID) symptom.

[Item A7]

The method of any one of the preceding items, wherein the treatment, improvement, or prevention improves motor fluctuations without exacerbating a levodopa induced dyskinesia (PD-LID) symptom.

[Item A8]

The method of any one of the preceding items, wherein motor complications or motor fluctuations are improved without a rebound symptom of levodopa induced dyskinesia (PD-LID).

[Item A9]

The method of any one of the preceding items, wherein the motor fluctuations comprise a wearing-off phenomenon, an on-off phenomenon, a no-on phenomenon, a delayed on phenomenon, and a combination thereof.

[Item A10]

The method of any one of the preceding items, wherein treatment, improvement, or prevention of the motor fluctuations comprises prolongation of an antiparkinsonian action effective time (ON-time), reduction of a non-response time (OFF-time), or a combination thereof.

[Item A11]

The method of any one of the preceding items, wherein the motor complications further comprise levodopa induced dyskinesia (PD-LID).

[Item A12]

The method of any one of the preceding items, wherein levodopa induced dyskinesia (PD-LID) comprises peak-dose dyskinesia, diphasic dyskinesia, and a combination thereof.

[Item A13]

The method of any one of the preceding items, wherein the treatment, improvement, or prevention improves motor fluctuations without a dyskinesia symptom.

[Item A14]

The method of any one of the preceding items, wherein the treatment, improvement, or prevention improves motor fluctuations without a troublesome dyskinesia symptom.

[Item A15]

A method for accomplishing improvement or prevention of a levodopa induced dyskinesia (PD-LID) symptom, reduction of a period of levodopa induced dyskinesia (PD-LID) manifestation, or a combination thereof, comprising parenterally administering an effective amount of tandospirone or a pharmaceutically acceptable salt thereof, wherein the method does not exacerbate motor fluctuations.

[Item A16]

A method for accomplishing improvement or prevention of a levodopa induced dyskinesia (PD-LID) symptom, reduction of a period of levodopa induced dyskinesia (PD-LID) manifestation, or a combination thereof, comprising parenterally administering an effective amount of tandospirone or a pharmaceutically acceptable salt thereof, wherein the method does not reduce an antiparkinsonian action effective time (ON-time) associated with levodopa therapy for Parkinson's disease by a clinically significant period or longer, and/or does not prolong a non-response time (OFF-time) to a clinically significant period or longer

[Item A17]

The method of any one of the preceding items, wherein the reduction of a non-response time (OFF-time) is by a clinically significant period or longer.

[Item A18]

The method of any one of the preceding items, wherein the reduction of a non-response time (OFF-time) is by a sufficient period to attain a clinical effect.

[Item A19]

A method for accomplishing prolongation of an antiparkinsonian action effective time (ON-time) associated with levodopa therapy for Parkinson's disease, reduction of a non-response time (OFF-time), improvement or prevention of a levodopa induced dyskinesia (PD-LID) symptom, reduction of a period of levodopa induced dyskinesia (PD-LID) manifestation, or a combination thereof, comprising parenterally administering an effective amount of tandospirone or a pharmaceutically acceptable salt thereof.

[Item A20]

The method of any one of the preceding items, wherein improvement of the motor fluctuations is a clinically significant improvement or greater.

[Item A21]

The method of any one of the preceding items, wherein improvement of the motor fluctuations is to a sufficient level to attain a clinical effect.

[Item A22]

The method of any one of the preceding items, wherein the tandospirone or a pharmaceutically acceptable salt thereof is provided as a transdermally administered formulation.

[Item A23]

The method of any one of the preceding items, wherein the tandospirone or a pharmaceutically acceptable salt thereof is provided as an adhesive formulation.

[Item A24]

The method of any one of the preceding items, wherein the transdermally administered formulation is a tape/patch.

[Item A25]

The method of any one of the preceding items, wherein a drug dosage of the tandospirone or a pharmaceutically acceptable salt thereof is 0.1 to 180 mg per day as a free form of tandospirone.

[Item A26]

The method of any one of the preceding items, wherein an amount of drug penetration for the tandospirone or a pharmaceutically acceptable salt thereof is 0.1 to 20 mg per day as a free form of tandospirone.

[Item A27]

The method of any one of the preceding items, wherein the tandospirone or a pharmaceutically acceptable salt thereof is provided as a transdermally administered formulation, and a total applied area per dose is 1 to 100 cm$^2$.

[Item A28]

The method of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item A29]

The method of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item A30]

The method of any one of the preceding items, wherein the tandospirone or a pharmaceutically acceptable salt thereof is provided as an adjunct of levodopa.

[Item A31]

The method of any one of the preceding items, wherein the tandospirone or a pharmaceutically acceptable salt thereof is used with levodopa in the same formulation or concomitantly as separate formulations.

[Item A32]

A method for treating or preventing Parkinson's disease without accompanying or by minimizing motor complications, comprising administering a combination of an effective amount of tandospirone or a pharmaceutically acceptable salt thereof and an effective amount of (1) levodopa or (2) levodopa and a metabolizing enzyme inhibitor of levodopa, wherein the tandospirone or a pharmaceutically acceptable salt thereof is parenterally administered.

[Item A33]

The method of any one of the preceding items, wherein the motor complications comprise motor fluctuations.

[Item A34]

The method of any one of the preceding items, wherein the motor complications further comprise levodopa induced dyskinesia (PD-LID).

[Item A35]

The method of any one of the preceding items, wherein the tandospirone or a pharmaceutically acceptable salt thereof and the (1) or (2) are administered simultaneously or at different times.

[Item A36]

A method for treating or preventing Parkinson's disease without accompanying or by minimizing motor complications, comprising administering an effective amount of (1) levodopa or (2) levodopa and a metabolizing enzyme inhibitor of levodopa in combination with tandospirone or a pharmaceutically acceptable salt thereof, wherein the tandospirone or a pharmaceutically acceptable salt thereof is parenterally administered.

[Item A37]

The method of any one of the preceding items, wherein the motor complications further comprise levodopa induced dyskinesia (PD-LID).

[Item A38]
The method of any one of the preceding items, wherein the tandospirone or a pharmaceutically acceptable salt thereof and the (1) or (2) are administered simultaneously or at different times.

[Item A39]
A method for improving the exacerbation in quality of response to levodopa therapy of a Parkinson's disease patient, comprising parenterally administering an effective amount of tandospirone or a pharmaceutically acceptable salt thereof.

[Item A40]
The method of any one of the preceding items, wherein the improvement comprises an improvement of motor fluctuations.

[Item A41]
The method of any one of the preceding items, wherein the improvement comprises an improvement of levodopa induced dyskinesia (PD-LID).

[Item A42]
The method of any one of the preceding items, wherein the tandospirone or a pharmaceutically acceptable salt thereof is a free form of tandospirone.

[Item A1A]
A method for treating, improving, or preventing motor fluctuations associated with levodopa therapy for Parkinson's disease in a subject, comprising parenterally administering an effective amount of tandospirone or a pharmaceutically acceptable salt thereof to the subject.

[Item A2A]
The method of item A1A, wherein the parenteral administration is selected from transdermal administration, intradermal administration, subcutaneous administration, intramuscular administration, and a combination thereof.

[Item A3A]
The method of item A1A or A2A, wherein the parenteral administration has sustainability or is sustainably administered.

[Item A4A]
The method of any one of the preceding items, wherein the parenteral administration has a low variation in blood concentration.

[Item A5A]
The method of any one of the preceding items, wherein the parenteral administration comprises transdermal administration.

[Item A6A]
The method of any one of the preceding items, wherein the treatment, improvement, or prevention improves motor fluctuations without exacerbating dyskinesia.

[Item A7A]
The method of any one of the preceding items, wherein the motor fluctuations in a parkinsonian symptom comprise a wearing-off phenomenon, an on-off phenomenon, a no-on phenomenon, a delayed on phenomenon, and a combination thereof.

[Item A8A]
The method of any one of the preceding items, wherein treatment, improvement, or prevention of the motor fluctuations comprises prolongation of an antiparkinsonian action effective time (ON-time), reduction of a non-response time (OFF-time), or a combination thereof.

[Item A9A]
The method of any one of the preceding items, wherein the reduction of an OFF-time is by a clinically significant period or longer.

[Item A10A]
The method of any one of the preceding items, wherein the reduction of an OFF-time is by a sufficient period to attain a clinical effect.

[Item A11A]
The method of any one of the preceding items, wherein improvement of the motor fluctuations is a clinically significant improvement or greater.

[Item A12A]
The method of any one of the preceding items, wherein improvement of the motor fluctuations is to a sufficient level to attain a clinical effect.

[Item A13A]
The method of any one of the preceding items, wherein the tandospirone or a pharmaceutically acceptable salt thereof is provided as a transdermally administered formulation.

[Item A14A]
The method of any one of the preceding items, wherein the tandospirone or a pharmaceutically acceptable salt thereof is provided as an adhesive formulation.

[Item A15A]
The method of any one of the preceding items, wherein the transdermally administered formulation is a tape/patch.

[Item A16A]
The method of any one of the preceding items, wherein a drug dosage of the tandospirone or a pharmaceutically acceptable salt thereof is 0.1 to 180 mg per day as a free form of tandospirone.

[Item A17A]
The method of any one of the preceding items, wherein an amount of drug penetration for the tandospirone or a pharmaceutically acceptable salt thereof is 0.1 to 20 mg per day as a free form of tandospirone.

[Item A18A]
The method of any one of the preceding items, wherein the tandospirone or a pharmaceutically acceptable salt thereof is provided as a transdermally administered formulation, and a total applied area per dose is 1 to 100 cm$^2$.

[Item A19A]
The method of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item A20A]
The method of any one of the preceding items, which is further used for treating, improving, or preventing levodopa induced dyskinesia (PD-LID).

[Item A21A]
The method of any one of the preceding items, wherein levodopa induced dyskinesia (PD-LID) comprises peak-dose dyskinesia, diphasic dyskinesia, and a combination thereof.

[Item A22A]
The method of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item A23A]
The method of any one of the preceding items, provided as an adjunct of levodopa.

[Item A24A]
The method of any one of the preceding items, which is used with levodopa in the same formulation or concomitantly as separate formulations.

[Item A25A]

A method for treating or preventing Parkinson's disease in a subject without accompanying or by minimizing motor fluctuations, comprising administering an effective amount of a combination of tandospirone or a pharmaceutically acceptable salt thereof and (1) levodopa or (2) levodopa and a metabolizing enzyme inhibitor of levodopa to the subject.

[Item A26A]

The method of any one of the preceding items, wherein the tandospirone or a pharmaceutically acceptable salt thereof and the (1) or (2) are administered simultaneously or at different times.

[Item A27A]

A method for treating or preventing Parkinson's disease without accompanying or by minimizing motor fluctuations, comprising administering an effective amount of (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt thereof.

[Item A28A]

The method of any one of the preceding items, wherein the tandospirone or a pharmaceutically acceptable salt thereof and the (1) or (2) are administered simultaneously or at different times.

[Item A29A]

A method for improving the exacerbation in quality of response to levodopa therapy of a Parkinson's disease patient, comprising tandospirone or a pharmaceutically acceptable salt thereof, wherein the improvement comprises an improvement of motor fluctuations.

[Item A30A]

The method of any one of the preceding items, wherein the tandospirone or a pharmaceutically acceptable salt thereof is a free form of tandospirone.

[Item B1]

Use of tandospirone or a pharmaceutically acceptable salt thereof in the manufacture of a medicament for treating, improving, or preventing motor complications associated with levodopa therapy for Parkinson's disease, wherein the tandospirone or a pharmaceutically acceptable salt thereof is parenterally administered.

[Item B2]

The use of item B1, wherein the motor complications comprise motor fluctuations.

[Item B3]

The use of item B1 or B2, wherein the parenteral administration is selected from transdermal administration, intradermal administration, subcutaneous administration, intramuscular administration, and a combination thereof.

[Item B4]

The use of any one of the preceding items, wherein the parenteral administration has sustainability or is sustainably administered.

[Item B5]

The use of any one of the preceding items, wherein the parenteral administration comprises transdermal administration.

[Item B6]

The use of any one of the preceding items, wherein the treatment, improvement, or prevention improves motor complications without exacerbating a levodopa induced dyskinesia (PD-LID) symptom.

[Item B7]

The use of any one of the preceding items, wherein the treatment, improvement, or prevention improves motor fluctuations without exacerbating a levodopa induced dyskinesia (PD-LID) symptom.

[Item B8]

The use of any one of the preceding items, wherein motor complications or motor fluctuations are improved without a rebound symptom of levodopa induced dyskinesia (PD-LID).

[Item B9]

The use of any one of the preceding items, wherein the motor fluctuations comprise a wearing-off phenomenon, an on-off phenomenon, a no-on phenomenon, a delayed on phenomenon, and a combination thereof.

[Item B10]

The use of any one of the preceding items, wherein treatment, improvement, or prevention of the motor fluctuations comprises prolongation of an antiparkinsonian action effective time (ON-time), reduction of a non-response time (OFF-time), or a combination thereof.

[Item B11]

The use of any one of the preceding items, wherein the motor complications further comprise levodopa induced dyskinesia (PD-LID).

[Item B12]

The use of any one of the preceding items, wherein levodopa induced dyskinesia (PD-LID) comprises peak-dose dyskinesia, diphasic dyskinesia, and a combination thereof.

[Item B13]

The use of any one of the preceding items, wherein the treatment, improvement, or prevention improves motor fluctuations without a dyskinesia symptom.

[Item B14]

The use of any one of the preceding items, wherein the treatment, improvement, or prevention improves motor fluctuations without a troublesome dyskinesia symptom.

[Item B15]

Use of tandospirone or a pharmaceutically acceptable salt thereof for the manufacture of a medicament for accomplishing improvement or prevention of a levodopa induced dyskinesia (PD-LID) symptom, reduction of a period of levodopa induced dyskinesia (PD-LID) manifestation, or a combination thereof, wherein the medicament does not exacerbate motor fluctuations, and the tandospirone or a pharmaceutically acceptable salt thereof is parenterally administered.

[Item B16]

Use of tandospirone or a pharmaceutically acceptable salt thereof for the manufacture of a medicament for accomplishing improvement or prevention of a levodopa induced dyskinesia (PD-LID) symptom, reduction of a period of levodopa induced dyskinesia (PD-LID) manifestation, or a combination thereof, wherein the medicament does not reduce an antiparkinsonian action effective time (ON-time) associated with levodopa therapy for Parkinson's disease by a clinically significant period or longer, and/or does not prolong a non-response time (OFF-time) to a clinically significant period or longer, wherein the tandospirone or a pharmaceutically acceptable salt thereof is parenterally administered.

[Item B17]

The use of any one of the preceding items, wherein the reduction of a non-response time (OFF-time) is by a clinically significant period or longer.

[Item B18]

The use of any one of the preceding items, wherein the reduction of a non-response time (OFF-time) is by a sufficient period to attain clinical effect.

[Item B19]

Use of tandospirone or a pharmaceutically acceptable salt thereof for the manufacture of a medicament for accomplishing prolongation of an antiparkinsonian action effective time (ON-time) associated with levodopa therapy for Parkinson's disease, reduction of a non-response time (OFF-time), improvement or prevention of a levodopa induced dyskinesia (PD-LID) symptom, reduction of a period of levodopa induced dyskinesia (PD-LID) manifestation, or a combination thereof, wherein the tandospirone or a pharmaceutically acceptable salt thereof is parenterally administered.

[Item B20]

The use of any one of the preceding items, wherein improvement of the motor fluctuations is a clinically significant improvement or greater.

[Item B21]

The use of any one of the preceding items, wherein improvement of the motor fluctuations is to a sufficient level to attain a clinical effect.

[Item B22]

The use of any one of the preceding items, wherein the medicament is provided as a transdermally administered formulation.

[Item B23]

The use of any one of the preceding items, wherein the medicament is provided as an adhesive formulation.

[Item B24]

The use of any one of the preceding items, wherein the transdermally administered formulation is a tape/patch.

[Item B25]

The use of any one of the preceding items, wherein a drug dosage of the tandospirone or a pharmaceutically acceptable salt thereof is 0.1 to 180 mg per day as a free form of tandospirone.

[Item B26]

The use of any one of the preceding items, wherein an amount of drug penetration for the tandospirone or a pharmaceutically acceptable salt thereof is 0.1 to 20 mg per day as a free form of tandospirone.

[Item B27]

The use of any one of the preceding items, wherein the tandospirone or a pharmaceutically acceptable salt thereof is provided as a transdermally administered formulation, and a total applied area per dose is 1 to 100 cm$^2$.

[Item B28]

The use of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item B29]

The use of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item B30]

The use of any one of the preceding items, wherein the medicament is provided as an adjunct of levodopa.

[Item B31]

The use of any one of the preceding items, wherein the medicament is used with levodopa in the same formulation or concomitantly as separate formulations.

[Item B32]

Use of a combination of tandospirone or a pharmaceutically acceptable salt thereof and (1) levodopa or (2) levodopa and a metabolizing enzyme inhibitor of levodopa for the manufacture of a medicament for treating or preventing Parkinson's disease without accompanying or by minimizing motor complications, wherein the tandospirone or a pharmaceutically acceptable salt thereof is parenterally administered.

[Item B33]

The medicament of any one of the preceding items, wherein the motor complications comprise motor fluctuations.

[Item B34]

The medicament of any one of the preceding items, wherein the motor complications further comprise levodopa induced dyskinesia (PD-LID).

[Item B35]

The medicament of any one of the preceding items, wherein the tandospirone or a pharmaceutically acceptable salt thereof and the (1) or (2) are administered simultaneously or at different times.

[Item B36]

Use of (1) levodopa or (2) levodopa and a metabolizing enzyme inhibitor of levodopa for the manufacture of a medicament for treating or preventing Parkinson's disease without accompanying or by minimizing motor complications, wherein the (1) levodopa or (2) levodopa and a metabolizing enzyme inhibitor of levodopa is administered in combination with tandospirone or a pharmaceutically acceptable salt thereof, and wherein the tandospirone or a pharmaceutically acceptable salt thereof is parenterally administered.

[Item B37]

The use of any one of the preceding items, wherein the motor complications further comprise levodopa induced dyskinesia (PD-LID).

[Item B38]

The use of any one of the preceding items, wherein the tandospirone or a pharmaceutically acceptable salt thereof and the (1) or (2) are administered simultaneously or at different times.

[Item B39]

Use of tandospirone or a pharmaceutically acceptable salt thereof for the manufacture of a medicament for improving the exacerbation in quality of response to levodopa therapy of a Parkinson's disease patient, wherein the tandospirone or a pharmaceutically acceptable salt thereof is parenterally administered.

[Item B40]

The use of any one of the preceding items, wherein the improvement comprises an improvement of motor fluctuations.

[Item B41]

The use of any one of the preceding items, wherein the improvement comprises an improvement of levodopa induced dyskinesia (PD-LID).

[Item B42]

The use of any one of the preceding items, wherein the tandospirone or a pharmaceutically acceptable salt thereof is a free form of tandospirone.

[Item B1A]

Use of tandospirone or a pharmaceutically acceptable salt thereof for the manufacture of a medicament for treating, improving, or preventing motor fluctuations associated with levodopa therapy for Parkinson's disease, wherein the use is administration through parenteral administration.

[Item B2A]

The use of item B1A, wherein the parenteral administration is selected from transdermal administration, intradermal administration, subcutaneous administration, intramuscular administration, and a combination thereof.

[Item B3A]

The use of item B1A or B2A, wherein the parenteral administration has sustainability or is sustainably administered.

[Item B4A]

The use of any one of the preceding items, wherein the parenteral administration has a low variation in blood concentration.

[Item B5A]

The use of any one of the preceding items, wherein the parenteral administration comprises transdermal administration.

[Item B6A]

The use of any one of the preceding items, wherein the treatment, improvement, or prevention improves motor fluctuations without exacerbating dyskinesia.

[Item B7A]

The use of any one of the preceding items, wherein the motor fluctuations in a parkinsonian symptom comprise a wearing-off phenomenon, an on-off phenomenon, a no-on phenomenon, a delayed on phenomenon, and a combination thereof.

[Item B8A]

The use of any one of the preceding items, wherein treatment, improvement, or prevention of the motor fluctuations comprises prolongation of an antiparkinsonian action effective time (ON-time), reduction of a non-response time (OFF-time), or a combination thereof.

[Item B9A]

The use of any one of the preceding items, wherein the reduction of an OFF-time is by a clinically significant period or longer.

[Item B10A]

The use of any one of the preceding items, wherein the reduction of an OFF-time is by a sufficient period to attain a clinical effect.

[Item B11A]

The use of any one of the preceding items, wherein improvement of the motor fluctuations is a clinically significant improvement or greater.

[Item B12A]

The use of any one of the preceding items, wherein improvement of the motor fluctuations is to a sufficient level to attain a clinical effect.

[Item B13A]

The use of any one of the preceding items, wherein the medicament is provided as a transdermally administered formulation.

[Item B14A]

The use of any one of the preceding items, wherein the medicament is provided as an adhesive formulation.

[Item B15A]

The use of any one of the preceding items, wherein the transdermally administered formulation is a tape/patch.

[Item B16A]

The use of any one of the preceding items, wherein a drug dosage of the tandospirone or a pharmaceutically acceptable salt thereof is 0.1 to 180 mg per day as a free form of tandospirone.

[Item B17A]

The use of any one of the preceding items, wherein an amount of drug penetration for the tandospirone or a pharmaceutically acceptable salt thereof is 0.1 to 20 mg per day as a free form of tandospirone.

[Item B18A]

The use of any one of the preceding items, wherein the tandospirone or a pharmaceutically acceptable salt thereof is provided as a transdermally administered formulation, and a total applied area per dose is 1 to 100 $cm^2$.

[Item B19A]

The use of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item B20A]

The use of any one of the preceding items, which is further used for treating, improving, or preventing levodopa induced dyskinesia (PD-LID).

[Item B21A]

The use of any one of the preceding items, wherein levodopa induced dyskinesia (PD-LID) comprises peak-dose dyskinesia, diphasic dyskinesia, and a combination thereof.

[Item B22A]

The use of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item B23A]

The use of any one of the preceding items, wherein the medicament is provided as an adjunct of levodopa.

[Item B24A]

The use of any one of the preceding items, wherein the medicament is used with levodopa in the same formulation or concomitantly as separate formulations.

[Item B25A]

Use of a combination of tandospirone or a pharmaceutically acceptable salt thereof and (1) levodopa or (2) levodopa and a metabolizing enzyme inhibitor of levodopa for the manufacture of a medicament for treating or preventing Parkinson's disease without accompanying or by minimizing motor fluctuations.

[Item B26A]

The use of any one of the preceding items, wherein the tandospirone or a pharmaceutically acceptable salt thereof and the (1) or (2) are administered simultaneously or at different times.

[Item B27A]

Use of a combination of tandospirone or a pharmaceutically acceptable salt thereof and (1) levodopa or (2) levodopa and a metabolizing enzyme inhibitor of levodopa for the manufacture of a medicament for treating or preventing Parkinson's disease without accompanying or by minimizing motor fluctuations, wherein the (1) levodopa or (2) levodopa and a metabolizing enzyme inhibitor of levodopa is administered in combination with tandospirone or a pharmaceutically acceptable salt thereof.

[Item B28A]

The use of any one of the preceding items, wherein the tandospirone or a pharmaceutically acceptable salt thereof and the (1) or (2) are administered simultaneously or at different times.

[Item B29A]
Use of tandospirone or a pharmaceutically acceptable salt thereof for the manufacture of a medicament for improving the exacerbation in quality of response to levodopa therapy of a Parkinson's disease patient, wherein the improvement comprises an improvement of motor fluctuations.

[Item B30A]
The use of any one of the preceding items, wherein the tandospirone or a pharmaceutically acceptable salt thereof is a free form of tandospirone.

[Item C1]
Tandospirone or a pharmaceutically acceptable salt thereof for treating, improving, or preventing motor complications associated with levodopa therapy for Parkinson's disease, wherein the tandospirone or a pharmaceutically acceptable salt thereof is parenterally administered.

[Item C2]
The tandospirone or a pharmaceutically acceptable salt thereof of item C1, wherein the motor complications comprise motor fluctuations.

[Item C3]
The tandospirone or a pharmaceutically acceptable salt thereof of item C1 or C2, wherein the parenteral administration is selected from transdermal administration, intradermal administration, subcutaneous administration, intramuscular administration, and a combination thereof.

[Item C4]
The tandospirone or a pharmaceutically acceptable salt thereof of any one of the preceding items, wherein the parenteral administration has sustainability or is sustainably administered.

[Item C5]
The tandospirone or a pharmaceutically acceptable salt thereof of any one of the preceding items, wherein the parenteral administration comprises transdermal administration.

[Item 06]
The tandospirone or a pharmaceutically acceptable salt thereof of any one of the preceding items, wherein the treatment, improvement, or prevention improves motor complications without exacerbating a levodopa induced dyskinesia (PD-LID) symptom.

[Item C7]
The tandospirone or a pharmaceutically acceptable salt thereof of any one of the preceding items, wherein the treatment, improvement, or prevention improves motor fluctuations without exacerbating a levodopa induced dyskinesia (PD-LID) symptom.

[Item C8]
The tandospirone or a pharmaceutically acceptable salt thereof of any one of the preceding items, wherein motor complications or motor fluctuations are improved without a rebound symptom of levodopa induced dyskinesia (PD-LID).

[Item C9]
The tandospirone or a pharmaceutically acceptable salt thereof of any one of the preceding items, wherein the motor fluctuations comprise a wearing-off phenomenon, an on-off phenomenon, a no-on phenomenon, a delayed on phenomenon, and a combination thereof.

[Item 010]
The tandospirone or a pharmaceutically acceptable salt thereof of any one of the preceding items, wherein treatment, improvement, or prevention of the motor fluctuations comprises prolongation of an antiparkinsonian action effective time (ON-time), reduction of a non-response time (OFF-time), or a combination thereof.

[Item C11]
The tandospirone or a pharmaceutically acceptable salt thereof of any one of the preceding items, wherein the motor complications further comprise levodopa induced dyskinesia (PD-LID).

[Item C12]
The tandospirone or a pharmaceutically acceptable salt thereof of any one of the preceding items, wherein levodopa induced dyskinesia (PD-LID) comprises peak-dose dyskinesia, diphasic dyskinesia, and a combination thereof.

[Item C13]
The tandospirone or a pharmaceutically acceptable salt thereof of any one of the preceding items, wherein the treatment, improvement, or prevention improves motor fluctuations without a dyskinesia symptom.

[Item C14]
The tandospirone or a pharmaceutically acceptable salt thereof of any one of the preceding items, wherein the treatment, improvement, or prevention improves motor fluctuations without a troublesome dyskinesia symptom.

[Item C15]
Tandospirone or a pharmaceutically acceptable salt thereof for accomplishing improvement or prevention of a levodopa induced dyskinesia (PD-LID) symptom, reduction of a period of levodopa induced dyskinesia (PD-LID) manifestation, or a combination thereof, comprising tandospirone or a pharmaceutically acceptable salt thereof, wherein the tandospirone or a pharmaceutically acceptable salt thereof does not exacerbate motor fluctuations, and the tandospirone or a pharmaceutically acceptable salt thereof is parenterally administered.

[Item C16]
Tandospirone or a pharmaceutically acceptable salt thereof for accomplishing improvement or prevention of a levodopa induced dyskinesia (PD-LID) symptom, reduction of a period of levodopa induced dyskinesia (PD-LID) manifestation, or a combination thereof, wherein the tandospirone or a pharmaceutically acceptable salt thereof does not reduce an antiparkinsonian action effective time (ON-time) associated with levodopa therapy for Parkinson's disease by a clinically significant period or longer, and/or does not prolong a non-response time (OFF-time) to a clinically significant period or longer and wherein the tandospirone or a pharmaceutically acceptable salt thereof is parenterally administered.

[Item C17]
The tandospirone or a pharmaceutically acceptable salt thereof of any one of the preceding items, wherein the reduction of a non-response time (OFF-time) is by a clinically significant period or longer.

[Item C18]
The tandospirone or a pharmaceutically acceptable salt thereof of any one of the preceding items, wherein the reduction of a non-response time (OFF-time) is by a sufficient period to attain clinical effect.

[Item C19] Tandospirone or a pharmaceutically acceptable salt thereof for accomplishing prolongation of an antiparkinsonian action effective time (ON-time) associated with levodopa therapy for Parkinson's disease, comprising tandospirone or a pharmaceutically acceptable salt thereof, reduction of a non-response time (OFF-time), improvement or prevention of a levodopa induced dyskinesia (PD-LID) symptom, reduction of a period of levodopa induced dyskinesia (PD-LID) manifestation, or a combination thereof, wherein the tandospirone or a pharmaceutically acceptable salt thereof is parenterally administered.

[Item C20]
The tandospirone or a pharmaceutically acceptable salt thereof of any one of the preceding items, wherein improvement of the motor fluctuations is a clinically significant improvement or greater.
[Item C21]
The tandospirone or a pharmaceutically acceptable salt thereof of any one of the preceding items, wherein improvement of the motor fluctuations is to a sufficient level to attain a clinical effect.
[Item C22]
The tandospirone or a pharmaceutically acceptable salt thereof of any one of the preceding items, which is a transdermally administered formulation.
[Item C23]
The tandospirone or a pharmaceutically acceptable salt thereof of any one of the preceding items, which is provided as an adhesive formulation.
[Item C24]
The tandospirone or a pharmaceutically acceptable salt thereof of any one of the preceding items, wherein the transdermally administered formulation is a tape/patch.
[Item C25]
The tandospirone or a pharmaceutically acceptable salt thereof of any one of the preceding items, wherein a drug dosage of the tandospirone or a pharmaceutically acceptable salt thereof is 0.1 to 180 mg per day as a free form of tandospirone.
[Item C26]
The tandospirone or a pharmaceutically acceptable salt thereof of any one of the preceding items, wherein an amount of drug penetration for the tandospirone or a pharmaceutically acceptable salt thereof is 0.1 to 20 mg per day as a free form of tandospirone.
[Item C27]
The tandospirone or a pharmaceutically acceptable salt thereof of any one of the preceding items, wherein the tandospirone or a pharmaceutically acceptable salt thereof is provided as a transdermally administered formulation, and a total applied area per dose is 1 to 100 cm$^2$.
[Item C28]
The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 12 hours or longer per day.
[Item C29]
The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.
[Item C30]
The tandospirone or a pharmaceutically acceptable salt thereof of any one of the preceding items, provided as an adjunct of levodopa.
[Item C31]
The tandospirone or a pharmaceutically acceptable salt thereof of any one of the preceding items, which is used with levodopa in the same formulation or concomitantly as separate formulations.
[Item C32]
A combination of tandospirone or a pharmaceutically acceptable salt thereof and (1) levodopa or (2) levodopa and a metabolizing enzyme inhibitor of levodopa for treating or preventing Parkinson's disease without accompanying or by minimizing motor complications, wherein the tandospirone or a pharmaceutically acceptable salt thereof is parenterally administered.
[Item C33]
The combination of any one of the preceding items, wherein the motor complications further comprise motor fluctuations.
[Item C34]
The combination of any one of the preceding items, wherein the motor complications further comprise levodopa induced dyskinesia (PD-LID).
[Item C35]
The combination of any one of the preceding items, wherein the tandospirone or a pharmaceutically acceptable salt thereof and the (1) or (2) are administered simultaneously or at different times.
[Item C36]
(1) levodopa or (2) levodopa and a metabolizing enzyme inhibitor of levodopa for treating or preventing Parkinson's disease without accompanying or by minimizing motor complications, wherein the (1) levodopa or (2) levodopa and a metabolizing enzyme inhibitor of levodopa is administered in combination with tandospirone or a pharmaceutically acceptable salt thereof, and wherein the tandospirone or a pharmaceutically acceptable salt thereof is parenterally administered.
[Item C37]
The (1) levodopa or (2) levodopa and a metabolizing enzyme inhibitor of levodopa of any one of the preceding items, wherein the motor complications further comprise levodopa induced dyskinesia (PD-LID).
[Item C38]
The (1) levodopa or (2) levodopa and a metabolizing enzyme inhibitor of levodopa of any one of the preceding items, wherein the tandospirone or a pharmaceutically acceptable salt thereof and the (1) or (2) are administered simultaneously or at different times.
[Item C39]
Tandospirone or a pharmaceutically acceptable salt thereof for improving the exacerbation in quality of response to levodopa therapy of a Parkinson's disease patient, wherein the tandospirone or a pharmaceutically acceptable salt thereof is parenterally administered.
[Item C40]
The tandospirone or a pharmaceutically acceptable salt thereof of any one of the preceding items, wherein the improvement comprises an improvement of motor fluctuations.
[Item C41]
The tandospirone or a pharmaceutically acceptable salt thereof of any one of the preceding items, wherein the improvement comprises an improvement of levodopa induced dyskinesia (PD-LID).
[Item C42]
The medicament, tandospirone or a pharmaceutically acceptable salt thereof, combination, or (1) levodopa or (2) levodopa and a metabolizing enzyme inhibitor of levodopa of any one of the preceding items, wherein the tandospirone or a pharmaceutically acceptable salt thereof is a free form of tandospirone.
[Item C1A]
Tandospirone or a pharmaceutically acceptable salt thereof for treating, improving, or preventing motor fluctuations associated with levodopa therapy for Parkinson's disease, wherein the tandospirone or a pharmaceutically acceptable salt thereof is parenterally administered.

[Item C2A]
The tandospirone or a pharmaceutically acceptable salt thereof of item CIA, wherein the parenteral administration is selected from transdermal administration, intradermal administration, subcutaneous administration, intramuscular administration, and a combination thereof.

[Item C3A]
The tandospirone or a pharmaceutically acceptable salt thereof of item CIA or C2A, wherein the parenteral administration has sustainability or is sustainably administered.

[Item C4A]
The tandospirone or a pharmaceutically acceptable salt thereof of any one of the preceding items, wherein the parenteral administration has a low variation in blood concentration.

[Item C5A]
The tandospirone or a pharmaceutically acceptable salt thereof of any one of the preceding items, wherein the parenteral administration comprises transdermal administration.

[Item C6A]
The tandospirone or a pharmaceutically acceptable salt thereof of any one of the preceding items, wherein the treatment, improvement, or prevention improves motor fluctuations without exacerbating dyskinesia.

[Item C7A]
The tandospirone or a pharmaceutically acceptable salt thereof of any one of the preceding items, wherein the motor fluctuations in a parkinsonian symptom comprise a wearing-off phenomenon, an on-off phenomenon, a no-on phenomenon, a delayed on phenomenon, and a combination thereof.

[Item C8A]
The tandospirone or a pharmaceutically acceptable salt thereof of any one of the preceding items, wherein treatment, improvement, or prevention of the motor fluctuations comprises prolongation of an antiparkinsonian action effective time (ON-time), reduction of a non-response time (OFF-time), or a combination thereof.

[Item C9A]
The tandospirone or a pharmaceutically acceptable salt thereof of any one of the preceding items, wherein the reduction of an OFF-time is by a clinically significant period or longer.

[Item C10A]
The tandospirone or a pharmaceutically acceptable salt thereof of any one of the preceding items, wherein the reduction of an OFF-time is by a sufficient period to attain a clinical effect.

[Item C11A]
The tandospirone or a pharmaceutically acceptable salt thereof of any one of the preceding items, wherein improvement of the motor fluctuations is a clinically significant improvement or greater.

[Item C12A]
The tandospirone or a pharmaceutically acceptable salt thereof of any one of the preceding items, wherein improvement of the motor fluctuations is to a sufficient level to attain a clinical effect.

[Item C13A]
The tandospirone or a pharmaceutically acceptable salt thereof of any one of the preceding items, which is a transdermally administered formulation.

[Item C14A]
The tandospirone or a pharmaceutically acceptable salt thereof of any one of the preceding items, which is provided as an adhesive formulation.

[Item C15A]
The tandospirone or a pharmaceutically acceptable salt thereof of any one of the preceding items, wherein the transdermally administered formulation is a tape/patch.

[Item C16A]
The tandospirone or a pharmaceutically acceptable salt thereof of any one of the preceding items, wherein a drug dosage of the tandospirone or a pharmaceutically acceptable salt thereof is 0.1 to 180 mg per day as a free form of tandospirone.

[Item C17A]
The tandospirone or a pharmaceutically acceptable salt thereof of any one of the preceding items, wherein an amount of drug penetration for the tandospirone or a pharmaceutically acceptable salt thereof is 0.1 to 20 mg per day as a free form of tandospirone.

[Item C18A]
The tandospirone or a pharmaceutically acceptable salt thereof of any one of the preceding items, wherein the tandospirone or a pharmaceutically acceptable salt thereof is provided as a transdermally administered formulation, and a total applied area per dose is 1 to 100 $cm^2$.

[Item C19A]
The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item C20A]
The tandospirone or a pharmaceutically acceptable salt thereof of any one of the preceding items, which is further used for treating, improving, or preventing levodopa induced dyskinesia (PD-LID).

[Item C21A]
The tandospirone or a pharmaceutically acceptable salt thereof of any one of the preceding items, wherein levodopa induced dyskinesia (PD-LID) comprises peak-dose dyskinesia, diphasic dyskinesia, and a combination thereof.

[Item C22A]
The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item C23A]
The tandospirone or a pharmaceutically acceptable salt thereof of any one of the preceding items, provided as an adjunct of levodopa.

[Item C24A]
The tandospirone or a pharmaceutically acceptable salt thereof of any one of the preceding items, which is used with levodopa in the same formulation or concomitantly as separate formulations.

[Item C25A]
A combination of tandospirone or a pharmaceutically acceptable salt thereof and (1) levodopa or (2) levodopa and a metabolizing enzyme inhibitor of levodopa for treating or preventing Parkinson's disease without accompanying or by minimizing motor fluctuations.

[Item C26A]

The combination of any one of the preceding items, wherein the tandospirone or a pharmaceutically acceptable salt thereof and the (1) or (2) are administered simultaneously or at different times.

[Item C27A]

(1) levodopa or (2) levodopa and a metabolizing enzyme inhibitor of levodopa for treating or preventing Parkinson's disease without accompanying or by minimizing motor fluctuations, wherein the (1) levodopa or (2) levodopa and a metabolizing enzyme inhibitor of levodopa is administered in combination with tandospirone or a pharmaceutically acceptable salt thereof.

[Item C28A]

The (1) levodopa or (2) levodopa and a metabolizing enzyme inhibitor of levodopa of any one of the preceding items, wherein the tandospirone or a pharmaceutically acceptable salt thereof and the (1) or (2) are administered simultaneously or at different times.

[Item C29A]

Tandospirone or a pharmaceutically acceptable salt thereof for improving the exacerbation in quality of response to levodopa therapy of a Parkinson's disease patient, wherein the improvement comprises an improvement of motor fluctuations.

[Item C30A]

The medicament, tandospirone or a pharmaceutically acceptable salt thereof, combination, or (1) levodopa or (2) levodopa and a metabolizing enzyme inhibitor of levodopa of any one of the preceding items, wherein the tandospirone or a pharmaceutically acceptable salt thereof is a free form of tandospirone.

[Item 1D]

A composition for treating, improving, or preventing Parkinson's disease levodopa induced dyskinesia (PD-LID), comprising tandospirone or a pharmaceutically acceptable salt thereof, wherein the composition is parenterally administered.

[Item 2D]

The composition of item 1D, wherein the parenteral administration is selected from transdermal administration, intradermal administration, subcutaneous administration, intramuscular administration, and a combination thereof.

[Item 3D]

The composition of item 1D or 2D, wherein the parenteral administration has sustainability or is sustainably administered.

[Item 4D]

The composition of any one of the preceding items, wherein the parenteral administration has a low variation in blood concentration.

[Item 5D]

The composition of any one of the preceding items, wherein the parenteral administration comprises transdermal administration.

[Item 6D]

The composition of any one of the preceding items, wherein treatment or improvement of the PD-LID improves PD-LID without a rebound symptom.

[Item 7D]

The composition of any one of the preceding items, wherein the PD-LID comprises peak-dose dyskinesia, diphasic dyskinesia, and a combination thereof.

[Item 8D]

The composition of any one of the preceding items, wherein treatment, improvement, or prevention of the PD-LID comprises treatment, improvement, or prevention of a PD-LID symptom, reduction of a period of PD-LID manifestation, or a combination thereof.

[Item 9D]

The composition of any one of the preceding items, wherein treatment or improvement of the PD-LID is for a clinically significant period or longer.

[Item 10D]

The composition of any one of the preceding items, wherein treatment or improvement of the PD-LID is for a sufficient period to attain a clinical effect.

[Item 11D]

The composition of any one of the preceding items, wherein treatment or improvement of the PD-LID is a clinically significant improvement or greater.

[Item 12D]

The composition of any one of the preceding items, wherein treatment or improvement of the PD-LID is to a sufficient level to attain a clinical effect.

[Item 13D]

The composition of any one of the preceding items, which is a transdermally administered formulation.

[Item 14D]

The composition of any one of the preceding items, which is provided as an adhesive formulation.

[Item 15D]

The composition of any one of the preceding items, wherein the transdermally administered formulation is a tape/patch.

[Item 16D]

The composition of any one of the preceding items, wherein a drug dosage of the tandospirone or a pharmaceutically acceptable salt thereof is 0.1 to 180 mg per day as a free form of tandospirone.

[Item 17D]

The composition of any one of the preceding items, wherein an amount of drug penetration for the tandospirone or a pharmaceutically acceptable salt thereof is 0.1 to 20 mg per day as a free form of tandospirone.

[Item 18D]

The composition of any one of the preceding items, wherein the tandospirone or a pharmaceutically acceptable salt thereof is provided as a transdermally administered formulation, and a total applied area per dose is 1 to 100 $cm^2$.

[Item 19D]

The composition of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item 20D]

The composition of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item 21D]

The composition of any one of the preceding items, provided as an adjunct of levodopa.

[Item 22D]

The composition of any one of the preceding items, which is used with levodopa in the same formulation or concomitantly as separate formulations.

[Item 23D]

A medicament for treating or preventing Parkinson's disease without accompanying or by minimizing levodopa induced dyskinesia (PD-LID), wherein the medicament comprises a combination of tandospirone or a pharmaceutically acceptable salt thereof and (1) levodopa or (2) levodopa and a metabolizing enzyme inhibitor of levodopa.

[Item 24D]

The medicament of any one of the preceding items, wherein the tandospirone or a pharmaceutically acceptable salt thereof and the (1) or (2) are administered simultaneously or at different times.

[Item 25D]

A medicament for treating or preventing Parkinson's disease without accompanying or by minimizing levodopa induced dyskinesia (PD-LID), the medicament comprising (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt thereof.

[Item 26D]

The medicament of any one of the preceding items, wherein the tandospirone or a pharmaceutically acceptable salt thereof and the (1) or (2) are administered simultaneously or at different times.

[Item 27D]

A composition for improving the exacerbation in quality of response to levodopa therapy of a Parkinson's disease patient, comprising tandospirone or a pharmaceutically acceptable salt thereof, wherein the improvement comprises an improvement of levodopa induced dyskinesia (PD-LID).

[Item 28D]

The tandospirone or a pharmaceutically acceptable salt thereof, composition, or medicament of any one of the preceding items, wherein the tandospirone or a pharmaceutically acceptable salt thereof is a free form of tandospirone.

[Item D1D]

A method for treating, improving, or preventing Parkinson's disease levodopa induced dyskinesia (PD-LID) in a subject, comprising parenterally administering an effective amount of tandospirone or a pharmaceutically acceptable salt thereof to the subject.

[Item D2D]

The method of item D1D, wherein the parenteral administration is selected from transdermal administration, intradermal administration, subcutaneous administration, intramuscular administration, and a combination thereof.

[Item D3D]

The method of item D1D or D2D, wherein the parenteral administration has sustainability or is sustainably administered.

[Item D4D]

The method of any one of the preceding items, wherein the parenteral administration has a low variation in blood concentration.

[Item D5D]

The method of any one of the preceding items, wherein the parenteral administration comprises transdermal administration.

[Item D6D]

The method of any one of the preceding items, wherein treatment or improvement of the PD-LID improves PD-LID without a rebound symptom.

[Item D7D]

The method of any one of the preceding items, wherein the PD-LID comprises peak-dose dyskinesia, diphasic dyskinesia, and a combination thereof.

[Item D8D]

The method of any one of the preceding items, wherein treatment, improvement, or prevention of the PD-LID comprises treatment, improvement, or prevention of a PD-LID symptom, reduction of a period of PD-LID manifestation, or a combination thereof.

[Item D9D]

The method of any one of the preceding items, wherein treatment or improvement of the PD-LID is for a clinically significant period or longer.

[Item D10D]

The method of any one of the preceding items, wherein treatment or improvement of the PD-LID is for a sufficient period to attain a clinical effect.

[Item D11D]

The method of any one of the preceding items, wherein treatment or improvement of the PD-LID is a clinically significant improvement or greater.

[Item D12D]

The method of any one of the preceding items, wherein treatment or improvement of the PD-LID is to a sufficient level to attain a clinical effect.

[Item D13D]

The method of any one of the preceding items, wherein the tandospirone or a pharmaceutically acceptable salt thereof is administered as a transdermally administered formulation.

[Item D14D]

The method of any one of the preceding items, wherein the tandospirone or a pharmaceutically acceptable salt thereof is provided as an adhesive formulation.

[Item D15D]

The method of any one of the preceding items, wherein the transdermally administered formulation is a tape/patch.

[Item D16D]

The method of any one of the preceding items, wherein a drug dosage of the tandospirone or a pharmaceutically acceptable salt thereof is 0.1 to 180 mg per day as a free form of tandospirone.

[Item D17D]

The method of any one of the preceding items, wherein an amount of drug penetration for the tandospirone or a pharmaceutically acceptable salt thereof is 0.1 to 20 mg per day as a free form of tandospirone.

[Item D18D]

The method of any one of the preceding items, wherein the tandospirone or a pharmaceutically acceptable salt thereof is provided as a transdermally administered formulation, and a total applied area per dose is 1 to 100 $cm^2$.

[Item D19D]

The method of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item D20D]

The method of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item D21D]

The method of any one of the preceding items, wherein the tandospirone or a pharmaceutically acceptable salt thereof is provided as an adjunct of levodopa.

[Item D22D]
The method of any one of the preceding items, wherein the tandospirone or a pharmaceutically acceptable salt thereof is used with levodopa in the same formulation or concomitantly as separate formulations.

[Item D23D]
A method for treating or preventing Parkinson's disease without accompanying or by minimizing levodopa induced dyskinesia (PD-LID) in a subject, comprising administering an effective amount of a combination of tandospirone or a pharmaceutically acceptable salt thereof and (1) levodopa or (2) levodopa and a metabolizing enzyme inhibitor of levodopa to the subject.

[Item D24D]
The method of any one of the preceding items, wherein the tandospirone or a pharmaceutically acceptable salt thereof and the (1) or (2) are administered simultaneously or at different times.

[Item D25D]
A method for treating or preventing Parkinson's disease without accompanying or by minimizing levodopa induced dyskinesia (PD-LID), comprising administering a combination of an effective amount of tandospirone or a pharmaceutically acceptable salt thereof and an effective amount of (1) levodopa or (2) levodopa and a metabolizing enzyme inhibitor of levodopa.

[Item D26D]
The method of any one of the preceding items, wherein the tandospirone or a pharmaceutically acceptable salt thereof and the (1) or (2) are administered simultaneously or at different times.

[Item D27D]
A method for improving the exacerbation in quality of response to levodopa therapy of a Parkinson's disease patient, comprising administering an effective amount of tandospirone or a pharmaceutically acceptable salt thereof to the Parkinson's disease patient, wherein the improvement comprises an improvement of levodopa induced dyskinesia (PD-LID).

[Item D28D]
The method of any one of the preceding items, wherein the tandospirone or a pharmaceutically acceptable salt thereof is a free form of tandospirone.

[Item E1D]
Use of tandospirone or a pharmaceutically acceptable salt thereof for the manufacture of a medicament for treating, improving, or preventing Parkinson's disease levodopa induced dyskinesia (PD-LID), wherein the use is administration through parenteral administration.

[Item E2D]
The use of item E1D, wherein the parenteral administration is selected from transdermal administration, intradermal administration, subcutaneous administration, intramuscular administration, and a combination thereof.

[Item E3D]
The use of item E1D or E2D, wherein the parenteral administration has sustainability or is sustainably administered.

[Item E4D]
The use of any one of the preceding items, wherein the parenteral administration has a low variation in blood concentration.

[Item E5D]
The use of any one of the preceding items, wherein the parenteral administration comprises transdermal administration.

[Item E6D]
The use of any one of the preceding items, wherein treatment or improvement of the PD-LID improves PD-LID without a rebound symptom.

[Item E7D]
The use of any one of the preceding items, wherein the PD-LID comprises a peak-dose dyskinesia, diphasic dyskinesia, and a combination thereof.

[Item E8D]
The use of any one of the preceding items, wherein treatment, improvement, or prevention of the PD-LID comprises treatment, improvement, or prevention of a PD-LID symptom, reduction of a period of PD-LID manifestation, or a combination thereof.

[Item E9D]
The use of any one of the preceding items, wherein treatment or improvement of the PD-LID is for a clinically significant period or longer.

[Item E10D]
The use of any one of the preceding items, wherein treatment or improvement of the PD-LID is for a sufficient period to attain a clinical effect.

[Item E11D]
The use of any one of the preceding items, wherein treatment or improvement of the PD-LID is a clinically significant improvement or greater.

[Item E12D]
The use of any one of the preceding items, wherein treatment or improvement of the PD-LID is to a sufficient level to attain a clinical effect.

[Item E13D]
The use of any one of the preceding items, wherein the medicament is provided as a transdermally administered formulation.

[Item E14D]
The use of any one of the preceding items, wherein the medicament is provided as an adhesive formulation.

[Item E15D]
The use of any one of the preceding items, wherein the transdermally administered formulation is a tape/patch.

[Item E16D]
The use of any one of the preceding items, wherein a drug dosage of the tandospirone or a pharmaceutically acceptable salt thereof is 0.1 to 180 mg per day as a free form of tandospirone.

[Item E17D]
The use of any one of the preceding items, wherein an amount of drug penetration for the tandospirone or a pharmaceutically acceptable salt thereof is 0.1 to 20 mg per day as a free form of tandospirone.

[Item E18D]
The use of any one of the preceding items, wherein the tandospirone or a pharmaceutically acceptable salt thereof is provided as a transdermally administered formulation, and a total applied area per dose is 1 to 100 cm$^2$.

[Item E19D]
The use of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item E20D]
The use of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item E21D]

The use of any one of the preceding items, wherein the medicament is provided as an adjunct of levodopa.

[Item E22D]

The use of any one of the preceding items, wherein the medicament is used with levodopa in the same formulation or concomitantly as separate formulations.

[Item E23D]

Use of a combination of tandospirone or a pharmaceutically acceptable salt thereof and (1) levodopa or (2) levodopa and a metabolizing enzyme inhibitor of levodopa for the manufacture of a medicament for treating or preventing Parkinson's disease without accompanying or by minimizing levodopa induced dyskinesia (PD-LID).

[Item E24D]

The use of any one of the preceding items, wherein the tandospirone or a pharmaceutically acceptable salt thereof and the (1) or (2) are administered simultaneously or at different times.

[Item E25D]

Use of (1) levodopa or (2) levodopa and a metabolizing enzyme inhibitor of levodopa for the manufacture of a medicament for treating or preventing Parkinson's disease without accompanying or by minimizing levodopa induced dyskinesia (PD-LID), wherein the (1) levodopa or (2) levodopa and a metabolizing enzyme inhibitor of levodopa is administered in combination with tandospirone or a pharmaceutically acceptable salt thereof.

[Item E26D]

The use of any one of the preceding items, wherein the tandospirone or a pharmaceutically acceptable salt thereof and the (1) or (2) are administered simultaneously or at different times.

[Item E27D]

Use of tandospirone or a pharmaceutically acceptable salt thereof for the manufacture of a medicament for improving the exacerbation in quality of response to levodopa therapy of a Parkinson's disease patient, wherein the improvement comprises an improvement of levodopa induced dyskinesia (PD-LID).

[Item E28D]

The use of any one of the preceding items, wherein the tandospirone or a pharmaceutically acceptable salt thereof is a free form of tandospirone.

[Item F1D]

Tandospirone or a pharmaceutically acceptable salt thereof for treating, improving, or preventing Parkinson's disease levodopa induced dyskinesia (PD-LID), wherein the tandospirone or a pharmaceutically acceptable salt thereof is parenterally administered.

[Item F2D]

The tandospirone or a pharmaceutically acceptable salt thereof of item F1D, wherein the parenteral administration is selected from transdermal administration, intradermal administration, subcutaneous administration, intramuscular administration, and a combination thereof.

[Item F3D]

The tandospirone or a pharmaceutically acceptable salt thereof of item F1D or F2D, wherein the parenteral administration has sustainability or is sustainably administered.

[Item F4D]

The tandospirone or a pharmaceutically acceptable salt thereof of any one of the preceding items, wherein the parenteral administration has a low variation in blood concentration.

[Item F5D]

The tandospirone or a pharmaceutically acceptable salt thereof of any one of the preceding items, wherein the parenteral administration comprises transdermal administration.

[Item F6D]

The tandospirone or a pharmaceutically acceptable salt thereof of any one of the preceding items, wherein treatment or improvement of the PD-LID improves PD-LID without a rebound symptom.

[Item F7D]

The tandospirone or a pharmaceutically acceptable salt thereof of any one of the preceding items, wherein the PD-LID comprises peak-dose dyskinesia, diphasic dyskinesia, and a combination thereof

[Item F8D]

The tandospirone or a pharmaceutically acceptable salt thereof of any one of the preceding items, wherein treatment, improvement, or prevention of the PD-LID comprises treatment, improvement, or prevention of a PD-LID symptom, reduction of a period of PD-LID manifestation, or a combination thereof.

[Item F9D]

The tandospirone or a pharmaceutically acceptable salt thereof of any one of the preceding items, wherein treatment or improvement of the PD-LID is for a clinically significant period or longer.

[Item F10D]

The tandospirone or a pharmaceutically acceptable salt thereof of any one of the preceding items, wherein treatment or improvement of the PD-LID is for a sufficient period to attain a clinical effect.

[Item F11D]

The tandospirone or a pharmaceutically acceptable salt thereof of any one of the preceding items, wherein treatment or improvement of the PD-LID is a clinically significant improvement or greater.

[Item F12D]

The tandospirone or a pharmaceutically acceptable salt thereof of any one of the preceding items, wherein treatment or improvement of the PD-LID is to a sufficient level to attain a clinical effect.

[Item F13D]

The tandospirone or a pharmaceutically acceptable salt thereof of any one of the preceding items, wherein the tandospirone or a pharmaceutically acceptable salt thereof is provided as a transdermally administered formulation.

[Item F14D]

The tandospirone or a pharmaceutically acceptable salt thereof of any one of the preceding items, wherein the tandospirone or a pharmaceutically acceptable salt thereof is provided as an adhesive formulation.

[Item F15D]

The tandospirone or a pharmaceutically acceptable salt thereof of any one of the preceding items, wherein the transdermally administered formulation is a tape/patch.

[Item F16D]

The tandospirone or a pharmaceutically acceptable salt thereof of any one of the preceding items, wherein a drug dosage of the tandospirone or a pharmaceutically acceptable salt thereof is 0.1 to 180 mg per day as a free form of tandospirone.

[Item F17D]

The tandospirone or a pharmaceutically acceptable salt thereof of any one of the preceding items, wherein an amount of drug penetration for the tandospirone or a pharmaceutically acceptable salt thereof is 0.1 to 20 mg per day as a free form of tandospirone.

[Item F18D]

The tandospirone or a pharmaceutically acceptable salt thereof of any one of the preceding items, wherein the tandospirone or a pharmaceutically acceptable salt thereof is provided as a transdermally administered formulation, and a total applied area per dose is 1 to 100 cm$^2$.

[Item F19D]

The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 12 hours or longer per day.

[Item F20D]

The tandospirone or a pharmaceutically acceptable salt thereof of any one of the preceding items, wherein the tandospirone or a pharmaceutically acceptable salt thereof is administered so that a human blood (plasma) tandospirone concentration is 0.05 to 20 ng/mL for 8 to 16 hours after administration of the tandospirone or a pharmaceutically acceptable salt thereof.

[Item F21D]

The tandospirone or a pharmaceutically acceptable salt thereof of any one of the preceding items, provided as an adjunct of levodopa.

[Item F22D]

The tandospirone or a pharmaceutically acceptable salt thereof of any one of the preceding items, which is used with levodopa in the same formulation or concomitantly as separate formulations.

[Item F23D]

A combination of (1) levodopa or (2) levodopa and a metabolizing enzyme inhibitor of levodopa for treating or preventing Parkinson's disease without accompanying or by minimizing levodopa induced dyskinesia (PD-LID).

[Item F24D]

The combination of any one of the preceding items, wherein the tandospirone or a pharmaceutically acceptable salt thereof and the (1) or (2) are administered simultaneously or at different times.

[Item F25D]

(1) levodopa or (2) levodopa and a metabolizing enzyme inhibitor of levodopa for treating or preventing Parkinson's disease without accompanying or by minimizing levodopa induced dyskinesia (PD-LID), wherein the (1) levodopa or (2) levodopa and a metabolizing enzyme inhibitor of levodopa is administered in combination with tandospirone or a pharmaceutically acceptable salt thereof.

[Item F26D]

The (1) levodopa or (2) levodopa and a metabolizing enzyme inhibitor of levodopa of any one of the preceding items, wherein the tandospirone or a pharmaceutically acceptable salt thereof and the (1) or (2) are administered simultaneously or at different times.

[Item F27D]

Tandospirone or a pharmaceutically acceptable salt thereof for improving the exacerbation in quality of response to levodopa therapy of a Parkinson's disease patient, wherein the improvement comprises an improvement of levodopa induced dyskinesia (PD-LID).

[Item F28D]

The tandospirone or a pharmaceutically acceptable salt, combination, or (1) levodopa or (2) levodopa and a metabolizing enzyme inhibitor of levodopa of any one of the preceding items, wherein the tandospirone or a pharmaceutically acceptable salt thereof is a free form of tandospirone.

In a specific embodiment, the present disclosure can be provided as an adhesive formulation (also referred to as a tape agent). When the tape agent of the present disclosure is applied, motor complications such as motor fluctuations such as wearing-off, on-off phenomenon, no-on phenomenon, and delayed on phenomenon, and/or dyskinesia including levodopa induced dyskinesia (PD-LID) associated with drug therapy (e.g., levodopa therapy) or the like for Parkinson's disease can be more preferably treated, improved, or prevented, or motor fluctuations can be treated, improved, or prevented without exacerbation of a dyskinesia symptom. By applying a tape agent of the present disclosure in this manner, motor complications in Parkinson's disease can be more preferably treated, improved, or prevented, and motor fluctuations can be treated, improved, or prevented without exacerbating dyskinesia symptoms.

Therapy of Parkinson's disease wherein a single dose and/or a daily dose of an agent such as levodopa is increased, relative to prior to therapy using the tape agent of the present disclosure, without exacerbation of a dyskinesia symptom, can be administered in an actual clinical setting when the tape agent of the present disclosure is applied to more preferably treat, improve, or prevent motor complications associated with drug therapy (e.g., levodopa therapy) for Parkinson's disease or the like.

Current therapy attempts to treat Parkinson's disease patients with small and frequent doses of levodopa to prevent the manifestation of dyskinesia (*Pakinsonbyo Shinryo Gaidorain* 2018 *bajon* [Parkinson's Disease Diagnosis and Treatment Guidelines 2018 version] (Third edition, Q&A for Parkinson's disease diagnosis, Chapter III, Therapy for motor symptoms)), but the present disclosure can also be applied to other cases.

The manifestation of motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID) can be suppressed and the levodopa containing formulation can be adjusted to an optimal dose by administering a parenterally administered formulation of tandospirone provided by the present disclosure. In other words, a more preferred therapy of Parkinson's disease symptoms is enabled without exacerbating motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID), even if a single dose of levodopa is increased to reduce the number of doses or the daily dosage of levodopa is increased for Parkinson's disease patients with or at a risk of manifestation of motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID).

The tandospirone or a pharmaceutically accepted salt or prodrug thereof and therapeutic method of the present disclosure enable treatment, improvement, or prevention to reduce levodopa induced motor complications, especially motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID) involving the normal daily dosage for levodopa therapy specified in *Pakinsonbyo Shinryo Gaidorain* 2018 *bajon* [Parkinson's Disease Diagnosis and Treatment Guidelines 2018 version] published by the Japanese Society of Neurology or a corresponding guideline in the US or Europe.

While existing motor fluctuation improving drugs such as entacapone are known for their risk of inducing a dyskinesia symptom (dyskinesia, which is a dopaminergic side effect), it was found for the first time that the composition of the present disclosure can prolong ON-time (antiparkinsonian action effective time associated with drug therapy such as levodopa therapy for Parkinson's disease) without a dyskinesia symptom.

The inventors have found for the first time that oral administration of tandospirone with expectation of an effect of improving motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID) instead leads to temporary exacerbation of motor complications such as dyskinesia found in Parkinson's disease including drug induced dyskinesia such as levodopa induced dyskinesia (PD-LID). In other words, the inventors have found that oral administration of tandospirone is not preferable as a therapeutic drug for the improvement of motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID) because the oral administration involves a "rebound symptom" of dyskinesia. As used herein, "rebound symptom" is the symptom described infra. Since oral administration of tandospirone results in a "rebound symptom", it is not preferable to increase the dosage of a levodopa containing formulation. "Without exacerbating dyskinesia" in the present disclosure is the state described infra. The present disclosure can improve motor fluctuations such as wearing-off, on-off phenomenon, no-on phenomenon, and delayed on phenomenon without exacerbating dyskinesia.

The inventors have found that the tandospirone parenteral composition of the present disclosure can improve motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID) without a "rebound symptom" of dyskinesia. A score for motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID) can be measured as an "AIMs score" (AIMs is an abbreviation for "abnormal involuntary movements") by the method described herein.

The inventors found that the composition of the present disclosure can be expected to have an effect of treating, improving, or preventing both motor fluctuations and dyskinesia found in Parkinson's disease including drug induced dyskinesia such as levodopa induced dyskinesia (PD-LID). This means that the composition of the present disclosure is an excellent therapeutic drug for motor complications. There is no approved drug that exhibits an effect on both motor fluctuations and dyskinesia found in Parkinson's disease including drug induced dyskinesia such as levodopa induced dyskinesia (PD-LID).

Therefore, the present disclosure, in one example, can be practiced as the following specific embodiments.

(1) A method of treating, improving, or preventing Parkinson's disease, a method of treating, improving, or preventing motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID), or a method of treating, improving, or preventing Parkinson's disease with improved motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID), comprising:

(A) parenterally administering tandospirone; and
(B) administering an increased dosage of levodopa compared to a conventional dosage.

(2) A method of treating, improving, or preventing Parkinson's disease, a method of treating, improving, or preventing motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID), or a method of treating, improving, or preventing Parkinson's disease with improved motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID), comprising:

(A) parenterally administering tandospirone; and
(B) increasing the dosage of levodopa to more than a conventional single dosage to adjust the number of daily dosages.

(3) A method of treating, improving, or preventing Parkinson's disease, a method of treating, improving, or preventing motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID), or a method of treating, improving, or preventing Parkinson's disease with improved motor complications such as motor fluctuations such as wearing-off, on-off phenomenon, no-on phenomenon, and delayed on phenomenon, and levodopa induced dyskinesia (PD-LID) in a patient with or at a risk of manifestation of motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID), comprising:

(A) parenterally administering tandospirone; and
(B) administering levodopa with a maintained or increased dosage.

(4) A method of treating, improving, or preventing Parkinson's disease, a method of treating, improving, or preventing motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID), or a method of treating, improving, or preventing Parkinson's disease with improved motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID) in a patient with or at a risk of manifestation of motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID), comprising:
(A) adding parenteral administration of tandospirone to conventional levodopa therapy; and
(B) increasing a levodopa dosage to the extent that motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID) is not exacerbated and concomitantly using parenteral administration of tandospirone.
(5) A method of treating, improving, or preventing Parkinson's disease, a method of improving dyskinesia, or a method of treating, improving, or preventing Parkinson's disease with improved motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID) comprising:
(A) maintaining a plasma concentration of tandospirone to 0.05 to 20 ng/mL; and
(B) administering levodopa.
(6) A method of treating, improving, or preventing Parkinson's disease, a method of treating, improving, or preventing motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID), or a method of treating, improving, or preventing Parkinson's disease with improved motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID) in a patient with or at a risk of manifestation of motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID), comprising:
(A) maintaining a plasma concentration of tandospirone to 0.05 to 20 ng/mL; and
(B) administering levodopa.

Although not wishing to be bound by any theory, the basis of the efficacy of the present disclosure in motor complications such as motor fluctuations is the following. *Since levodopa has a short half-life and the effect is not sustained, levodopa is generally administered multiple times per day. Meanwhile, the blood concentration of tandospirone is maintained for 24 hours when the tandospirone of the present disclosure is administered as a tape agent, i.e., applied one sheet per day. For this reason, for transdermally administered formulations, levodopa is administered while being exposed to tandospirone no matter at what time levodopa is administered. On the other hand, if a Sediel tablet and levodopa are administered (orally administered) at the same timing three times a day, levodopa would be administered while the blood concentration of tandospirone is reduced. In other words, the feature is in being different from an oral agent. Further, it is preferable that the blood concentration of tandospirone is maintained upon administration of levodopa.

Another aspect provides a composition for treating, improving, or preventing motor fluctuations associated with levodopa therapy for Parkinson's disease, comprising tandospirone or a pharmaceutically acceptable salt thereof, wherein the composition is parenterally administered.

In a specific embodiment, the present disclosure can be used in various applications (indications). For example, indications such as improvement of motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID), treatment of motor complications such as motor fluctuations such as wearing-off, on-off phenomenon, no-on phenomenon, and delayed on phenomenon, and dyskinesia found in Parkinson's disease including drug induced dyskinesia such as levodopa induced dyskinesia (PD-LID) in Parkinson's disease patients treated with levodopa therapy, with or without other medicines that increase the effects of dopamine in the brain, a caution for use or a label (package insert) can be appended.

The present disclosure is intended so that one or more of the aforementioned features can be provided not only as the explicitly disclosed combinations, but also as other combinations. Additional embodiments and advantages of the present disclosure are recognized by those skilled in the art by reading and understanding the following detailed description, as needed.

As used herein, motor complications such as motor fluctuations and dyskinesia refer to symptoms associated with drug therapy such as levodopa therapy for Parkinson's disease or a circumstance equivalent thereto, unless specifically noted otherwise. Such motor complications exclude symptoms that originate from other diseases and are associated with therapy other than drug therapy for Parkinson's disease with levodopa or the like or a circumstance equivalent thereto. In this regard, "symptoms that originate from other diseases and are associated with therapy other than drug therapy for Parkinson's disease with levodopa or the like or a circumstance equivalent thereto" refers to symptoms originating from only a factor other than Parkinson's disease. Thus, it is understood that motor complications such as motor fluctuations and dyskinesia including symptoms originating from Parkinson's disease (coexistence) are within the scope of the present disclosure. It is also understood that the cause and effect relationship of motor complications such as motor fluctuations and dyskinesia with respect to an agent such as levodopa does not need to be proven, and such motor complications are within the scope of the present disclosure as long as they are manifested upon administration of an antiparkinsonian drug such as levodopa or during a period where the effect thereof is understood to remain (e.g., a method of treating dyskinesia in a patient undergoing levodopa therapy is encompassed). Motor complications associated with a neurodegenerative disease similar to Parkinson's disease from dopamine deficiency in the striatum and the like are also encompassed. Examples thereof include multiple system atrophy, progressive supranuclear palsy, corticobasal degeneration, Lewy body dementia, and the like.

Advantageous Effects of Invention

The pharmaceutical composition of the present disclosure has expectation as a therapeutic drug, improving drug, or prophylactic drug for drug induced motor complications such as levodopa induced dyskinesia (PD-LID) in Parkinson's disease (e.g., motor complications such as motor fluctuations such as wearing-off, on-off phenomenon, no-on phenomenon, or delayed on phenomenon, or dyskinesia found in Parkinson's disease including drug induced dyskinesia such as levodopa induced dyskinesia (PD-LID), or the like). The present disclosure also has expectation as a therapeutic drug, improving drug, or prophylactic drug for motor fluctuations without exacerbating a dyskinesia symptom.

The present disclosure also has expectation to reduce wearing-off time without a dyskinesia symptom and/or prolong ON-time without a dyskinesia symptom. The present disclosure also can be expected as therapeutic drug, improving drug, or prophylactic drug for motor complications such as dyskinesia found in Parkinson's disease including drug induced dyskinesia such as levodopa induced dyskinesia (PD-LID) without exacerbating motor fluctuations.

BRIEF DESCRIPTION OF DRAWINGS

FIGS. 5A-5D shows results of measuring dyskinesia-like symptoms and rotational behavior (ON score) for 180 minutes every 20 minutes by administering levodopa to PD-LID rat models by transdermal administration (with stripping condition) of tandospirone. Specifically, a tandospirone tape agent was transdermally administered to a PD-LID rat model on which stratum corneum stripping was performed on the tape agent application site, and levodopa was administered 4 hours later to evaluate dyskinesia-like symptoms (FIG. 5A) and rotational behavior (FIG. 5B). The results are indicated in terms of mean value±standard error. From application of a tandospirone tape agent after stratum corneum stripping, an increase in the total ON score was observed (FIG. 5C), and a significant prolongation in the ON-time without dyskinesia for 180 minutes (Locomotive behavior ≥1, and AIMs score=0) was observed (FIG. 5D).

FIG. 8A shows the total AIMs score in 180 minutes. FIG. 8B shows the total AIMs score in 100 to 180 minutes.

FIG. 9A shows the total AIMs score in 180 minutes. FIG. 9B shows the total AIMs score in 100 to 180 minutes.

FIG. 12A shows the results of repeated administration of levodopa over time, and FIG. 12B shows the results on the day after completion of tandospirone citrate administration (day 16). The test results were statistically analyzed by comparison with the solvent administration group using Steel test with the total AIMs score on day 16 of repeated levodopa administration as the parameter. * indicates $p<0.05$ and ** indicates $p<0.01$, meaning that there is a significant difference compared to the solvent administration group.

FIGS. 20A-20B show results of orally administering levodopa/Benserazide (levodopa at 22 mg/kg, and Benserazide at ¼ the weight of levodopa) to MPTP induced Parkinson's disease levodopa induced dyskinesia (PD-LID) rhesus monkey model and evaluating dyskinesia symptoms every 30 minutes from 5 minutes after administration for 150 minutes. A tandospirone containing paste or a tandospirone free placebo paste was transdermally administered to monkey models. The back of rhesus monkeys was shaved. A paste was applied to a 4 cm×10 cm area 19 hours before the test. The paste was covered with a tape and clean fabric, and the monkeys were fitted with a jacket. Dyskinesia was evaluated by analyzing a video capturing the monkey models and giving scores by an evaluator experienced in behavioral evaluation. Dyskinesia scores were evaluated based on Revised non-human primate dyskinesia rating scale (J Neurosci 2001; 21: 6853-6861.) A score of 0 was given if dyskinesia was not observed at all; a score of 1 was given if dyskinesia was observed in less than 30% of the evaluation period, which is deemed as a mild dyskinesia; a score of 2 was given if dyskinesia was observed in 30% or more of the evaluation period but normal behavior was not inhibited, which is deemed as a moderate dyskinesia; a score of 3 was given if dyskinesia was observed in 30% or more and less than 70% of the evaluation period and normal behavior was inhibited, which is deemed as a significant dyskinesia; and a score of 4 was given if dyskinesia was observed in 70% or more of the evaluation period and normal behavior was inhibited, which is deemed as a severe dyskinesia. Systemic dyskinesia was also evaluated as a particularly severe dyskinesia. Systemic dyskinesia was defined as manifestation of dyskinesia at 4 or more of face, right arm, left arm, body trunk, right leg, and left leg by referring to UDysRS, which is a clinical evaluation scale using dyskinesia by parts in the evaluation. A score of 1 was given if systemic dyskinesia was found in 30% or more of the evaluation period, and a score of 2 was given if systemic dyskinesia was found in 70% or more of the evaluation period.

DESCRIPTION OF EMBODIMENTS

The present disclosure is explained hereinafter while showing the best modes thereof. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present disclosure pertains. In case of a contradiction, the present specification (including the definitions) takes precedence. (Definitions, etc.)

The definitions and/or the basic technology of the terms that are especially used herein are described hereinafter as appropriate.

As used herein, "tandospirone" [Chemical name: (1R,2S, 3R,4S)—N-[4-{4-(pyrimidine-2-yl)piperadine-1-yl}butyl]-2,3-bicyclo[2.2.1]heptanedicarboximide] has the following structure.

[Chemical Formula 1]

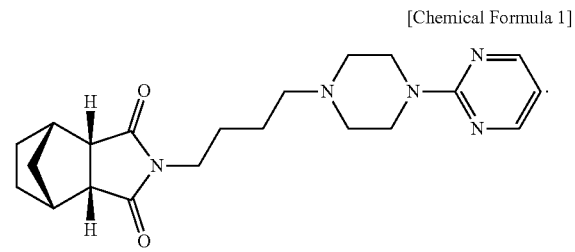 [SMILES: O=C1[C@@H]2[C@@H]3CC[C@@H](C3)[C@@H]2C(=O)N1CCCCN1CCN(c2ncccn2)CC1]

Figure 16:
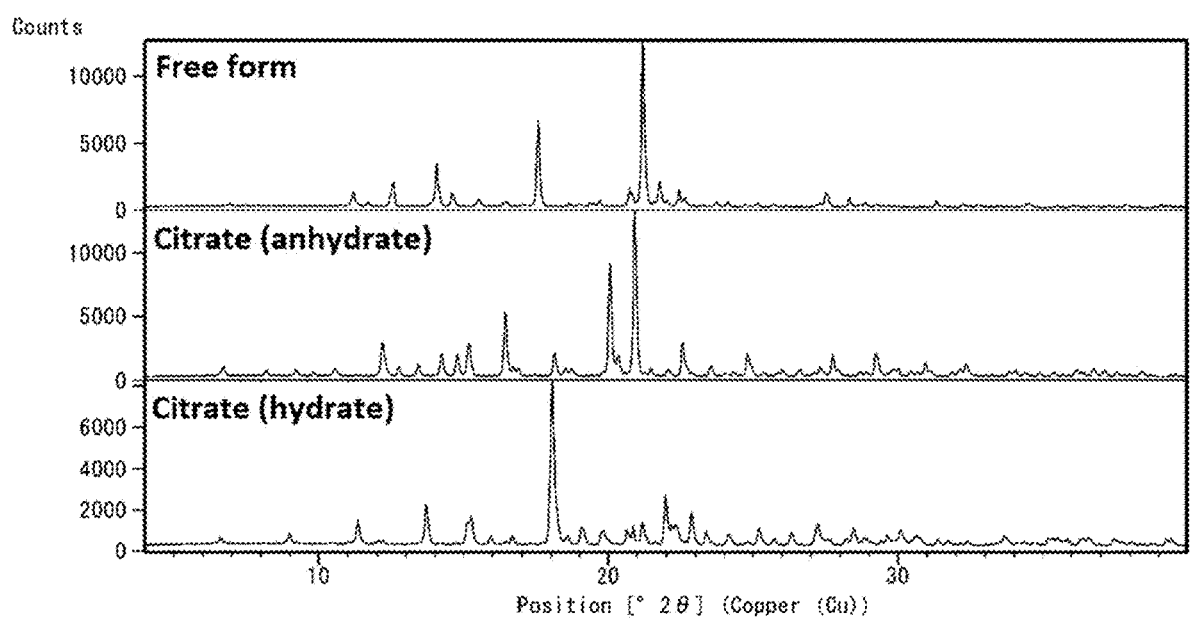
FIG. 16 is a diagram showing X-ray powder diffraction patterns of tandospirone free form, tandospirone citrate (hydrate), and tandospirone citrate (anhydrate).

A Sediel tablet comprising a citric acid salt of tandospirone as an active ingredient is used for therapy as a serotonergic anxiolytic drug (e.g., Sediel package insert or label, revised in April 2016, 14th edition, Sumitomo Dainippon Pharma Co., Ltd.; see Japanese Laid-Open Publication No. 58-126865). Tandospirone has a beneficial effect on memory in chronic schizophrenia. In particular, it is known that cognitive dysfunction can be improved by administering tandospirone or a pharmaceutically acceptable salt thereof while continuing maintenance therapy using a typical antipsychotic such as haloperidol (see Japanese Laid-Open Publication No. 2002-20291; FIG. 16 shows the X-ray powder diffraction pattern).

As an active ingredient used in the pharmaceutical composition of the present disclosure, tandospirone (free form) is preferred, but a pharmaceutically acceptable salt of tandospirone or a prodrug of tandospirone can also be used in the same manner. Pharmaceutically acceptable salts and prodrugs of tandospirone include salts of inorganic acid such as hydrochloride, hydrobromide, sulfate, and phosphate and salts of organic acid such as acetate, butyrate, tartrate, citrate, maleate, and fumarate.

Prodrugs of tandospirone refer to any component, which has a different structure from tandospirone, but can be converted into tandospirone or an active ingredient based thereon by metabolism after administration to exert efficacy.

Prodrugs of tandospirone refer to compounds that are converted to tandospirone due to a reaction with an enzyme, or the like under physiological conditions in the body, i.e., compounds that are changed into tandospirone as a result of enzymatic oxidation, reduction, hydrolysis, or the like. Prodrugs of tandospirone may also be compounds that are changed into tandospirone under physiological conditions such as those described in "Iyakuhin no Kaihatsu" [Drug Development], Hirokawa-Shoten Ltd., 1990, Vol. 7, Molecular Design, pp. 163 to 198.

The tandospirone of the present disclosure or a salt or prodrug thereof (hereinafter, also referred to as tandospirones) has excellent serotonin 5-HT1A receptor activation action.

The tandospirone of the present disclosure has low toxicity and is safe.

A drug with an active ingredient of "tandospirone citrate" is clinically applied as an oral agent as a therapeutic agent for (1) depression or panic in neurosis and (2) physical symptoms, and depression, anxiety, restlessness, or sleep disorder in a psychosomatic disease. Tandospirone is highly selective to serotonin 1A receptors (hereinafter, also referred to as "5-HT1A receptor"), but has low affinity to dopamine 2 receptors (also referred to as "D2 receptor") in in vitro receptor binding evaluation for various neurotransmitter receptors. For this reason, tandospirone is understood as activating a 5-HT1A receptor and selectively acting on serotonin nerves to exert an effect on neurosis or the like.

As used herein, "drug therapy for Parkinson's disease" refers to therapy using a therapeutic drug for Parkinson's disease.

Examples of drug therapy for Parkinson's disease include dopamine replacement therapy (levodopa therapy, drug therapy for Parkinson's disease using a levodopa metabolite inhibitor or dopamine receptor agonist (dopamine agonist), or the like), adjunct agent for Parkinson's disease, and the like. Representative examples of dopamine replacement therapy include levodopa therapy, which includes narrowly defined levodopa therapy (also referred to as therapy using a levodopa containing formulation), drug therapy using a levodopa metabolite inhibitor, and the like.

The pharmaceutical composition of the present disclosure has expectation as a drug for treating, improving, or preventing motor complications of a patient undergoing such drug therapy for Parkinson's disease. In particular, it is known that motor complications tend to manifest in patients undergoing levodopa therapy, so that the pharmaceutical composition of the present disclosure is useful for such patients.

As used herein, "levodopa" (as broadly defined) includes the narrowly defined levodopa (L-3,4-dihydroxyphenylalanine (IUPAC nomenclature is (S)-2-amino-3-(3,4-dihydroxyphenyl)propanoic acid); also called levodopa) as well as any other drugs attaining the same efficacy as L-3,4-dihydroxyphenylalanine. Examples of such other drugs include, but are not limited to, esters of L-3,4-dihydroxyphenylalanine and salts thereof. Examples of esters of L-3,4-dihydroxyphenylalanine include levodopa ethyl ester (LDEE; ethyl(2S)-2-amino-3-(3,4-dihydroxyphenyl)propanoate), levodopa propyl ester; levodopa propyl ester (propyl(2S)-2-amino-3-(3,4-dihydroxyphenyl)propanoate), levodopa methyl ester (methyl(2S)-2-amino-3-(3,4-dihydroxyphenyl)propanoate), and the like. An ester of L-3,4-dihydroxyphenylalanine can be, for example, a salt including hydrated salt. A salt of levodopa ester can include, but is not limited to, one of octanoate, myristate, succinate, succinate dihydrate, fumarate, fumarate dihydrate, mesylate, tartrate, and hydrochloride. Examples of succinate dehydrate or succinate of ester of L-3,4-dihydroxyphenylalanine include levodopa ethyl ester succinate (LDEE-S) and levodopa ethyl ester succinate dehydrate (LDEE-S-dihydrate or LDEE-S(d)).

As used herein, "metabolizing enzyme inhibitor of levodopa" refers to any drug having action to inhibit the metabolism of broadly defined levodopa to enhance the action thereof. Examples thereof include dopa decarboxylase inhibitors (DCI) that prevent levodopa from changing into dopamine in the intestine, liver, or blood vessel (examples thereof include carbidopa, a-methyldopa, benserazide (Ro4-4602), α-difluoromethyl-DOPA (DFMD), salts thereof, and the like), catechol-O-methyl transferase inhibitors (COMT-I) that similarly prevent the decomposition of levodopa before entering the brain (examples thereof include entacapone), monoamine oxidase inhibitors (MAO-I) that prevent the decomposition of dopamine in the brain (examples thereof include selegiline), and the like.

(Disease/Disorder)

As used herein, "motor complications" refer to any motor symptom that is a problem to be treated found in patients with advanced Parkinson's disease. Examples thereof include symptoms such as dyskinesia (levodopa induced dyskinesia (PD-LID)), which is an involuntary movement associated with levodopa therapy, and motor fluctuations such as wearing-off phenomenon, on-off phenomenon, no-on phenomenon, and delayed on phenomenon. ON/OFF is a phenomenon where a symptom drastically changes just like turning a switch on/off. Wearing-off is predictable, whereas ON/OFF is unpredictable. Motor complications are understood to be based on excessive action of levodopa or insufficient levodopa, but the mechanism thereof is not necessarily elucidated (Pakinsonbyo Shinryo Gaidorain 2018 bajon [Parkinson's Disease Diagnosis and Treatment Guidelines 2018 version] (Third edition, Q&A for Parkinson's disease diagnosis, Chapter III, Therapy for motor symptoms)).

"Dyskinesia <involuntary movement>" is a type of motor complication manifested in a patient of Parkinson's disease or the like, referring to movement of hands, legs, or body undulating involuntarily. This includes dyskinesia of patients with a neurodegenerative disease accompanied with dopamine deficiency in the striatum just like Parkinson's disease. It is understood that dyskinesia is caused by various factors. Examples thereof include dyskinesia induced by various agents (e.g., levodopa), dyskinesia manifested upon drug dosing, and the like.

As used herein, "levodopa induced dyskinesia <involuntary movement> (PD-LID)" refers to involuntary movement of the hand, leg, or body unintentionally weaving, which is induced by levodopa overdose. It is known that dyskinesia is readily manifested if a large amount of levodopa is continuously dosed more than necessary from the initial phase of the disease, and it is very difficult to control once it is manifested, even if the dosage of levodopa is subsequently increased or decreased to various levels. Peak-dose dyskinesia is known as an exemplary symptom of PD-LID. The symptom is manifested on the face, tongue, neck, limbs, body trunk, or the like when the blood levodopa concentration is high.

As used herein, "motor fluctuations" refer to reduction in the time during which a drug is effective and loss of an effect until the next dose. This is understood to be due to a decrease in nerve endings retaining dopamine with the progression in Parkinson's disease. Representative motor fluctuations include the wearing-off phenomenon and the like. As used herein, "without" exacerbation in motor fluctuations refers to, for example, a state without exacerbation in wearing-off, on-off phenomenon, no-on phenomenon, and delayed on phenomenon, reduction in ON-time, prolongation of off-time, or the like.

As used herein, "suppression of progression" includes delaying, stopping, or improving (including sensing) progression of motor complications in Parkinson's disease relative to no treatment. Progression of suppression can be determined by confirming an action of prolonging ON-time without dyskinesia in cases of motor complications in Parkinson's disease, but the determination method is not limited thereto. Treatment, prevention, or improvement of the various diseases, disorders, or symptoms in the present disclosure can include suppression of progression of motor complications in Parkinson's disease.

As used herein, "wearing-off" phenomenon" refers to a phenomenon resulting from reduction in the duration of efficacy of levodopa, or a phenomenon wherein the effect of levodopa is lost in some instances. The period of time during which levodopa is effective is referred to as the on-period, and the period of time during which the levodopa effect is lost is referred to as the off-period. On-off phenomenon refers to a symptom suddenly improving (on) or worsening (off) regardless of the period of dosing of levodopa. No-on phenomenon refers to the absence of effect even after dosing of levodopa. A delay on phenomenon refers to manifestation of an effect of levodopa requiring time. "ON-time" which is antiparkinsonian action time, refers to the aggregate time during which levodopa action is observed. In non-clinical settings, ON-time is defined as a period during which levodopa induced rotational behavior is observed in rats treated on one side of the brain with 6-OHDA. Rotational behavior is expressed as the time of rotational behavior, total number of rotational behavior, or the like to the other side of the destruction. This is a behavior reflecting elevated dopamine in the striatum.

Involuntary movement (dyskinesia) refers to a portion of the body moving involuntarily or not stopping, biting of the lips, difficulty in speech, inability to stay still, or difficulty in moving the hand or leg as intended, and is a motor disorder in which involuntary movement is observed in the limbs and/or mouth or face, and/or body axis. Dyskinesia observed in PD patients undergoing therapy with levodopa is known as levodopa induced dyskinesia (LID), which occurs in more than half of PD patients who have had therapy with levodopa for the past 5 to 10 years. The percentage (%) of patients suffering from LID increases with passage of time (for an overview, see, for example, Encarnacion and Hauser, (2008), "Levodopa-induced dyskinesias in Parkinson's disease: etiology, impact on quality of life, and treatments.", Eur Neurol, 60(2), pages 57 to 66). As used herein, no exacerbation of a dyskinesia symptom means, for example, a state with no new manifestation of a dyskinesia symptom, no exacerbation of a dyskinesia symptom, no dyskinesia symptom with a rebound, or the like, relative to before the start of therapy of the present disclosure or no administration of the therapeutic drug of the present disclosure.

Peak-dose dyskinesia is involuntary movement resulting from excessive antiparkinsonian drug. Diphasic dyskinesia is dyskinesia manifested in two phases, i.e., before expression and as of loss of the effect of an antiparkinsonian drug.

If "dyskinesia" in "without dyskinesia", "without exacerbation of dyskinesia", or "without a rebound symptom of dyskinesia" of the present disclosure is levodopa induced peak-dose dyskinesia, this can be confirmed by evaluating the effect of the therapeutic drug/therapeutic method of the invention of the present application during a time frame where the pharmacological action of an antiparkinsonian drug is high. For example, if the dyskinesia is levodopa induced peak-dose dyskinesia, this can be confirmed by evaluating a period from 1 hour to 6 hours after levodopa administration.

ON time without dyskinesia refers to the aggregate time with no dyskinesia during the antiparkinsonian action effective time, i.e., "ON-time". In non-clinical settings, this can be defined as a period during which the dyskinesia symptom (AIMs) score is 0 and the locomotive behavior score is 1 or greater at each evaluation point after levodopa administration in a PD-LID animal model. If there is another similar model, such a model can also be used for evaluation.

As used herein, "pharmaceutically acceptable salt" includes acid and/or base salts formed with inorganic and/or organic acid and base. Examples thereof include acid addition salts and base addition salts. Examples of acid addition salts include inorganic acid salts such as hydrochloride, hydrobromide, sulfate, hydroiodide, nitrate, and phosphate, and organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, and camphorsulfonate. Examples of base addition salts include inorganic base salts such as sodium salt, potassium salt, calcium salt, magnesium salt, barium salt, and aluminum salt, and organic base salts such as trimethylamine, triethylamine, pyridine, picoline, 2,6-lutidine, ethanolamine, diethanolamine, triethanolamine, tromethamine [tris(hydroxymethyl)methylamine], tert-butylamine, cyclohexylamine, dicyclohexylamine, and N—N-dibenzylethylamine. Furthermore, examples of "pharmaceutically acceptable salt" include amino acid salts of a basic or acidic amino acid such as arginine, lysine, ornithine, aspartic acid, and glutamic acid. Pharmaceutically acceptable salts are well known in the art. For example, Berge et al. describes pharmaceutically acceptable salts in detail in J. Pharmaceutical Sciences (1977) 66: 1-19.

A medicament comprising tandospirone or a pharmaceutically acceptable salt or prodrug thereof of the present disclosure can comprise a carrier as needed. As used herein, the term "carrier" refers to a pharmaceutically acceptable substance, composition, or excipient such as a liquid or solid bulking agent, diluent, additive, solvent, base agent, or skin permeation promoting agent, which is associated with or enables the transport or carriage of a target pharmaceutical compound from an organ/tissue of the body or a part thereof to another organ/tissue of the body or a part thereof. "Pharmaceutically acceptable" refers to being compatible with other raw materials in the formulation and being harmless to the subject.

Diseases that are treatable in the present invention include any motor complication in Parkinson's disease.

Treatable diseases in the present disclosure include any levodopa induced motor complications in Parkinson's disease and motor fluctuations associated therewith.

In a specific embodiment, a patient who is treatable in the present disclosure includes Parkinson's disease patients who have or have the potential of manifesting levodopa induced motor complications. Levodopa induced motor complications include levodopa induced dyskinesia.

The effect of improvement on dyskinesia in Parkinson's disease such as levodopa induced dyskinesia in Parkinson's disease in the present invention can be clinically confirmed using a patient diary, a clinical evaluation scale such as Unified Dyskinesia Rating Scale (UDysRS), Clinical Dyskinesia Rating Scale (CDRS), The Rush Dyskinesia Rating Scale (Rush DRS), Movement Disorder Society-Unified Parkinson's Disease Rating Scale (MDS-UPDRS), Abnormal Involuntary Movement Scale (AIMS), EuroQol 5 Dimensions (EQ-5D-5L), PDQ-39 (Parkinson's Disease Questionnarie-39), Clinical Global Impressions (CGI), or Patient Global Impression (PGI), a scale calculated from locomotive movement information obtained from a wearable device such as an accelerometer and/or angular velocimeter, or the like. The effect of improving dyskinesia can also be confirmed by dyskinesia-like abnormal involuntary movement behavior evaluation in a non-clinical model PD-LID rat model. The improvement, suppression of progression, or prevention of levodopa induced dyskinesia (PD-LID) symptoms, as well as reduction in the period of levodopa induced dyskinesia (PD-LID) manifestation can be measured by using this approach.

The action time of an antiparkinsonian therapeutic drug such as levodopa (ON-time) and non-action time of an antiparkinsonian therapeutic drug such as levodopa (OFF-time) in the present disclosure can be clinically assessed through, for example, a clinical evaluation scale such as Unified Parkinson's Disease Rating Scale (UPDRS), MDS-UPDRS, EQ-5D-5L, PDQ-39, CGI, or PGI, a patient diary, a scale calculated from locomotive movement information obtained from a wearable device such as an accelerometer and/or angular velocimeter, or the like. The therapeutic effect with respect to ON-time can be assessed from prolongation in rotational behavior time induced by levodopa in non-clinical rat models treated on one side with 6-OHDA.

In the present disclosure, "rebound symptom" of dyskinesia of a patient with Parkinson's disease or the like is a phenomenon with more exacerbation in dyskinesia than a case without therapy using a dyskinesia improving drug after the peak period (e.g., 1 hour) of antiparkinsonian action of levodopa during therapy using the dyskinesia improving drug. The symptom is anticipated to manifest in 1 to 6 hours after administration of levodopa. In this regard, examples of dyskinesia of a patient with Parkinson's disease or the like include levodopa induced dyskinesia (PD-LID). In the present disclosure, improvement in dyskinesia of a patient with Parkinson's disease or the like (e.g., levodopa induced dyskinesia (PD-LID)) without a rebound symptom can be confirmed by evaluating an effect of the therapeutic drug/therapeutic method of the invention of the present application during a timeframe where the pharmacological action of an antiparkinsonian drug is high. For example, if the dyskinesia is PD-LID or the patient is undergoing levodopa therapy, this is evaluated by an improvement in the total score for dyskinesia without exacerbation of dyskinesia at one point or preferably at a plurality of points in time of evaluation at 1-6 hours after levodopa administration. For example, a rebound symptom of levodopa induced dyskinesia (PD-LID) can be evaluated with clear dyskinesia-like symptoms (AIMs score of 2 or greater) observed at 120 to 140 minutes after levodopa administration, total dyskinesia-like symptom score in 100 to 180 minutes, or the like as an indicator in an AIMs evaluation system of non-clinical PD-LID rat model. Improvement of dyskinesia can be evaluated by a total AIMs score for 180 minutes after levodopa administration.

Whether the ON-time of an antiparkinsonian therapeutic drug (e.g., levodopa) is prolonged without exacerbating dyskinesia of a patient with Parkinson's disease or the like (e.g., PD-LID symptoms) in the present disclosure can be assessed clinically through a clinical evaluation scale such as UPDRS, MDS-UPDRS, UDysRS, CDRS, Rush DRS, AIMS, EQ-5D-5L, PDQ-39, CGI, or PGI, ON-time or OFF-time described in a patient diary, a scale calculated from locomotive movement information obtained from a wearable device such as an accelerometer and/or angular velocimeter, or the like. For example, this can be assessed in a non-clinical PD-LID rat model by evaluating dyskinesia and rotational behavior time.

Whether the ON time without dyskinesia is prolonged in the present disclosure can be assessed clinically through a clinical evaluation scale such as UPDRS, MDS-UPDRS, UDysRS, CDRS, Rush DRS, AIMS, EQ-5D-5L, PDQ-39, CGI, or PGI, ON-time or OFF-time described in a patient diary, a scale calculated from locomotive movement information obtained from a wearable device such as an accelerometer and/or angular velocimeter, or the like. For example, this can be evaluated with a combination of UDysRS and a patient diary. For example, this can be assessed in a non-clinical PD-LID rat model by evaluating rotational behavior time without dyskinesia.

Whether ON-time without troublesome dyskinesia is prolonged in the present disclosure can be assessed clinically through UPDRS, MDS-UPDRS, UDysRS, CDRS, Rush DRS, AIMS, EQ-5D-5L, PDQ-39, CGI, or PGI, ON-time or OFF-time described in a patient diary, a scale calculated from locomotive movement information obtained from a wearable device such as an accelerometer and/or angular velocimeter, or the like in a clinical evaluation scale or a patient diary. For example, this can be evaluated with a combination of UDysRS and a patient diary.

Whether ON-time is prolonged without a rebound symptom of dyskinesia in the present disclosure can be assessed by, for example, comparing the following with a case with no administration of a therapeutic drug of the present disclosure. This can be assessed clinically through UPDRS, MDS-UPDRS, UDysRS, CDRS, Rush DRS, AIMS, EQ-5D-5L, PDQ-39, CGI, or PGI, ON-time or OFF-time described in a patient diary, a scale calculated from locomotive movement information obtained from a wearable device such as an accelerometer and/or angular velocimeter, or the like in a clinical evaluation scale or a patient diary. For example, this can be assessed in a non-clinical PD-LID rat model by evaluating dyskinesia and rotational behavior time. For example, this can be evaluated with a combination of UDysRS and a patient diary.

Motor complications in a motor symptom in the present disclosure can be assessed clinically through UPDRS, MDS-UPDRS, EQ-5D-5L, PDQ-39, CGI, or PGI, ON-time or OFF-time described in a patient diary, a scale calculated from locomotive movement information obtained from a wearable device such as an accelerometer and/or angular velocimeter, or the like in a clinical evaluation scale or a patient diary. If an improvement in a clinical evaluation scale or reduction in OFF-time from a patient diary can be confirmed, motor fluctuations can be deemed improved. A clinical evaluation scale can be evaluated by a method that is known in the art.

In the present disclosure, improvement of motor complications without a rebound symptom of dyskinesia means that the motor complications are improved without exacerbation of dyskinesia, even temporarily, compared to a case without therapy using a motor complication improving drug after levodopa administration.

The inventors found that tandospirone improves motor complications, preferably without exacerbation of dyskinesia. Examples of improvement without exacerbation of dyskinesia include improvement without new manifestation of a dyskinesia symptom, without exacerbation of a clinical score of dyskinesia, without a dyskinesia rebound symptom, and the like. Furthermore, the inventors found that parenteral administration of tandospirone improves motor complications better than oral administration of tandospirone, i.e., has a better effect of prolonging ON-time without dyskinesia. In other words, an effect of prolonging ON-time without dyskinesia was observed in parenteral administration (transdermal administration) regardless of dosage, but for oral administration, prolongation of ON-time without dyskinesia was not observed at normal doses (rats, 10 and 30 mg/kg). ON-time without dyskinesia was prolonged only after increasing the dosage to a dose at which there is a risk of a central nervous system side effect (rat, 100 mg/kg). Those skilled in the art can calculate a suitable dose for humans in light of these doses (see the interview form for Sediel tablets, revised in December 2017, 10th edition, Sumitomo Dainippon Pharma Co., Ltd.). Thus, the therapeutic form can be oral administration of tandospirone, but is preferably parenteral administration, more preferably a sustained parenteral administration or a parenteral administration of a sustained release formulation, and most preferably transdermal administration of tandospirone.

As used herein, levodopa induced "dystonia" is a general term for motor disorders associated with involuntary and sustained muscle contraction due to a central nervous system disorder resulting from levodopa administration, referring to manifestation of symptoms such as postural abnormality, or twisting, stiffness, or spasm in a part of or the entire body. Levodopa induced dystonia can be clinically evaluated through MDS-UPDRS (Part IV), UDysRS, or the like.

As used herein, "adjunct" refers to a drug other than the drug with the primary action. If, for example, levodopa is the primary agent, tandospirone and the like is an adjunct in the present disclosure.

The daily dosage of an antiparkinsonian drug herein is the normal dose for antiparkinsonian drug specified in Pakinsonbyo Shinryo Gaidorain 2018 bajon [Parkinson's Disease Diagnosis and Treatment Guidelines 2018 version] or a corresponding guideline in the US or Europe. The daily dosage of the primary agent levodopa provided as an example herein is the normal dose for levodopa therapy specified in Pakinsonbyo Shinryo Gaidorain 2018 bajon [Parkinson's Disease Diagnosis and Treatment Guidelines 2018 version] or a corresponding guideline in the US or Europe. In general, the normal daily dose of levodopa is 50 to 1200 mg/day and preferably 100 mg to 600 mg/day in concomitant use or as a combined agent with a peripheral dopa decarboxylase inhibitor (DCI). For example, SINEMET® (Carbidopa-Levodopa combination tablet) (New Drug Application (NDA) #017555) approved by the FDA is provided as a 1:4 ratio combination tablet (25 mg Carbidopa—100 mg Levodopa) and 1:10 ratio combination tablet (10 mg Carbidopa—100 mg Levodopa or 25 mg Carbidopa—250 mg Levodopa). The daily maintenance dose of SINEMET® is administered so that Carbidopa would be 70 mg to 100 mg. SINEMET® is administered at the maximum daily dose of up to 200 mg as Carbidopa.

The tandospirone or a pharmaceutically acceptable salt or prodrug thereof or therapeutic method herein can enable therapy to reduce motor complications associated with administration of a normal dose in levodopa therapy or prevention of motor complications.

The levodopa dosage can be appropriately adjusted by administering the tandospirone or a pharmaceutically acceptable salt or prodrug thereof of the present disclosure. The dosage can be increased within the range of the single dosage and daily dosage specified in, for example, Pakinsonbyo Shinryo Gaidorain 2018 bajon [Parkinson's Disease Diagnosis and Treatment Guidelines 2018 version] published by the Japanese Society of Neurology or a corresponding guideline in the US or Europe.

Motor complications can be improved without increasing the dosage of levodopa beyond the normal dose by administering the tandospirone or a pharmaceutically acceptable salt or prodrug thereof of the present disclosure.

As used herein, "has sustainability" can be determined by those skilled in the art by utilizing known findings in the art while considering the descriptions herein. Specifically, having sustainability can be defined as maintaining a blood drug concentration for an extended period of time and exhibiting an effect of prolonged biological half-life. Examples of compositions having sustainability include various transdermally administered formulations described herein, various sustained release injection agents described herein, various implanted agents described herein, and the like. As used herein, "sustainably administered" refers to sustained administration of an active ingredient in the present disclosure from outside to inside the body, which can be achieved through transdermal absorption, injection, infusion, or the like while selecting a parenteral route of administration described herein. Alternatively, "has sustainability" can mean having a low variation in blood concentration of tandospirone. As used herein, "low variation in blood concentration" refers to a ratio of the maximum value (Cmax) to minimum value (Cmin) of tandospirone concentration as of the final administration after reaching a steady state falling within a certain range. The certain range can be appropriately determined by those skilled in the art in accordance with the objective to be achieved (e.g., suppression of motor complications (e.g., suppression of motor fluctuations) or the like) by referring to the disclosures herein. For example, this refers to the ratio of the maximum value (Cmax) to minimum value (Cmin) of tandospirone concentration as of the final administration after reaching a steady state being 1.0 to 3.0, 1.0 to 2.0, 1.0 to 1.8, or 1.0 to 1.7.

As used herein, "clinically significant period" can be determined by those skilled in the art by utilizing known findings in the art while considering the descriptions herein. Specifically, if a significant effect such as prevention, treatment, or alleviation of motor complications targeted by the present disclosure is exhibited, the period of time can be defined as a clinically significant period. For "clinically significant improvement" as used herein, if a significant effect such as prevention, treatment, or alleviation of motor complications targeted by the present disclosure is exhibited, the state can be similarly defined as a clinically significant improvement. The approach to measure such a period or improvement can be appropriately selected by those skilled in the art. For example, any method described herein can be considered. However, the method is not limited thereto. For example, Pakinsonbyo Shinryo Gaidorain 2018 bajon [Parkinson's Disease Diagnosis and Treatment Guidelines 2018 version] published by the Japanese Society of Neurology can also be used. Alternatively, it is reported that the dyskinesia clinical evaluation index (MDS UDysRS Part III) is 2.32 points (Parkinsonism Relat Disord 21: 1349, 2015)). The method can be appropriately determined by considering (1) comparison with a placebo, (2) before and after therapy for each patient, or the like.

As used herein, "sustainably maintain a dopamine level in a striatum synaptic cleft" means that the dopamine level in the striatum synaptic cleft is maintained at a certain concentration or higher. This can be confirmed herein by, for example, a PET test under the conditions described in the aforementioned reference document or the like. The effect of a pharmaceutical composition can be confirmed herein from the amount of change 1 h/4 h in the amount of striatal $[^{11}C]$ raclopride receptor binding of less than 5% and/or the ratio of change 1 h/4 h in the amount of striatal $[^{11}C]$, raclopride receptor binding of 90% or less, preferably 80% or less, and more preferably 70% or less, or the like. As used herein, the amount of change in striatal $[^{11}C]$ raclopride receptor binding from before levodopa administration to 1 hour after administration is referred to as the amount of change B/1 h.

As used herein, "suppress a rapid change in a dopamine level in a striatum synaptic cleft" means that the dopamine level in the striatum synaptic cleft does not change significantly in a short period of time. This can be confirmed by, for example, a PET test under the conditions described in the aforementioned reference document or the like. The effect of the pharmaceutical composition of the invention can be confirmed from the amount of change B/1 h in the amount of striatal $[^{11}C]$ raclopride receptor binding of less than 10% and/or the ratio of change B/1 h of 90% or less, preferably 80% or less, and more preferably 70% or less, or the like.

As used herein, "suppress intermittent domain receptor stimulation" means to suppress an increase/decrease of the dopamine level in the striatum synaptic cleft over time. This can be confirmed by, for example, a PET test under the conditions described in the aforementioned reference document or the like. The effect of the pharmaceutical composition of the invention can be confirmed from whether the difference between the amount of change B/1 h and the amount of change B/4 h in striatal raclopride receptor binding is reduced or the like.

As used herein, "sufficient period to attain a clinical effect" and "sufficient level to attain a clinical effect" can also be determined by those skilled in the art by utilizing known findings in the art while considering the descriptions herein. Specifically, if the period or level that can attain a clinical effect such as prevention, therapy, or alleviation of motor complications targeted by the present disclosure can be measured, the period or level can be evaluated as a sufficient period to attain a clinical effect. An approach of measuring such a period or level can be appropriately selected by those skilled in the art. For example, any method described herein can be considered. However, the method is not limited thereto. For example, Pakinsonbyo Shinryo Gaidorain 2018 bajon [Parkinson's Disease Diagnosis and Treatment Guidelines 2018 version] published by the Japanese Society of Neurology or a corresponding guideline in the US or Europe can also be used.

As used herein, "no" "exacerbation of a dyskinesia symptom (e.g., levodopa induced dyskinesia (PD-LID) symptom) in a Parkinson's disease patient" means that an already developed dyskinesia symptom is not exacerbated to a clinically significant degree or is not significantly exacerbated, dyskinesia manifestation period is not prolonged, a symptom is not significantly exacerbated, even temporarily, as in a rebound symptom of dyskinesia, a dyskinesia is not newly developed, or the frequency of side effects in dyskinesia does not increase significantly relative to a case without administration of the composition of the invention. A dyskinesia symptom can be confirmed, for example, through a clinical evaluation score such as UPDRS, MDS-UPDRS, UDysRS, CDRS, Rush DRS, AIMS, EQ-5D-5L, PDQ-39, CGI, or PGI, ON time or OFF time described in a patient diary, a scale calculated from locomotive movement information obtained from a wearable device such as an accelerometer and/or angular velocimeter, or the like.

As used herein, "exacerbation in quality of response to levodopa therapy of a Parkinson's disease patient" refers to any decrease in responsiveness of a patient to levodopa therapy. Such an exacerbation in the quality of response can be measured from motor fluctuations, a dyskinesia symptom, or the like. "Improvement" of "exacerbation in quality of response to levodopa therapy of a Parkinson's disease patient" refers to improvement in the degree of dyskinesia symptom or motor fluctuations in levodopa therapy of each patient. The improvement can be confirmed by evaluating a clinical evaluation scale such as UPDRS, MDS-UPDRS, UDysRS, CDRS, Rush DRS, AIMS, EQ-5D-5L, PDQ-39, CGI, or PGI, ON time or OFF time described in a patient diary, a scale calculated from locomotive movement information obtained from a wearable device such as an accelerometer and/or angular velocimeter, or the like.

As used herein, "parenteral administration" refers to a dosage form for any route that is not oral administration. Preferably, any mode for administering tandospirone in a mode and level that are effective for drug induced motor complications such as levodopa induced motor complications in Parkinson's disease is employed. Examples of means of parenteral administration include administration through transdermal absorption or transmucosal absorption, as well as injection, infusion, and combinations thereof. For example, administration through transdermal absorption or transmucosal absorption exerts an effect by contacting a transdermally administered formulation such as a paste agent, adhesive formulation, or spray to the skin or mucous membrane so that a drug in the formulation migrates into the body through the skin or mucous membrane. Examples of administration via injection or infusion include intravenous, intradermal, subcutaneous, intramuscular, and enteral administration (intestinal infusion), which can also be administered as a bolus and/or sustained infusion. Injection or infusion can use a suspension, liquid agent, emulsion, or implanted agent in an oily or aqueous medium, comprising another formulation substance such as a suspending agent, stabilizer, and/or a dispersant. Enteral administration (intestinal infusion) can provide sustained drug delivery to the proximal small intestine by using a tube or portable infusion pump by percutaneous endoscopic gastrostomy. In a preferred embodiment, parenteral administration can be performed in a form of a sustained administration. Such sustained administration can be accomplished with transdermal patch/tape or the like, injection, infusion, or the like.

In the present disclosure, tandospirone or a pharmaceutically acceptable salt or prodrug thereof is preferably administered by a method that can maintain blood drug concentration for a long period of time, and is more preferably administered by a method that can suppress the generation of metabolites. Examples of administration methods include transdermal administration and injection such as subcutaneous, intradermal, and intramuscular administrations. Injection such as subcutaneous, intradermal, and intramuscular administrations is preferably a method of administration that sustains the blood concentration. In particular, transdermal administration is the most preferred because it is an administration method that has a low degree of invasiveness and requires no hospital visits.

In the present disclosure, treatment, improvement, or prevention of motor complications associated with levodopa therapy for Parkinson's disease by parenteral administration of tandospirone or a pharmaceutically acceptable salt or prodrug thereof, or a medicament or composition comprising the same is preferred compared to therapy using an active ingredient other than the present disclosure or therapeutic methods and compositions other than the present disclosure from the viewpoint of having no adverse effect on levodopa action time (ON-time), having no adverse effect on parkinsonian symptoms (can be evaluated by UPDRS or the like), having no attenuation in the effect of the present disclosure in repeated administration, capability to reduce the number of doses of levodopa formulations per day by increasing a levodopa formulation to the optimal dose without exacerbating motor complications, and the like.

The present disclosure provides a composition or a medicament for treating, improving, or preventing motor fluctuations in Parkinson's disease, comprising tandospirone or a pharmaceutically acceptable salt or prodrug thereof, and a method for treating or preventing the same. Motor fluctuations in Parkinson's disease has become a problem. Although not intended as a limitation, such motor fluctuations may be manifested in association with drug therapy for Parkinson's disease such as levodopa therapy. In the present disclosure, the inventors unexpectedly found that tandospirone or a pharmaceutically acceptable salt or prodrug thereof can suppress or eliminate motor fluctuations in Parkinson's disease. Furthermore, the inventors found that parenteral administration has an effect of prolonging ON-time without dyskinesia and a clinically significant, more preferred effect of improving motor complications. It was unexpected from conventional findings that parenteral administration of tandospirone would exert an effect of prolonging ON-time without dyskinesia. Specifically, an agent that suppresses or eliminates motor fluctuations is generally expected to have a pharmacological action of increasing the amount of dopamine, i.e., the agent is expected to be associated with exacerbation of dyskinesia.

It was found that the present disclosure can also treat, improve, or prevent motor fluctuations such as wearing-off, on-off phenomenon, no-on phenomenon, and delayed on phenomenon and treat, improve, or prevent dyskinesia in Parkinson's disease such as levodopa induced dyskinesia (PD-LID). Since PD-LID, which is a representative example of dyskinesia, is induced by excessive administration of levodopa, it is understood that suppression of the intracranial dopamine concentration is effective, while it is understood that increasing the intracranial dopamine concentration is effective for suppressing motor fluctuations by prolonging ON-time, reducing OFF-time, or the like. For this reason, it was not expected from conventional findings that the composition of the present disclosure can treat, improve, or prevent dyskinesia in Parkinson's disease such as levodopa induced dyskinesia (PD-LID) while treating, improving, or preventing motor fluctuations during the same period.

"Transdermally administered formulation" refers to a paste agent, adhesive formulation, or spray (aerosol). Specific examples of adhesive formulations include tape agents (transdermal patch), poultice, plaster, and the like, and examples of paste agents include ointment, cream, lotion, liniment, liquid agent, gel, and the like. A transdermally administered formulation is preferably an adhesive formulation and more preferably a tape agent (transdermal patch). Since a "tape agent" is synonymous with a "patch" in the present disclosure, they are also denoted as "tape/patch" herein.

A transdermally administered formulation is manufactured by a known method using a pharmaceutically acceptable additive. In one embodiment, a transdermally administered formulation used in the present disclosure has an adhesive layer provided on a support, and the adhesive layer can be manufactured by including a thermoplastic elastomer or the like. A "thermoplastic elastomer" is an elastomer that softens and exhibits fluidity when heated, and exhibits thermoplasticity of returning to a rubber-like elastic when cooled. Examples thereof include various thermoplastic elastomers such as urethane, acrylic, styrene, and olefin based elastomers.

For the transdermally administered formulation of the present disclosure, an adhesive layer can comprise nonvolatile hydrocarbon oil. As nonvolatile hydrocarbon oil, a chained saturated hydrocarbon with about 20 to 40 carbons or chained unsaturated hydrocarbon with about 20 to 40 carbons is preferable. Examples thereof include liquid paraffin, squalene, squalane, pristane, and the like. In particular, liquid paraffin is more preferable from the viewpoint of availability. Liquid paraffin is a mixture of colorless, odorless liquid alkanes with 20 or more carbons. In the present disclosure, liquid paraffin that is in compliance with the specification specified in the Japanese Pharmacopoeia, US Pharmacopoeia, or the like can be preferably used. Nonvolatile hydrocarbon oil with high viscosity is preferred. Use of liquid paraffin with high viscosity is especially preferable from the viewpoint of adhesiveness.

An adhesive layer can also comprise a tackifier as needed. A tackifier is generally a resin that is commonly used for imparting skin adhesiveness in the art of adhesive formulations. Examples thereof include rosin based resin, polyterpene resin, coumarone-indene resin, petroleum-based resin, terpene-phenol resin, alicyclic saturated hydrocarbon resin, and the like. One or more thereof can be selected therefrom and used.

If transdermal administration is envisioned, this can also be materialized by applying an ointment to the skin.

A dosage form for parenteral administration (e.g., transdermal administration) of the tandospirone or a pharmaceutically acceptable salt or prodrug thereof disclosed herein, other than a tape/patch, can include powder, spray, ointment, paste, cream, lotion, gel, and liquid solution.

Ointment, paste, cream, and gel can comprise, in addition to the tandospirone or a pharmaceutically acceptable salt or prodrug thereof disclosed herein, an additive such as animal and plant fat, oil, wax, paraffin, starch, tragacanth, cellulose derivative, polyethylene glycol, silicone, bentonite, silicic acid, talc, or zinc oxide, or a mixture thereof.

Powder and spray can comprise, in addition to the pharmaceutical composition disclosed herein, an additive such as lactose, talc, silicic acid, aluminum hydroxide, calcium silicate, or polyamide powder or a mixture thereof. A spray can further comprise a common high pressure gas such as chlorofluorohydrocarbon or volatile unsubstituted hydrocarbon such as butane or propane.

In addition to ointment, powder, solution, and the like are also understood to be within the scope of the disclosure herein, as long as it is suitable for parenteral administration.

A composition suitable for parenteral administration can comprise at least one type of pharmaceutically acceptable aseptic isotonic aqueous or non-aqueous solution, dispersion, suspension, emulsion, implanted agent, or aseptic powder that can be reconstituted into an aseptic injection solution or dispersion immediately before use.

The composition disclosed herein can be prepared as a suppository for rectal or vaginal administration. The composition can be prepared by mixing one or more compounds according to the disclosure herein with one or more suitable non-stimulatory additives or carriers including cocoa butter, polyethylene glycol, suppository wax, salicylate, or the like. The composition is a solid at room temperature, but is a liquid at body temperature. Thus, the composition melts in the rectum or the vaginal cavity to release the compound in the disclosure herein. A pharmaceutical composition suitable for vaginal administration can include a pessary, tampon, cream, gel, paste, foam, or spray formulation comprising a carrier known to be suitable in prior art.

As used herein, "drug dosage" is the amount of drug contained in a composition. Drug dosage is described as the active ingredient content on a label (package insert). As used herein, "amount of drug penetration" is the amount of drug intake into the body. If a composition is a transdermally administered formulation, "amount of drug penetration" is the amount of drug that has absorbed into the skin from the transdermally administered formulation, and is a value calculated by the following equation. The amount of drug penetration is related to drug efficacy. If the dosage is assumed to be 100%, the amount of penetration is often, but is not limited to, 40 to 50% in results of clinical formulations. "Amount of residual drug" is the amount of drug remaining in the transdermally administered formulation that has been peeled off after application. This amount can be quantified by the method described in the Examples (Reference Manufacturing Example) or the like.

Amount of drug penetration (mg/day)=drug dosage (mg/day)−amount of residual drug (mg/day)

For formulations other than transdermally administered formulations such as oral formulations or injections, the entire amount of the formulation itself is administered to the body, so that the drug dosage and amount of drug penetration are generally understood to be substantially the same. Thus, for oral formulations, "taken up into the body" refers to providing the formulation into the digestive track. If the drug dosage and the amount of drug penetration are different in transdermally administered formulations, this can be identified, for a tape agent, by measuring the residual amount in the tape after peeling off.

In the present disclosure, the drug dosage, amount of drug penetration, amount of residual drug, and blood (plasma) tandospirone concentration are amounts converted in terms of tandospirone free form, unless specifically noted otherwise.

In the present disclosure, the dosage or amount of penetration of tandospirone or a salt thereof can be appropriately adjusted depending on the type of compound, symptom/age/body weight/kidney or liver function of the patient, or the like. For example, the daily drug dosage is 0.1 to 500 mg, 0.1 to 400 mg, 0.1 to 250 mg, 0.1 to 220 mg, 0.1 to 180 mg, or 0.1 to 100 mg, and preferably 0.2 to 50 mg, 1 to 50 mg, 4 to 180 mg, 1 to 250 mg, 3 to 250 mg, or the like. Examples of the upper limit thereof include 1000 mg, 800 mg, 500 mg, 400 mg, 250 mg, 220 mg, 180 mg, 150 mg, 100 mg, 80 mg, 50 mg, 30 mg, 15 mg, and the like. Examples of lower limit include 0.1 mg, 0.2 mg, 1 mg, 2 mg, 3 mg, 4 mg, 10 mg, 15 mg, and the like. Examples of a preferred range include any combination of these upper limits and lower limits. The daily amount of drug penetration can be 0.1 to 100 mg, 0.1 to 80 mg, 0.1 to 60 mg, or 0.1 to 20 mg, preferably 0.2 to 10 mg, 1 to 60 mg. Examples of the upper limit thereof include 100 mg, 80 mg, 60 mg, 40 mg, 30 mg, 20 mg, 10 mg, 8 mg, 7 mg, 5 mg, 3 mg, and the like. Examples of the lower limit include 0.1 mg, 0.2 mg, 1 mg, 1.5 mg, 3 mg, and the like. Examples of a preferred range include any combination of these upper limits and lower limits. The dosing frequency can be appropriately adjusted depending on the property of the composition. If the composition is a transdermally administered formulation, the frequency is for example once every 12 hours to once every 7 days. Any frequency therebetween can also be selected, such as once daily, once every 2 days, once every 3 days, once every 4 days, or the like. The frequency is preferably once a day. If the composition is an injection formulation, the frequency is, for example, once daily to once every 3 months. Any frequency therebetween can be selected, such as once a week, once every two weeks, once every 4 weeks, once every 3 months, or the like. It is also possible to adjust the dosing time depending on the symptom with a pump-style automatic injector for sustained administration for 24 hours, or for administration only when the patient is awake. In a preferred example, the agent can be mixed with a formulation comprising levodopa and sustainably administered.

In the present disclosure, tandospirone or a pharmaceutically acceptable salt or prodrug thereof is preferably administered so that the human blood (plasma) tandospirone concentration is 0.05 to 20 ng/mL as the amount converted in terms of a free form in a period during which levodopa is desired to be active. Specifically, the period is 12 hours or longer, preferably 16 hours or longer per day.

Examples of the human blood (plasma) tandospirone concentration include 0.05 to 20 ng/mL, 0.1 to 10 ng/mL, 0.5 to 15 ng/mL, 0.5 to 12 ng/mL, 0.1 to 15 ng/mL, 1 to 15 ng/mL, 1 to 12 ng/mL, 2 to 10 ng/mL, and the like as an amount converted in terms of free form. Examples of the upper limit thereof include 20 ng/mL, 15 ng/mL, 12 ng/mL, 10 ng/mL, 8 ng/mL, 5 ng/mL, 4 ng/mL, 3 ng/mL, 2 ng/mL, 1 ng/mL, and the like. Examples of the lower limit include 0.01 ng/mL, 0.02 ng/mL, 0.05 ng/mL, 0.1 ng/mL, 0.2 ng/mL, 0.5 ng/mL, 1 ng/mL, 2 ng/mL, and the like. Examples of a preferred range include any combination of these upper limits and lower limits. The aforementioned human blood (plasma) tandospirone concentration can be attained with a single administration or as a maintenance concentration by repeated administration.

In the present disclosure, examples of the maximum value (Cmax) of human blood (plasma) tandospirone concentration include 0.1 to 20 ng/mL, 0.2 to 15 ng/mL, 0.3 to 12 ng/mL, 0.3 to 10 ng/mL, 1 to 15 ng/mL, 1 to 12 ng/mL, 1 to 10 ng/mL, 2 to 10 ng/mL, and the like as an amount converted in terms of free form. Examples of the upper limit thereof include 20 ng/mL, 15 ng/mL, 12 ng/mL, 10 ng/mL, 8 ng/mL, 5 ng/mL, 4 ng/mL, 3 ng/mL, 2 ng/mL, 1 ng/mL, and the like. Examples of the lower limit include 0.1 ng/mL, 0.2 ng/mL, 0.5 ng/mL, 1 ng/mL, 2 ng/mL, and the like. Examples of a preferred range include any combination of these upper limits and lower limits.

In the present disclosure, examples of the area under the human blood (plasma) tandospirone concentration-time curve (AUC) include 3 to 700 ng·h/mL, 3 to 500 ng·h/mL, 3 to 300 ng·h/mL, 3 to 250 ng·h/mL, 3 to 200 ng·h/mL, and the like as an amount converted in terms of free form. Examples of the upper limit thereof include 700 ng·h/mL, 600 ng·h/mL, 500 ng·h/mL, 400 ng·h/mL, 300 ng·h/mL, 200 ng·h/mL, 150 ng·h/mL, 50 ng·h/mL, 100 ng·h/mL, 80 ng·h/mL, 50 ng·h/mL, 40 ng·h/mL, and the like. Examples of the lower limit include 3 ng·h/mL, 5 ng·h/mL, 10 ng·h/mL, 20 ng·h/mL, 30 ng·h/mL, and the like. Examples of a preferred range include any combination of these upper limits and lower limits. The area under the tandospirone concentration-time curve (AUC) can be calculated by a method of analyzing pharmacokinetics. For example, a value from 0 to 48 hours, 0 to 72 hours, or 0 to the time of final measurement, or a value extrapolated to an infinite is calculated.

In the present disclosure, a composition comprising tandospirone or a pharmaceutically acceptable salt or prodrug thereof is a composition characterized by being administered so that the human blood (plasma) tandospirone concentration is a concentration described above as a human blood (plasma) tandospirone concentration such as 0.05 to 20 ng/mL, 0.1 to 15 ng/mL, 0.1 to 10 ng/mL, 0.5 to 15 ng/mL, 0.5 to 12 ng/mL, 1 to 15 ng/mL, 1 to 12 ng/mL, or 2 to 10 ng/mL for 8 to 16 hours, more preferably 8 to 20 hours after administration of the tandospirone or a pharmaceutically acceptable salt or prodrug thereof, or for 12 hours or longer, preferably 16 hours or longer, and more preferably 18 hours or longer per day. The human blood (plasma) tandospirone concentration described above can be achieved with a single administration, or achieved as a concentration maintained by repeated administration (also considered as a steady state). The blood concentration in a steady state can be calculated by a method stacking single administrations. For concentration maintained by repeated administration (steady state), the time after administration refers to the time after the last administration.

Tandospirone or a pharmaceutically acceptable salt thereof is administered herein so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% and preferably 35 to 85% after administration of the tandospirone or a pharmaceutically acceptable salt thereof.

In the present disclosure, if the composition comprising tandospirone or a pharmaceutically acceptable salt or prodrug thereof is a transdermally administered formulation, the formulation application area thereof can generally be adjusted when appropriate, but the total application area per dose is preferably 1 to 200 cm$^2$, 1 to 100 cm$^2$, 2 to 80 cm$^2$, or 9 to 60 cm$^2$. Examples of the upper limit thereof include 200 cm$^2$, 160 cm$^2$, 130 cm$^2$, 100 cm$^2$, 80 cm$^2$, 60 cm$^2$, 50 cm$^2$, 40 cm$^2$, 30 cm$^2$, 20 cm$^2$, and the like. Examples of the lower limit include 1 cm$^2$, 2 cm$^2$, 4 cm$^2$, 9 cm$^2$, and the like. Examples of a preferred range include any combination of these upper limits and lower limits, which enables a preferred therapeutic effect to be attained.

The tandospirone or a pharmaceutically acceptable salt or prodrug thereof of the present disclosure exceeds the lower limit value of the human blood (plasma) tandospirone concentration within 12 hours or 8 hours, preferably within 6 hours, and more preferably within 4 hours after a single dose, and the human blood (plasma) tandospirone concentration is maintained in the range between the upper limit and the lower limit for up to 16 hours, preferably up to 18 hours, and more preferably up to 20 hours or 24 hours after the single dose.

The tandospirone or a pharmaceutically acceptable salt or prodrug thereof of the present disclosure preferably has a pharmacokinetic profile of reaching the maximum blood concentration (Cmax) more gradually and being eliminated more gradually relative to oral administration.

The time to reach the maximum blood concentration (Cmax) (mean value) is, for example, between 16 hours and 36 hours or between 20 hours and 32 hours after a single dose. Examples of the lower limit for the time to reach the maximum blood concentration (Cmax) (mean value) include 16 hours, 20 hours, and 24 hours. Examples of the upper limit (mean value) include 36 hours and 32 hours. The half-life (mean value) is, for example, between 3 and 20 hours. Examples of the lower limit for the half-life (mean value) include 3 hours, 4 hours, 5 hours, 6 hours, and the like. Examples of the upper limit (mean value) include 20 hours, 18 hours, 16 hours, 14 hours, and the like.

The following protocol described in a reference document (J Clin Invest. (2014) 124(3):1340-1349.) can be referred to as a suitable clinical evaluation that can confirm the efficacy of the pharmaceutical composition of the invention on dyskinesia in Parkinson's disease. Specifically, brain function image analysis using positron emission tomography (PET) of striatal dopamine D2 receptor is performed on patients with a dyskinesia symptom. This can be utilized in estimating the degree of progression of pathological condition or the effective drug concentration or determining the therapeutic effect.

For example, [$^{11}$C] raclopride can be used as a PET tracer of a dopamine D2 receptor expressed in the striatal dopamine nerve post synapse. The amount of change in released dopamine in the striatum can be evaluated by measuring the amount of change in striatal [$^{11}$C] raclopride binding relative to a baseline (OFF state) from levodopa administration or concomitant use of the pharmaceutical composition of the invention with levodopa administration by [$^{11}$C] raclopride PET It has been reported that the amount of change in striatal [$^{11}$C] raclopride receptor binding in Parkinson's disease is related to progression in the pathological state of Parkinson's disease, motor fluctuations, or dyskinesia (reference document: Brain. (2004) 127:2747-2754.)

The result of evaluating the striatal dopamine level under the conditions for the PET test in the aforementioned reference document can be understood as follows.

For example, it is known that the "amount of change in striatal [$^{11}$C] raclopride receptor binding from before levodopa administration to 1 hour after administration (also abbreviated as the amount of change B/1 h)" is higher in Parkinson's disease patients with motor fluctuations or dyskinesia compared to patients without motor fluctuations or dyskinesia, such as by 10% or greater or 15% or greater. If the amount of change B/1 h decreases due to drug therapy, this means that the therapy is effective on motor complications such as dyskinesia. The pharmaceutical composition of the invention is expected to reduce the amount of change B/1 h. In particular, the amount of change B/1 h is reduced in Parkinson's disease patients who have a significantly higher amount of change B/1 h than patients without motor fluctuations or dyskinesia. The composition is also expected to have a therapeutic effect on motor complications such as dyskinesia. Therapy with the pharmaceutical composition of the invention is expected to reduce the amount of change B/1 h to, for example, less than 10%.

For example, it is known that the absolute value of the "amount of change in striatal [$^{11}$C] raclopride receptor binding from 1 hour after levodopa administration to 4 hours after administration (also abbreviated as the amount of change 1 h/4 h)" is higher in Parkinson's disease patients with motor fluctuations or dyskinesia compared to patients without motor fluctuations or dyskinesia, such as by 5% or greater. If the amount of change B/1 h decreases due to drug therapy, this means that the therapy is effective on motor complications such as motor fluctuations. The pharmaceutical composition of the invention is expected to reduce the amount of change B/1 h. In particular, the amount of change 1 h/4 h is reduced in Parkinson's disease patients with motor fluctuations or dyskinesia who have a significantly higher amount of change B/1 h than patients without motor fluctuations or dyskinesia. The composition is also expected to have a therapeutic effect on motor complications such as motor fluctuations. Therapy with the pharmaceutical composition of the invention is expected to reduce the amount of change 1 h/4 h to, for example, less than 5%.

For example, a decrease in the "ratio of amount of change in striatal [$^{11}$C] raclopride receptor binding from before levodopa administration to 1 hour after administration after therapeutic intervention with the pharmaceutical composition of the invention (also abbreviated as the amount of change B/1 h after therapy) with respect to the amount of change in striatal [$^{11}$C] raclopride receptor binding from before levodopa administration to 1 hour after administration before therapy with the composition of the invention (also abbreviated as the amount of change B/1 h before therapy)" when this is 100% (also abbreviated as the ratio of change B/1 h) means that therapy is effective on motor complications such as dyskinesia. The pharmaceutical composition of the invention is expected to reduce the ratio of change B/1 h, and can reduce the ratio of change B/1 h to, for example, 90% or less, preferably 80% or less, and more preferably 70% or less upon a PET test under the conditions reported in a document.

For example, a decrease in the "ratio of amount of change in striatal [$^{11}$C] raclopride receptor binding from 1 hour after levodopa administration to 4 hours after administration after therapeutic intervention with the pharmaceutical composition of the invention (also abbreviated as the amount of change 1 h/4 h after therapy) with respect to the amount of change in striatal [$^{11}$C] raclopride receptor binding from 1 hour after levodopa administration to 4 hours after administration before therapy with the composition of the invention (also abbreviated as the amount of change 1 h/4 h before therapy) (also abbreviated as the ratio of change 1 h/4 h)" in a Parkinson's disease patient with motor fluctuations or dyskinesia means that therapy is effective on motor complications such as motor fluctuations. The pharmaceutical composition of the invention is expected to reduce the ratio of change 1 h/4 h, and can reduce the ratio of change 1 h/4 h to, for example, 90% or less, preferably 80% or less, and more preferably 70% or less upon a PET test under the conditions reported in a document.

As the measurement point before levodopa administration, the amount can be measured at a time at which sufficient time has passed after levodopa administration and an effect of levodopa is not found.

As the measurement point at 1 hour after administration, the amount can be measured at a determined time at 1 to 2 hours after levodopa administration.

As the measurement point at 4 hours after administration, the amount can be measured at a determined time at 4 to 8 hours after levodopa administration.

For the amount of striatal [$^{11}$C] raclopride receptor binding,
Amount of change B/1 h (%)=(amount of receptor binding before levodopa administration−amount of receptor binding 1 hour after levodopa administration)÷amount of receptor binding before levodopa administration×100

Amount of change B/4 h (%)=(amount of receptor binding before levodopa administration−amount of receptor binding 4 hours after levodopa administration) amount of receptor binding before levodopa administration×100

Amount of change 1 h/4 h (%)=(amount of receptor binding 1 hour after levodopa administration−amount of receptor binding 4 hours after levodopa administration)÷amount of receptor binding 1 hour after levodopa administration×100

For the amount of striatal raclopride receptor binding,
Ratio of change B/1 h (%)=amount of change B/1 h after therapy with the composition of the invention amount of change B/1 h before therapy with the composition of the invention×100

Ratio of change 1 h/4 h (%)=amount of change 1h/4 h after therapy with the composition of the invention amount of change 1 h/4 h before therapy with the composition of the invention×100

The therapeutic effect of the pharmaceutical composition of the invention on motor complications such as motor fluctuations and dyskinesia can be studied by comparing dyskinesia expression time, ON time, OFF time, plasma drug concentration (levodopa or agent), or the like based on an amount of change in [$^{11}$C] raclopride receptor binding, a clinical evaluation scale such as UPDRS, MDS-UPDRS, UDysRS, CDRS, Rush DRS, AIMS, EQ-5D-5L, PDQ-39, CGI, or PGI, ON time or OFF time described in a patient diary, a scale calculated from locomotive movement information obtained from a wearable device such as an accelerometer and/or angular velocimeter, or the like in a placebo treated patient group and a drug treated patient group.

The protocol such as the target patient, dosing period, dosage of agent, or evaluation method in the test described above can be appropriately modified (these tests can be appropriately conducted by those skilled in the art by referring to J Clin Invest (2014) 124 (3) 1340-1349, Mov Disord. (2017) 32(2): 235-240, or the like.

In the present disclosure, a tandospirone transdermally administered formulation can be provided for therapy of Parkinson's disease by concomitant use with a therapeutic agent for Parkinson's disease such as a levodopa containing formulation. The tandospirone transdermally administered formulation in the present disclosure can be expected to have a preferred effect by administration of a levodopa containing formulation after 6 hours, preferably after 8 hours, and more preferably after 12 hours from application of the tandospirone transdermally administered formulation. Further, a stable therapeutic effect is attained without depending on the timing of administering a levodopa containing formulation by repeatedly administering a tandospirone transdermally administered formulation by replacing the formulation every predetermined amount of time.

A manufacturing method of the transdermally administered formulation of the present disclosure is described hereinafter, but the present disclosure is not limited thereto.

The transdermally administered formulation of the present disclosure can be manufactured by a commonly known method. The tape agent of the present disclosure can be manufactured, for example, according to the following Manufacturing Example 1.

Manufacturing Example 1

A common manufacturing method of tape agents (transdermal patch) is described.

The tape agent of the present disclosure can be manufactured by a common method. For example, the tape agent can be manufactured in accordance with the section directed to the manufacture of plaster agents described in "Keihi Tekiyo Seizai Kaihatsu Manyuaru" [Development manual for transdermally applied formulation], supervised by Mitsuo Matsumoto (1985). The tape agent can also be manufactured, for example, by an apparatus, method, or the like described in "Development of Portable Equipment for Manufacturing Transdermal Patches (MEMBRANE), 32(2), 116-119 (2007))".

Specifically, a common manufacturing method of adhesive tape can be applied for forming an adhesive layer in the manufacture of the tape agent of the present disclosure. A typical example thereof is a solvent coating method, but hot melt coating method, electron beam curing emulsion coating method, or the like can also be used.

To form an adhesive layer using the solvent coating method, tandospirone, adhesive containing mixture, penetration enhancer, curing agent, and other formulation components are mixed with an organic solvent to prepare an adhesive layer mixture, and the mixture is applied to one side of a support or a release liner and dried, then the organic solvent is removed, and the release liner or support is pasted on before or after drying. The thickness of an adhesive layer of a tape agent is not particularly limited, but is about 10 μm to about 600 μm, preferably about 10 μm to about 400 μm, more preferably about 20 μm to about 200 μm, still more preferably about 50 μm to about 180 μm, and especially preferably about 70 μm to about 150 μm.

Manufacturing Example 2

Preparation of Other Parenterally Administered Formulations

An ointment can be manufactured by a commonly known method. An oil and fat ointment can generally be manufactured by heating and melting an oil and fat substrate of hydrocarbons or the like such as oil and fat, wax, or paraffin, adding an active ingredient, mixing to dissolve or disperse the active ingredient, and mixing and kneading until the entire mixture is homogeneous. A water soluble ointment can generally be manufactured by heating and melting a water soluble substrate such as macrogol, adding an active ingredient, and mixing and kneading until the entire mixture is homogenous.

An ointment can be manufactured by blending tandospirone with higher alcohols such as cetanol or stearyl alcohol, higher fatty acid such as myristic acid, lauric acid, palmitic acid, stearic acid, or linoleic acid or an ester thereof, wax such as purified lanolin or spermaceti, surfactant such as sorbitan fatty acid ester or sucrose fatty acid ester, and hydrocarbons such as hydrophilic petrolatum, liquid paraffin, or plastibase. The composition of such an ointment formulation is, for example, 0.5 to 10% by weight of tandospirone, 0.1 to 5% of higher alcohol, 1 to 15% by weight of higher fatty acid or ester thereof, 1 to 10% by weight of surfactant, 4 to 10% by weight of wax, and 50 to 80% by weight of hydrocarbon. An ointment can be obtained, for example, by a manufacturing method comprising adding tandospirone and the aforementioned additive components and mixing the ingredients while heating, and maintaining a temperature of 50 to 100° C., and once all the ingredients become a transparent dissolved solution, mixing the ingredients homogenously with a homogenizer mixer, and then stirring while cooling and allowing the mixture to cool.

An injection agent or formulation for subcutaneous, intradermal, or intramuscular administration can be manufactured by a commonly known method. Such an injection agent can generally be manufactured by the following method.

(i) An active ingredient is filled directly, or an active ingredient with an addition of an additive is dissolved, suspended, or emulsified into injection water, other aqueous or non-aqueous solution or the like and homogenized, and the solution is filled into an injection container, sealed, and sterilized.

(ii) An active ingredient is filled directly, or an active ingredient with an addition of an additive is dissolved, suspended, or emulsified into injection water, other aqueous or non-aqueous solution, or the like and homogenized, and the solution is aseptically filtered or aseptically prepared and homogenized and then filled into an injection container and sealed.

The injection agent can also be manufactured as a lyophilized injection agent or powder injection agent to prevent degradation or inactivation of the active ingredient in a solution.

A lyophilized injection agent can generally be manufactured by filling an active ingredient directly, or filling an active ingredient and an additive such as an excipient, which are dissolved into injection water and aseptically filtered, into a container for an injection agent and then lyophilizing, or lyophilizing the ingredient in a specialized container and then directly filling a container therewith.

A powder injection agent can generally be manufactured by filling a container for an injection agent with powder obtained by filtration with an aseptic filter and then crystallization or the powder with addition of a sterilized additive.

For example, an active ingredient solution is prepared by dissolving tandospirone in water, organic solvent, or mixture of water and organic solvent, together with a surfactant. The resulting solution can be filtered and sterilized with a sterilization filter to prepare an aseptic active ingredient solution. In this regard, the solvent used for the dissolution (water, organic solvent, or mixture of water and organic solvent) is preferably an organic solvent or a mixture of an organic solvent and water, and more preferably a mixture of an organic solvent and water. A sterilization filter is effective for filtration and sterilization, as well as removal of foreign objects originating from raw materials or exogenous foreign objects mixed in during the manufacturing process.

Examples of surfactants include polysorbate 80, polysorbate 20, polyoxyethylene hydrogenated castor oil 50, polyoxyethylene hydrogenated castor oil 60, poloxamer 188, polyoxyethylene castor oil, benzalkonium chloride, sodium lauryl sulfate, and the like, and two or more thereof can also be used. A surfactant is preferably polysorbate 80. A surfactant is preferably used at about 0.005% (w/v) to about 10% (w/v).

As the water, purified water, water of the same or higher grade than purified water, or injection water is used.

Examples of organic solvent include alcohol solvents (e.g., methanol, ethanol, and the like), aprotic solvents (e.g., acetone, dimethyl sulfoxide, N,N-dimethylacetamide, and the like), and the like, or two or more solvents can be used. The organic solvent is preferably 1-propanol, methanol, ethanol, 2-propanol, acetone, dimethyl sulfoxide, or N,N-dimethylacetamide.

The injection agent of the present disclosure can be intramuscularly or subcutaneously injected after attaching an injection needle to a prefilled syringe filled with a formulation. The injection agent can also be administered by aspirating a formulation from a container such as vial filled with the formulation into an injection syringe via an injection needle and then discharging the formulation intramuscularly or subcutaneously. Furthermore, a formulation can be a lyophilized formulation obtained by filling the formulation into a container such as a vial and lyophilizing the formulation, or a powder filled formulation prepared by filling dried powder crystal obtained by isolating and then drying the active ingredient crystal in the formulation in a container such as a vial. Lyophilized formulations and powder filled formulations can be intramuscularly or subcutaneously injected after aspirating a suspension prepared by suspending the formulation in a container with a suspension solution at the time of use from the container into an injection syringe via an injection needle. The injection agent of the present disclosure can also be intramuscularly or subcutaneously injected after placing a container filled with a formulation on a needleless syringe (syringe capable of administration without an injection needle by utilizing pressure generated by gas, initiating agent, spring, or the like incorporated into an injection device, and having a mechanism for discharging the drug solution filled in the container).

Example of Preparing a Sustained Subcutaneous Injection Pump

The injection agent of the present disclosure can be sustainably administered by using a commercially available subcutaneous sustained injection pump. A subcutaneous sustained injection pump is an apparatus for subcutaneously injecting a drug sustainably to a patient via an injection tube, having a drug storage unit and a pump for sustained injection of the drug. Such an apparatus generally has a built-in clock and program that can change the amount of injection per a certain period of time. A drug storage unit is a sealed container filled with a drug solution adjusted to a drug concentration required for the drug efficacy, comprising a drug inlet and outlet for connection to the pump. A pump is a pump that can sustainably inject the drug solution precisely at a minute amount, which is an apparatus that can inject a minute amount of liquid from about 0.1 mL/day to 10 mL/hr. A drug storage unit is filled with and stores an aseptically guaranteed tandospirone solution.

A sustained injection agent is an injection agent that is applied subcutaneously, intradermally, intramuscularly, or the like in order to release an active ingredient over a long period of time. A sustained injection agent can be manufactured by a commonly known method, generally by dissolving or suspending an active ingredient in plant oil or the like, or by preparing a suspension of microspheres using biodegradable macromolecular compounds.

An implanted agent is a solid or gel-like injection agent applied using an instrument for implantation under the skin, in the muscle, or the like, or by surgery in order to release an active ingredient over a long period of time. An implanted agent can be manufactured by a commonly known method. An implanted agent can generally be obtained by using a biodegradable macromolecular compound to prepare a pellet, microsphere, or gel-like formulation.

(Combined Drug)

The transdermally administered formulation of the present disclosure can be concomitantly used with an existing therapeutic agent for Parkinson's disease other than levodopa. Examples of such an existing therapeutic drug for Parkinson's disease include, but are not limited to, dopamine agonists (e.g., bromocriptine, pergolide, talipexole, cabergoline, pramipexole, ropinirole, rotigotine, and the like), monoamine oxidase B (MAOB) inhibitors (e.g., selegiline, rasagiline, and Safinamide), catechol-O-methyltransferase (COMT) inhibitors (e.g., entacapone), amantadine, apomorphine, istradefylline, anticholinergic drugs (e.g., biperiden, trihexyphenidyl, profenamine, and mazaticol), tiapride, droxidopa, carbidopa, zonisamide, and the like.

The present disclosure is specifically described in more detail with Reference Examples, Examples, and Test Examples, but the present disclosure is not limited thereto. The compound names used in the following Reference Examples, Examples, and the like do not necessarily follow the IUPAC nomenclature.

EXAMPLES

The Examples are described hereinafter.

While the products described in the Examples were used as the specific reagents, the products can be substituted with an equivalent product from other manufacturers (Sigma-Aldrich, Wako Pure Chemical, Nacalai Tesque, R&D Systems, USCN Life Science INC, or the like).

Manufacturing Example

Reference Manufacturing Example 1: Manufacture of Tandospirone

Tandospirone ((1R,2S,3R,4S)—N-[4-[4-(pyrimidine-2-yl)piperadine-1-yl]butyl]-2,3-bicyclo[2.2.1]heptanedicarboximide) has the chemical formula set forth below. The manufacturing method thereof is described in Japanese Laid-Open Publication No. 58-126865. The description thereof is incorporated herein by reference.

[Chemical Formula 2]

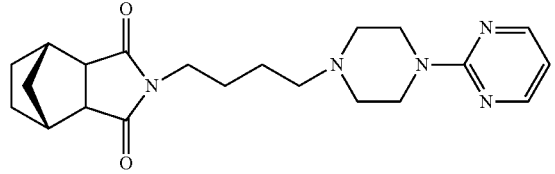

(Reference Manufacturing Example 2: Manufacture of Tandospirone Tape Agent)

(Manufacture of Tandospirone Tape Agent)

An acrylic adhesive (MAS683, CosMED Pharmaceutical Co. Ltd., 35.6% by weight solids, 12.5068 g), ethyl acetate (1.5 mL), and polyoxyethylene lauryl ether (0.2530 g) were mixed. An ethyl acetate (5.5 mL) solution of tandospirone (0.32512 g) was prepared and added to the mixture of adhesive and thoroughly stirred. The resulting mixture was spread on a support and dried for one day at room temperature. A release liner was then pasted therewith to manufacture a tandospirone tape agent.

(Manufacture of Placebo Tape Agent)

An acrylic adhesive (MAS683, CosMED Pharmaceutical Co. Ltd., 35.6% by weight solids, 18.6962 g), ethyl acetate (5.5 mL), and polyoxyethylene lauryl ether (0.3520 g) were mixed and thoroughly stirred. The resulting mixture was spread on a support and dried for one day at room temperature. A release liner was then pasted therewith to manufacture a placebo tape agent.

50.8 μm of polyethylene terephthalate and/or ethylene vinyl acetate copolymer laminate film (Scotchpak #9732) from 3M Health Care Ltd. was used as the support. Bynasheet 64S-018B from Fujimori Kogyo Co., Ltd. was used as the release liner.

Table 1

Table 1. Drug content in tandospirone tape agent

| | Thickness (μm) | Tandospirone content (mg/cm²) |
|---|---|---|
| Formulation 1 | 99 | 0.6 |
| Formulation 2 | 94 | 0.6 |
| Formulation 3 | 114 | 0.7 |
| Formulation 4 | 105 | 0.7 |
| Formulation 5 | 150 | 1.0 |

Measurement of Residual Drug in Tape Agent

While an example of measurement conditions for the amount of residual drug is described below, another verified measurement method can be used instead.

<Example of Measurement Conditions>

Preparation of Standard Solution

A tandospirone solution (about 4, 20, or 100 μg/mL) is prepared.

Preparation of Formulation Solution (1) A tape agent is placed in a container. 10 mL of acetone is added, and ultrasound wave is irradiated thereon for 30 minutes.

(2) 1 mL of methanol is added to 1 mL extract of (1) and mixed.

(3) The solution is filtered with a filter (Millipore: Millex-FH (0.45 μm, PTFE)).

High performance liquid chromatography (HPLC) condition Column: YMC-Pack ODS-AM 250×4.6 mm (particle size: 5 μm) Column oven: 40° C.

Detector: ultraviolet absorption spectrophotometer (measurement wavelength: 240 nm)

Flow rate: 0.9 mL/min

Amount injected: 10 μL

Mobile phase: 10 mM phosphate buffer (pH 6.8)/acetonitrile mixture (35:65)

(Evaluation of Plasma Concentration)

1. Testing Method 1.1. Pretreatment Operation Method

50 μL of rat plasma sample was fractionated into a polypropylene microtube. 50 μL of methanol (50 μL of standard solution for calibration curve sample) and 200 μL of internal standard solution (Bezafibrate methanol solution: 200 nmol/L, 200 μL of methanol for blank sample) are added and stirred for about 10 seconds with a mixer. This is centrifuged (4° C., 4500 rpm, 10 min), and then the supernatant is subjected to vacuum filtration using a filter (FastRemover MF 0.2 μm). 70 μL of aqueous 10 mmol/L ammonium acetate solution is added to 70 μL of the resulting filtrate and stirred for about 10 seconds with a mixer to prepare a measurement sample. The tandospirone concentration is measured by liquid chromatography-mass spectrometry.

1.2. Measurement Conditions

Column: XSELECT CSH C18, 3.5 μm, 100×3.0 mm I.D.

Column temperature: 50° C.

Mobile phase A: aqueous 10 mmol/L ammonium acetate solution Mobile phase B: methanol Flow rate: 0.6 mL/min Gradient Condition:

Table 2

| Time (min) | 0 | 0.10 | 5.00 | 6.00 | 6.01 | 9.00 |
|---|---|---|---|---|---|---|
| Mobile phase B (%) | 15 | 15 | 95 | 95 | 15 | 15 |

Ionization method: electrospray ionization

Detection method: multiple reaction monitoring, positive ion detection mode

Monitor ion: 384.2/122.1 (tandospirone Q1/Q3, m/z), 362.02/138.9 (Bezafibrate Q1/Q3, m/z)

Example 1: Evaluation of Tandosprone's Action of Prolonging ON-Time of Levodopa in Parkinson's Disease Animal Model This Example evaluated tandosprone's antiparkinsonian action time, i.e., "ON-time", of levodopa using various routes of administration in Parkinson's disease animal models.

A rat striatum dopaminergic denervation model using topical administration of 6-hydroxydopamine (hereinafter, also referred to as "6-OHDA") to one side of the brain is known as a typical experimental model for Parkinson's disease (rats treated on one side with 6-OHDA (6-OHDA-lesioned rats)). It is known that said model exhibits a rotational behavior to the opposite side from the site of injection of 6-OHDA due to a therapeutic drug for Parkinson's disease, which activates the intracerebral dopaminergic nervous system, such as levodopa or dopamine receptor agonist. The usefulness of a therapeutic drug for Parkinson's disease can be evaluated using such a rotational behavior as an indicator. Since prolongation of rotational behavior time by levodopa can be interpreted as leading to prolongation of ON-time in Parkinson's disease (improvement in motor fluctuations), prolongation in levodopa induced rotational behavior time was evaluated by using this model.

(Testing Method: Preparation of Animal Model)

Wistar male rats (12-week old, Japan SLC, Inc.) were used for the preparation of animal models. Desipramine hydrochloride (25 mg/kg; Wako Pure Chemical) was intraperitoneally administered. After 30 minutes from the administration, the rats were subjected to isoflurane inhalational anesthetic using a general anesthesia apparatus for experimental animals. Under isoflurane anesthesia, the rats were immobilized to a brain stereotaxic instrument. The skin on the head was incised with a surgical scalpel to expose the skull. The coordinates of the bregma used as the origin (AP: 0, ML: 0, DV: 0) was determined, and the coordinates of the right medial forebrain bundle (AP: −4.4 mm, ML: 1.5 mm, DV: 7.8 mm from bregma) were measured. After inserting an injection tube for administration at the measured coordinates, 6-OHDA (9 μg/4 μL; Sigma-Aldrich) inducing dopaminergic denervation was topically injected. After 2 weeks from surgery, apomorphine hydrochloride hemihydrate (0.5 mg/kg; Wako Pure Chemical) was subcutaneously administered, and the rotation movement to the opposite side from the 6-OHDA injected site was observed. Rats with 7 rotations or more per minute were used as rats treated on one side with 6-OHDA.

(Oral Administration)

Tandospirone citrate (suspended in 0.5% methyl cellulose solution) or a solvent (0.5% methyl cellulose solution) was orally administered 5 minutes before observation of rotational behavior to rats treated on one side with 6-OHDA. Levodopa methyl ester hydrochloride (5 mg/kg in levodopa free form) comprising benserazide at ¼ the amount of levodopa in terms of free form concentration was intraperitoneally administered. Benserazide is an agent that is known to suppress the metabolism of levodopa in the periphery, increase the blood levodopa concentration, and increase the intracranial penetration of levodopa. The number of rotations to the opposite side from the site of injection of 6-OHDA was counted for 180 minutes from immediately after the intraperitoneal administration, and the count was tallied in 5 minute increments. The results in the drawings are indicated in terms of mean value±standard error. As the ON-time of each individual, the total value of measured time for 5 minute increments exhibiting a rotation tally that is 20% or more of the peak value of the rotation tally for 5 minute increments in the individual was calculated. The test results were statistically analyzed by comparison with the solvent administration group using the Steel test. * indicates $p<0.05$ and ** indicates $p<0.01$, meaning that there is a significant difference.

(Transdermal Administration)

For evaluation of a tape agent, the abdominal regions of the rats were shaved prior to the evaluation date. The tape agent was applied to the abdominal regions of the rats on the evaluation date at 60 $cm^2$/kg (including 6.5% W/V tandospirone free form). After 4 minutes from application, levodopa methyl ester hydrochloride (5 mg/kg in levodopa free form) comprising benserazide at ¼ the amount of levodopa in terms of free form concentration was intraperitoneally administered. The number of rotations to the opposite side from the site of injection of 6-OHDA was counted for 180 minutes from immediately after the intraperitoneal administration, and the count was tallied in 5 minute increments. The results in the drawings are indicated in terms of mean value±standard error. Individuals with 50% or more of the tape agent coming off during the test were excluded from analysis. As the ON-time of each individual, the total value of measured time for 5 minute increments exhibiting a rotation tally that is 20% or more of the peak value of the rotation tally for 5 minute increments in the individual was calculated. The test results were statistically analyzed by comparison with the solvent administration group using the Steel test. ** indicates $p<0.01$, meaning that there is a significant difference.

(Transdermal Administration: Stripping Conditions)

When evaluating a tape agent under stratum corneum stripping conditions (tandospirone high exposure conditions), stripping was performed 10 times at the abdominal region of rats using a transpore surgical tape (3M) on the evaluation date, and a tape agent was then applied at 60 $cm^2$/kg (including 6.5% W/V tandospirone free form).

(Results)

Figure 1A:
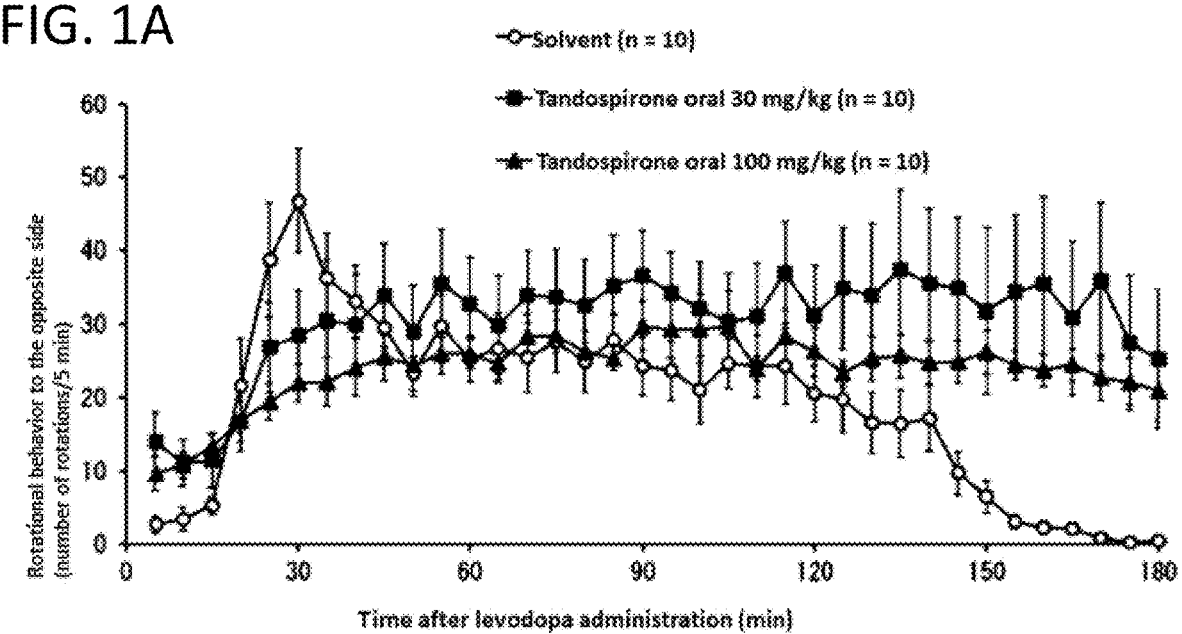
FIGS. 1A-1B show results of measuring the ON-time (antiparkinsonian action effective time associated with levodopa therapy of Parkinson's disease) by measuring for 180 minutes the rotational behavior (total number of rotations in 5 minutes) after levodopa administration to Parkinson's disease rat models (6-OHDA-lesioned rats) by oral administration of tandospirone. ON-time was defined as the period of time exhibiting a number of rotations that is 20% or greater of the peak value of the total number of rotations in 5 minutes from levodopa administration. Prolongation of ON-time was observed at 120 minutes to 180 minutes after levodopa administration (FIG. 1A) and a significant prolongation of total ON-time was observed to 180 minutes (FIG. 1B) relative to the solvent administration group by oral administration of tandospirone citrate (30 mg/kg and 100 mg/kg).
Figure 1B:
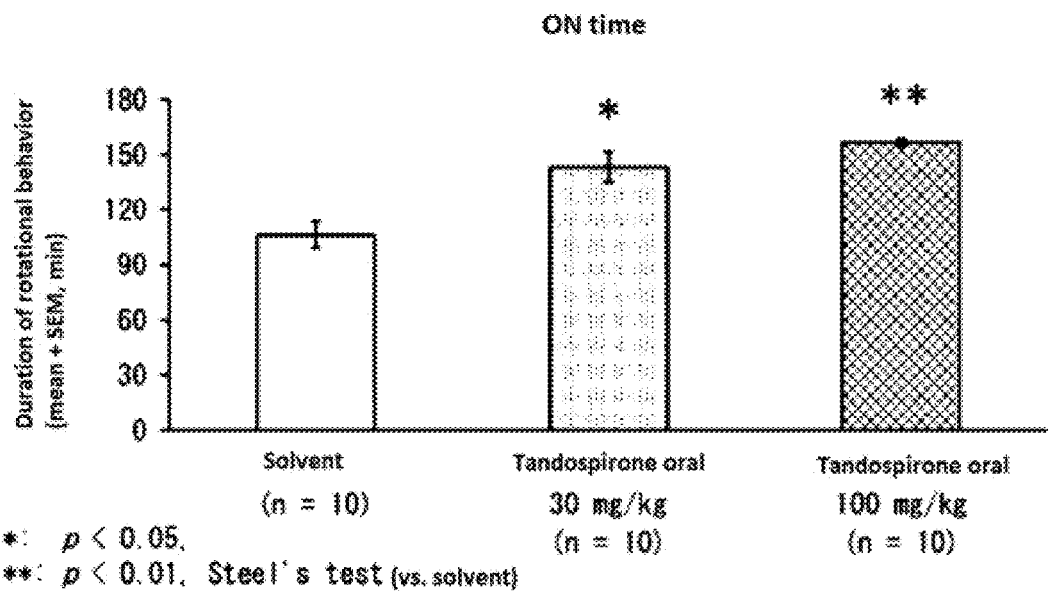
Figure 2A:
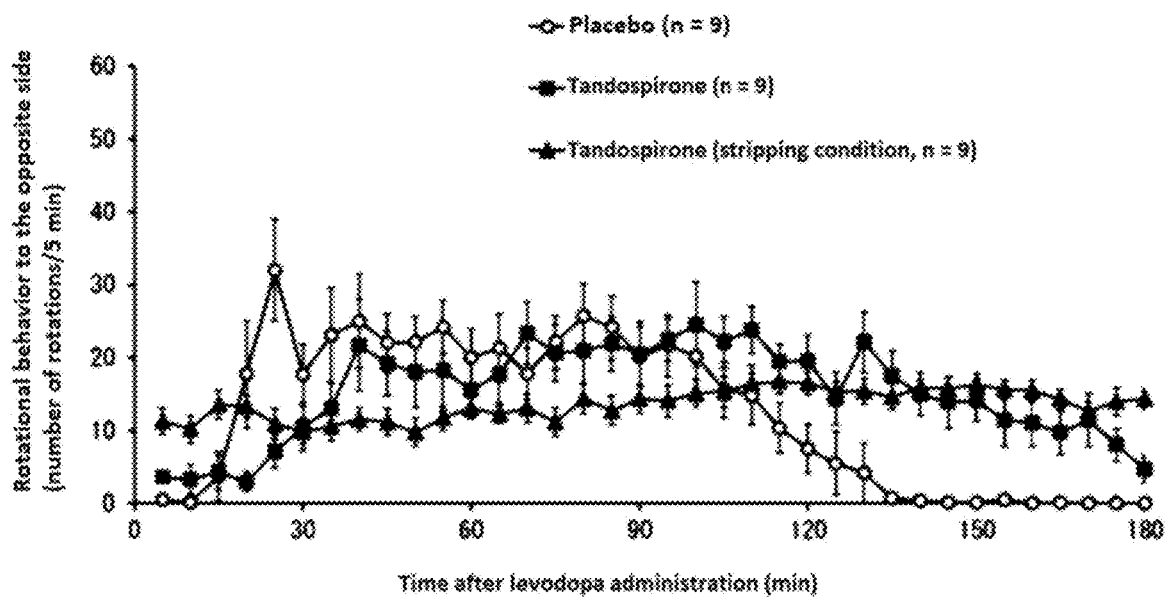
FIGS. 2A-2B show results of measuring the ON-time by measuring, for 180 minutes, the rotational behavior (total number of rotations in 5 minutes) after levodopa administration to Parkinson's disease rat models (6-OHDA-lesioned rats) by transdermal administration of tandospirone. ON-time was defined as the period of time exhibiting a number of rotations that is 20% or greater of the peak value of the total number of rotations in 5 minutes from levodopa administration. Prolongation of ON-time was observed at 120 minutes to 180 minutes after levodopa administration (FIG. 2A) and a significant prolongation of total ON-time was observed to 180 minutes (FIG. 2B) relative to the solvent administration group by applying a tandospirone tape agent (60 cm$^2$/kg (including 6.5% W/V tandospirone free form)).
Figure 2B:
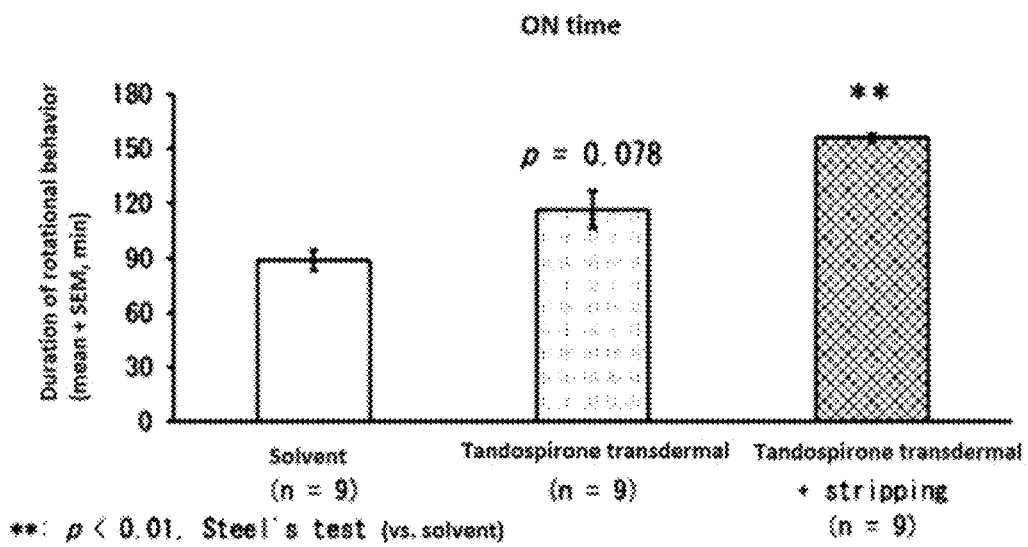

Prolongation of ON-time was observed at 120 minutes to 180 minutes after levodopa administration (FIG. 1A) and a significant prolongation of ON-time was observed to 180 minutes (FIG. 1B) relative to the solvent administration group by oral administration of tandospirone citrate (30 mg/kg and 100 mg/kg). Prolongation of ON-time was observed at 120 minutes to 180 minutes after levodopa administration (FIG. 2A) and a significant prolongation of ON-time was observed to 180 minutes (FIG. 2B) relative to the placebo tape administration group by applying a tandospirone tape agent (with/without stripping condition).

In view of the above results, tandospirone exhibited the same ON-time prolongation action by different administration methods of oral administration and transdermal administration.

Example 2: Evaluation of ON-Time Prolongation Action in PD-LID Animal Model

This Example evaluated tandospirone's antiparkinsonian action time, i.e., ON-time, of levodopa in PD-LID animal models.

(Test Method)

To make a PD-LID rat model, a mixture of levodopa methyl ester hydrochloride (6 mg/kg; Sigma-Aldrich) dissolved in saline and benserazide hydrochloride (15 mg/kg; Sigma-Aldrich) (hereinafter, also referred to as "levodopa containing solution") was intraperitoneally administered once daily to 6-OHDA-lesioned rats. The levodopa containing solution was repeatedly administered for 3 weeks or longer to observe and evaluate the behavior. The behavior was observed and evaluated in a transparent acrylic cage for 1 minute every 20 minutes after 20 minutes from the intraperitoneal administration of the levodopa containing solution, up until after 3 hours from administration. Observation of behavior was classified into Limb AIMs (involuntary bending or stretching of front limbs on the opposite side of the disorder, opening/closing of hands, up and down movement of the wrist, chorea-like tremor, dystonia-like stiffening), Axial AIMs (twisting of the upper body/neck to the opposite side of the disorder, losing balance and falling, or maintaining an unstable posture), Orolingual AIMs (trembling of the jaw or violently sticking out the tongue forward), and Locomotive behavior (rotational behavior to the other side of the destruction), and was given a score from 0 to 4 (0: none, 1: less than 30 seconds of manifestation, 2: 30 seconds or more of manifestation, 3: constantly, but stopped with a stimulus such as sound, and 4: constant manifestation, which does not stop with a stimulus such as sound). The sum of the scores for Limb AIMs, Axial AIMs, and Orolingual AIMs in 3 hours was used as the total dyskinesia-like symptom (AIMs) score. Individuals with a total AIMs score of less than 10 were excluded from the test as not manifesting a dyskinesia-like symptom. The behavior was observed and evaluated before the drug evaluation date. The rats were assigned to each dosing group by using the 3 hour total dyskinesia-like symptom (AIMs) score, Locomotive behavior score, and rat body weight as indicators, which were used for evaluation of drugs.

For an indicator of dyskinesia behavior, the sum of the Limb AIMs, Axial AIMs, and Orolingual AIMs at each evaluation point was used as the AIMs score. For the rotational behavior (ON score), Locomotive behavior at each evaluation point was used as an indicator. The total ON score in 3 hours was used as the total ON score. For ON time without dyskinesia, the period during which the AIMs score is 0 and Locomotive behavior is 1 or greater at each evaluation point was added.

Duration of action of levodopa without a dyskinesia symptom (ON time without dyskinesia) refers to the aggregate time with no dyskinesia during the antiparkinsonian action effective time, i.e., "ON-time", and defined as the time during which the dyskinesia symptom (AIMs) score is 0 and the rotational behavior (Locomotive behavior) score is 1 or greater at each evaluation point after levodopa administration.

(Oral Administration)

Tandospirone citrate (30 mg/kg, 100 mg/kg as citrate concentration) was suspended in a 0.5% methylcellulose solution and orally administered to rats. After 5 minutes, a levodopa containing solution was intraperitoneally administered, and the behavior was observed and evaluated. The results in the drawings are indicated in terms of mean value±standard error. The test results were statistically analyzed by comparison with the solvent administration group using the Steel test with the total ON score in 3 hours or ON time without dyskinesia as an indicator. ** indicates p<0.01, meaning that there is a significant difference.

(Transdermal Administration)

For evaluation of a tape agent, the abdominal regions of the rats were shaved prior to the evaluation date. The tape agent was applied to the abdominal regions of the rats on the evaluation date at 60 $cm^2$/kg (including 6.5% W/V tandospirone free form). After 4 hours from application, a levodopa containing solution was intraperitoneally administered to observe and evaluation the behavior. The results in the drawings are indicated in terms of mean value±standard error. Individuals with 50% or more of the tape agent coming off during the test were excluded from analysis. The test results were statistically analyzed by comparison with the placebo tape administration group using Wilcoxon rank sum test with the total ON score in 3 hours or ON time without dyskinesia as an indicator. * indicates p<0.05 and ** indicates p<0.05, meaning that there is a significant difference compared to the solvent oral administration group or the placebo tape administration group.

(Transdermal Administration: Stripping Conditions)

When evaluating a tape agent under stratum corneum stripping conditions (tandospirone high exposure conditions), stripping was performed 10 times at the abdominal region of rats using a transpore surgical tape (3M) on the evaluation date, and a tape agent was then applied at 60 $cm^2$/kg (including 6.5% W/V tandospirone free form).

(Results)

Figure 3A:
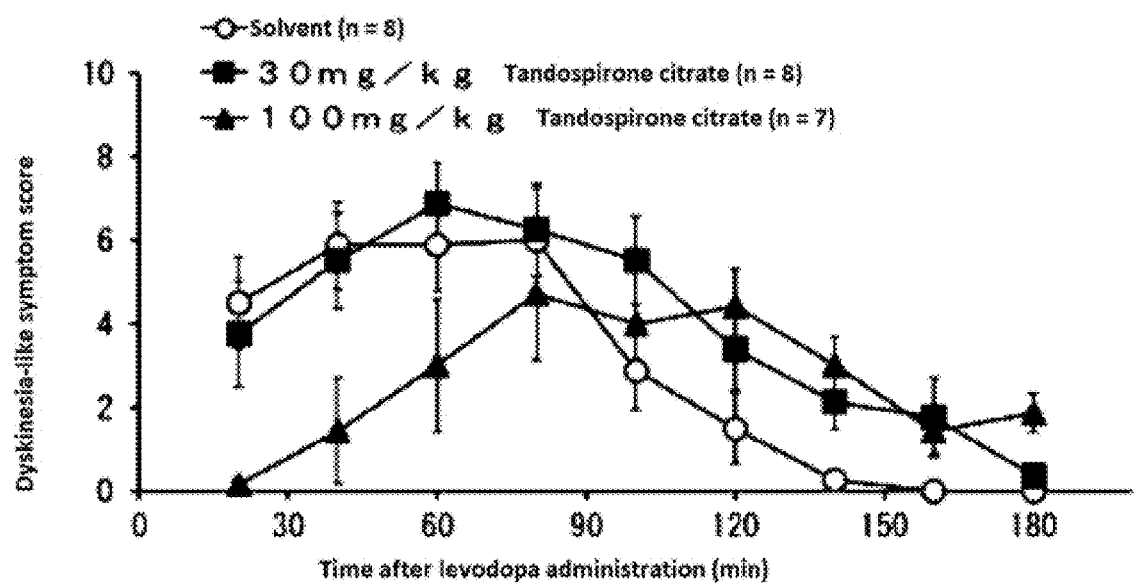
FIGS. 3A-3D show results of measuring dyskinesia-like symptoms and rotational behavior (ON score) for 180 minutes every 20 minutes by administering levodopa to PD-LID rat models by oral administration of tandospirone. Behavior was observed and evaluated from 20 minutes after intraperitoneal administration of levodopa to 3 hours after administration within a transparent acrylic cage for 1 minute every 20 minutes. Observation of behavior was classified into Limb AIMs (involuntary bending or stretching of front limbs on the opposite side of the disorder, opening/closing of hands, up and down movement of the wrist, chorea-like tremor, dystonia-like stiffening), Axial AIMs (twisting of the upper body/neck to the opposite side of the disorder, losing balance and falling, or maintaining an unstable posture), Orolingual. AIMs (trembling of the jaw or violently sticking out the tongue forward), and Locomotive behavior (rotational behavior to the other side of the destruction), and was given a score from 0 to 4 (0: none, 1: less than 30 seconds of manifestation, 2: 30 seconds or more of manifestation, 3: constantly, but stop with a stimulus such as sound, and 4: constant manifestation, which does not stop with a stimulus such as sound). The sum of the scores for Limb AIMs, Axial AIMs, and Orolingual AIMs in 3 hours was used as the total dyskinesia-like symptom (AIMs) score. Tandospirone citrate (30 mg/kg, 100 mg/kg as citrate concentration) was orally administered to a PD-LID rat model, and levodopa was administered 5 minutes later to evaluate the scores for dyskinesia-like symptoms (FIG. 3A) and rotational behavior (FIG. 3B). The results are indicated in terms of mean value±standard error. From oral administration of tandospirone citrate (100 mg/kg), an increase in the total ON score was observed (FIG. 3C), and a significant prolongation in the ON-time without dyskinesia for 180 minutes (Locomotive behavior 1, and AIMs score=0) was observed (FIG. 3D).
Figure 3B:
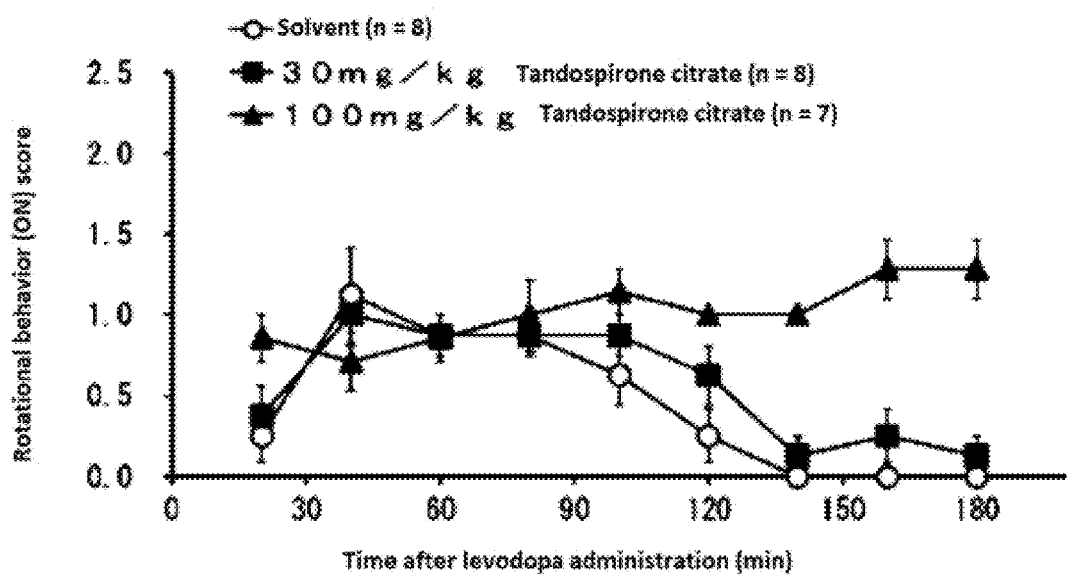
Figure 3C:
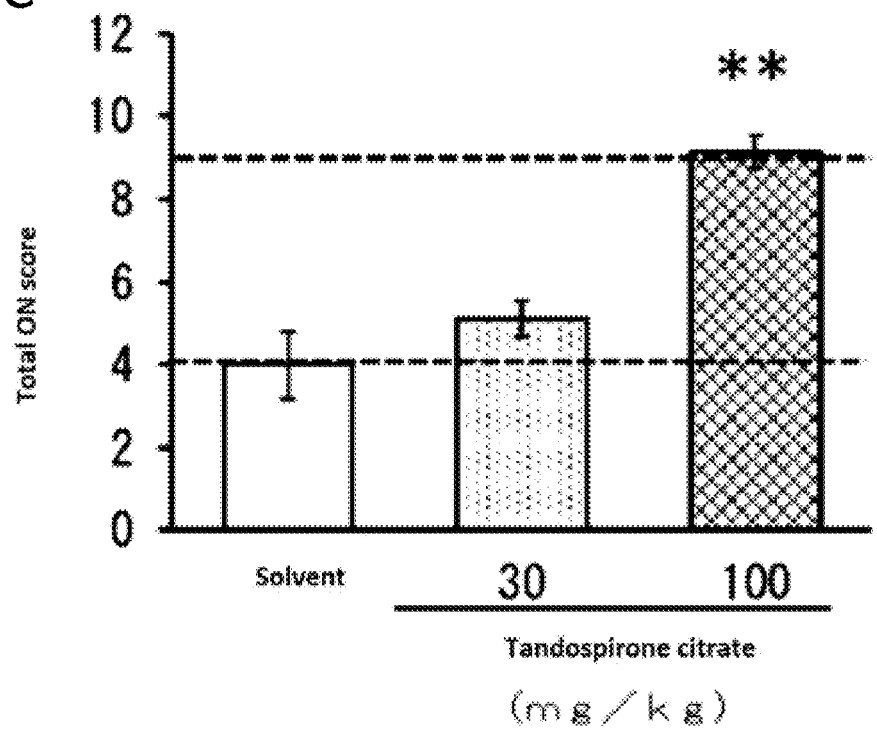
Figure 3D:
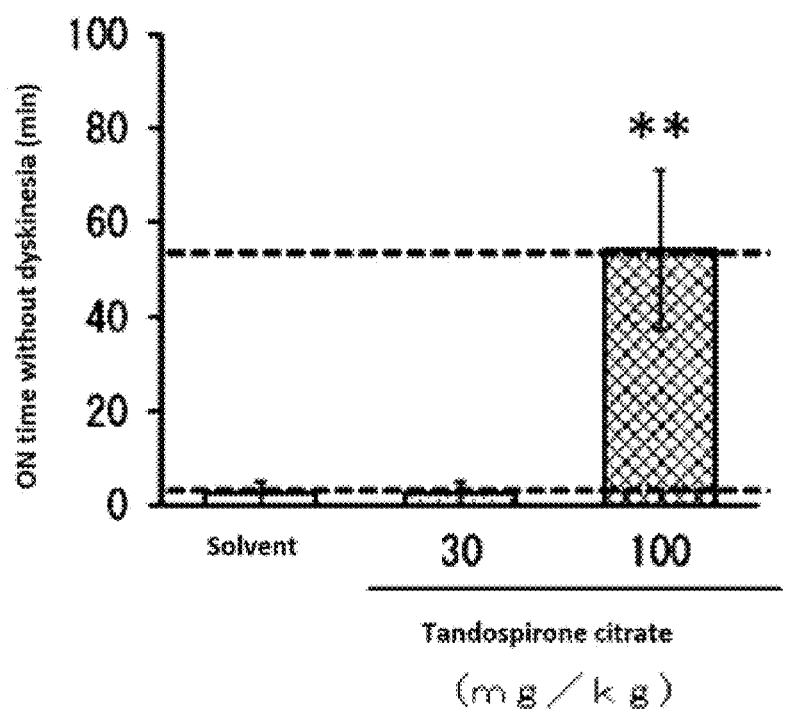
Figure 4A:
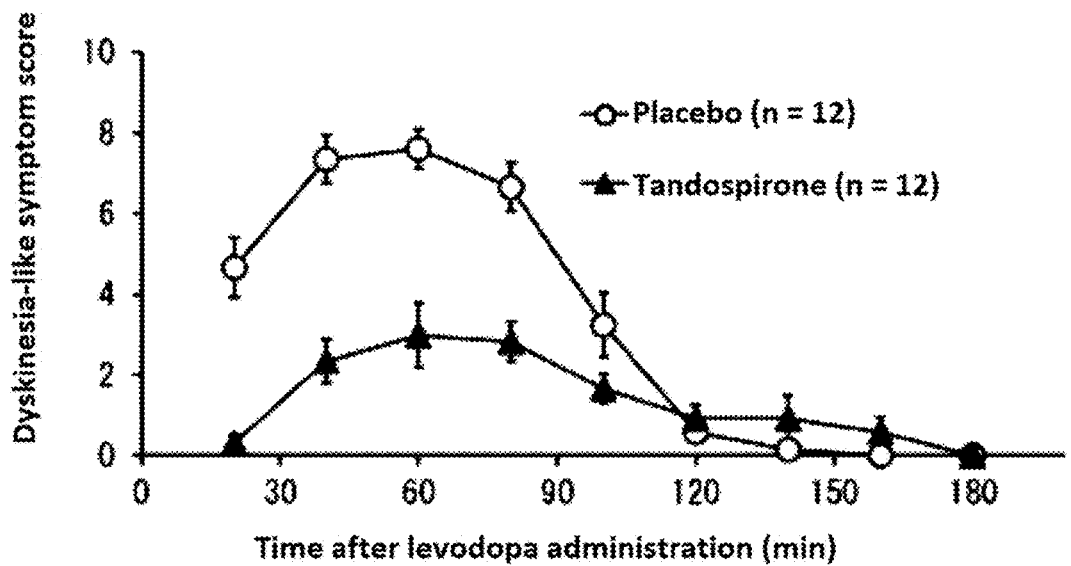
FIGS. 4A-4D show results of measuring dyskinesia-like symptoms and rotational behavior (ON score) for 180 minutes every 20 minutes by administering levodopa to PD-LID rat models by transdermal administration (no stripping) of tandospirone. Specifically, a tandospirone tape agent was transdermally administered to a PD-LID rat model and levodopa was administered 4 hours later to evaluate dyskinesia-like symptoms (FIG. 4A) and rotational behavior (FIG. 4B). The results are indicated in terms of mean value±standard error. From application of a tandospirone tape agent, an increase in the total ON score was observed (FIG. 4C), and a significant prolongation in the ON-time without dyskinesia for 180 minutes (Locomotive behavior 1, and AIMs score=0) was observed (FIG. 4D).
Figure 4B:
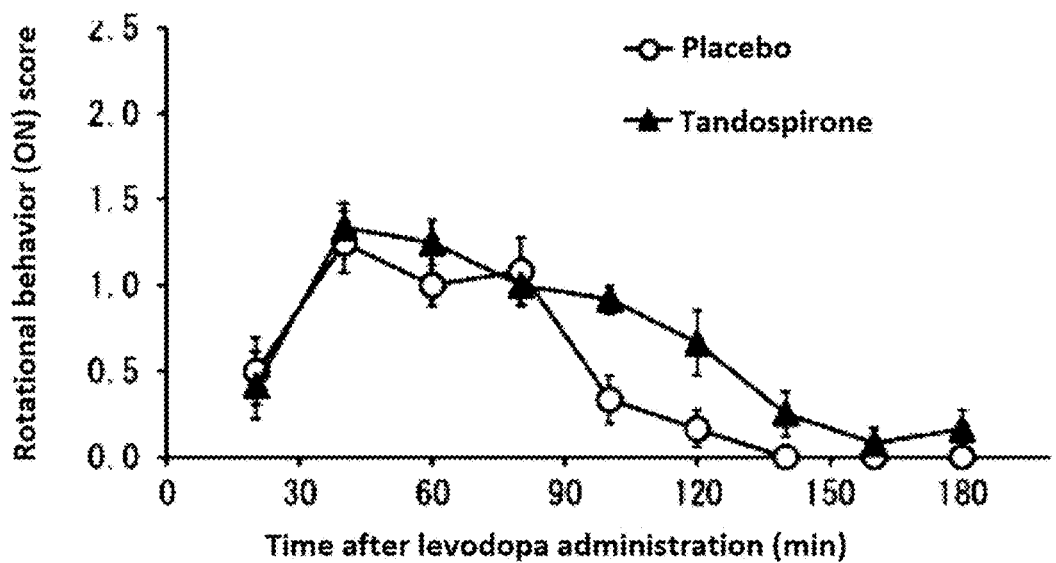
Figure 4C:
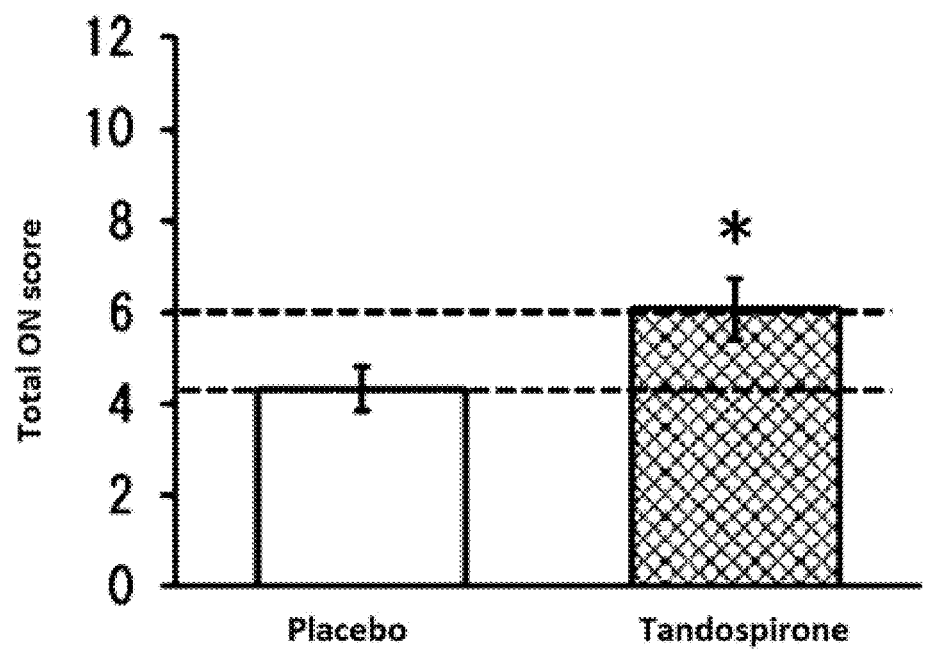
Figure 4D:
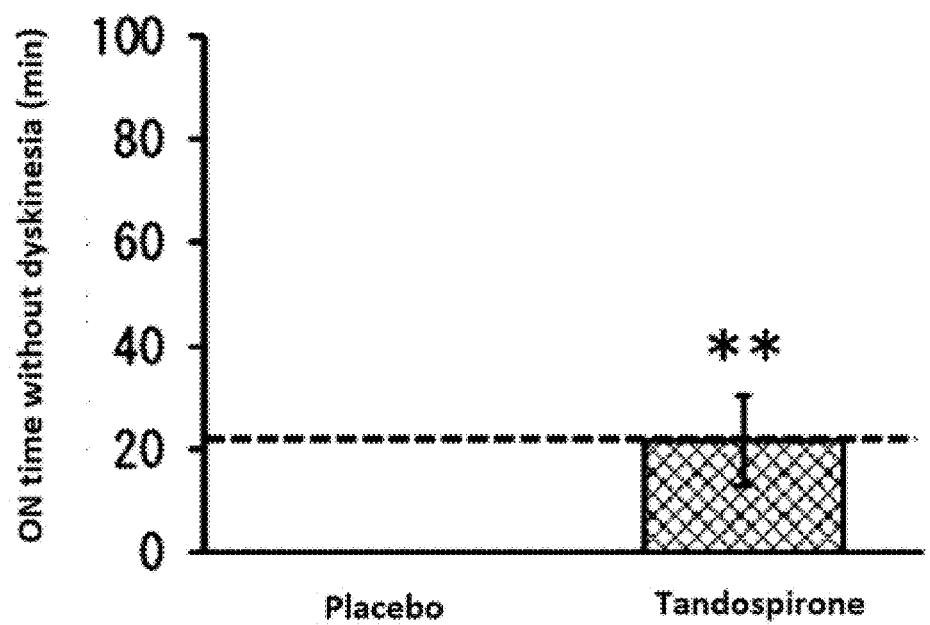
Figure 5A:
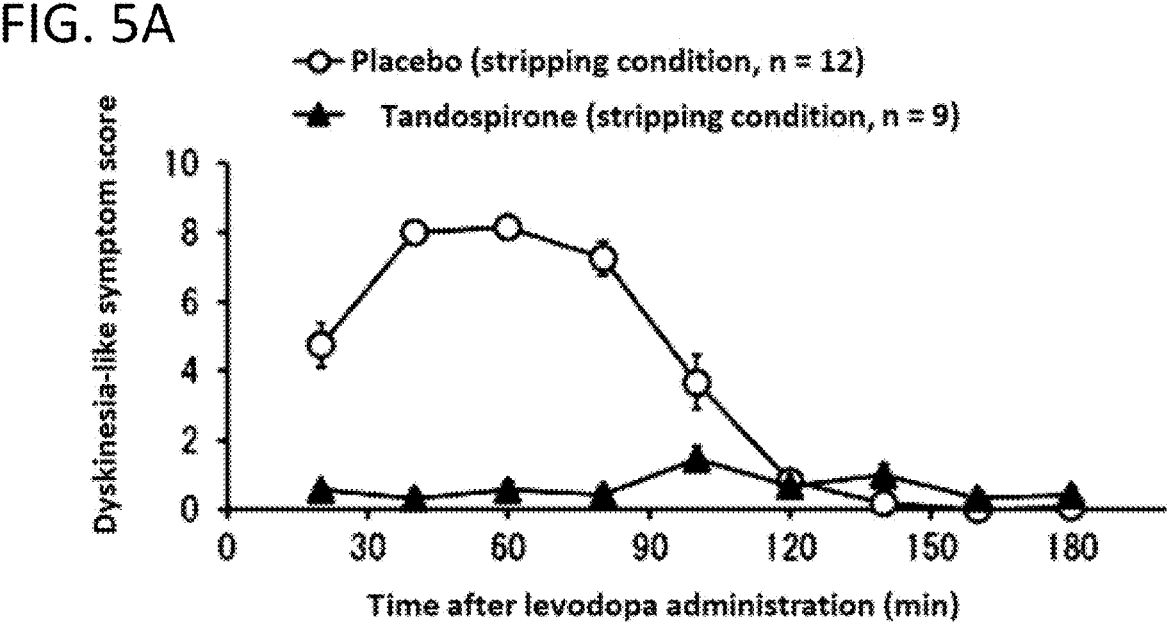
Figure 5B:
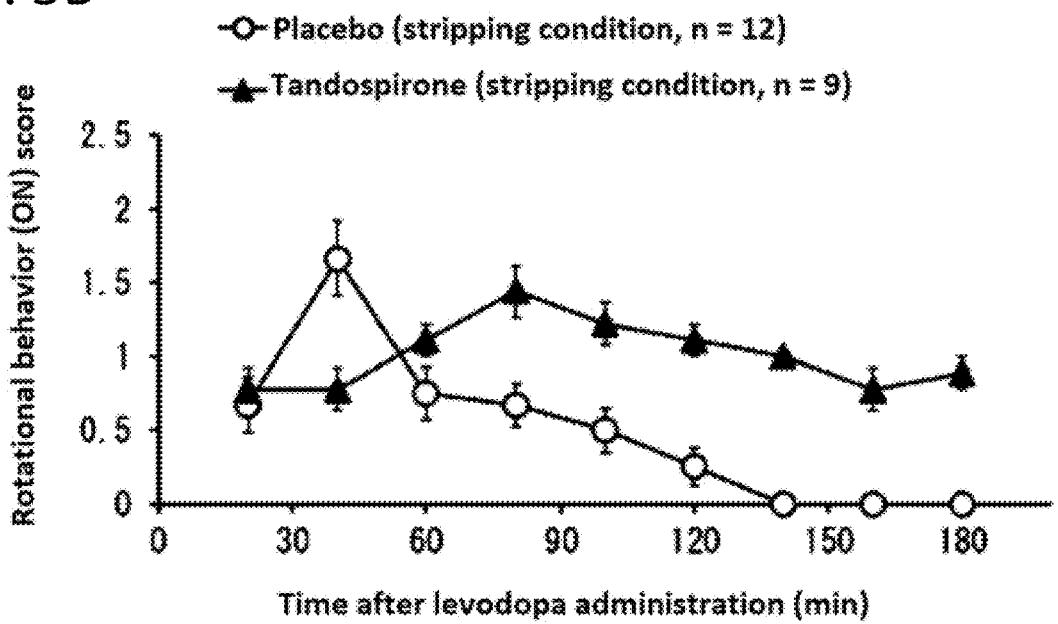

An increase in the total ON score after 180 minutes of levodopa administration was observed (FIG. 3C) and an increase in ON time without dyskinesia for 180 minutes was observed (FIG. 3D) relative to the solvent administration group by oral administration of tandospirone citrate (30 mg/kg and 100 mg/kg). Prolongation of ON-time was observed at 180 minutes after levodopa administration (FIGS. 4C and 5C) and an increase in ON time without dyskinesia for 180 minutes was observed (FIGS. 4D and 5D) relative to the placebo tape administration group by applying a tandospirone tape agent (with/without stripping condition).

In view of the above results, tandospirone exhibited an action of prolonging ON-time in PD-LID rat models. In particular, ON time without dyskinesia increased from tandospirone transdermal administration, but prolongation of ON time without dyskinesia was observed only at a dose at which there is a risk of side effects (100 mg/kg) from oral administration. This suggests that oral administration cannot provide preferred therapy. It was rather unexpected that a therapeutic effect which is comparable to that from oral administration can be exerted with transdermal administration.

Example 3: Evaluation of the Dopamine Release Action in the Striatum in PD-LID Animal Models (Test Method)

To measure dopamine release in the striatum, PD-LID rat models were subjected to guide cannula implantation surgery in the striatum and chromatography by the methods described in a reference document (Pharmacol Res Perspect. 2015 June; 3(3): e00142.) On the day of the test, a dialysis probe was inserted into the striatum along the guide cannula. A tape agent was applied to the abdominal regions of rats at 60 $cm^2$/kg (including 6.5% W/V tandospirone free form). After 4 hours from application, a levodopa containing solution was intraperitoneally administered, and dialysate was collected in a sample vial every 10 minutes. The dopamine level in the collected dialysate was measured using an HPLC-ECD system (EiCom). The results in the drawings are indicated in terms of mean value±standard error. Individuals with 50% or more of the tape agent coming off during the test were excluded from analysis. The test results were statistically analyzed by comparison with the placebo tape administration group using t-test. * indicates p<0.05, meaning that there is a significant difference compared to the placebo tape administration group.

(Results)

Figure 6A:
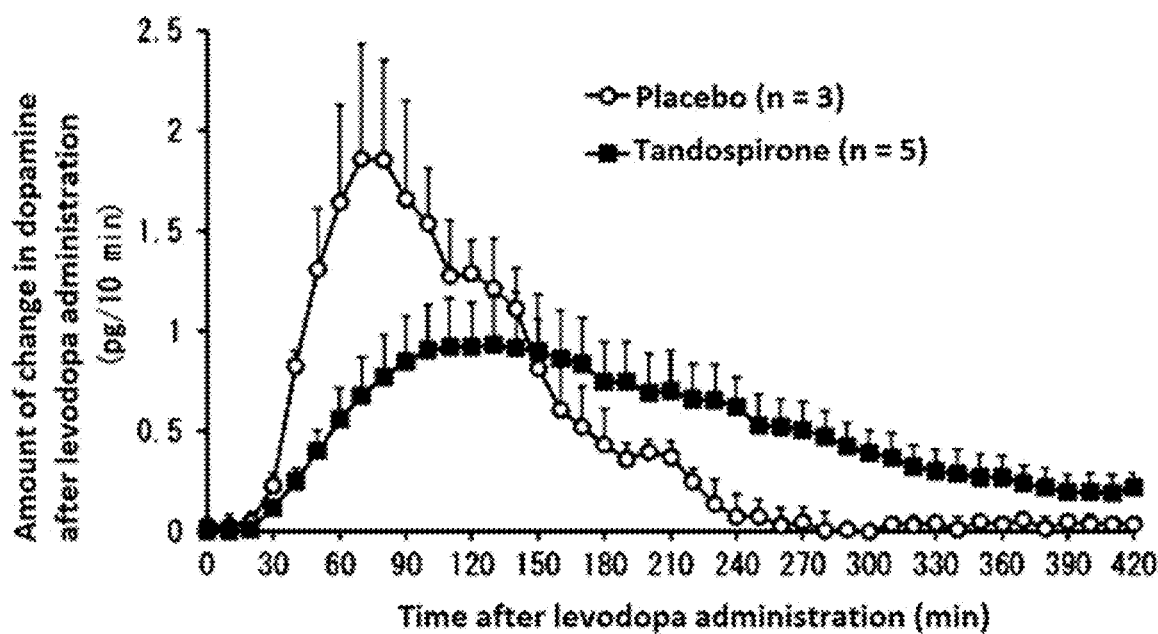
FIG. 6A is the result of intraperitoneally administering levodopa to a PD-LID rat model and measuring the change in the amount of dopamine over time in the striatum by microdialysis.
Figure 6B:
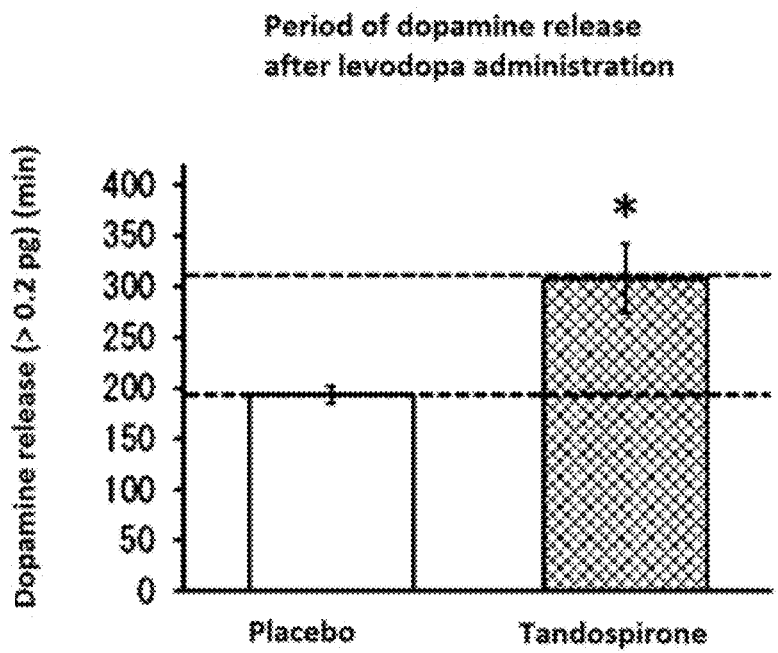
FIG. 6B is the result of computing the time during which the amount of change in released dopamine is 0.2 pg or greater. An effect of prolongation of period of striatum dopamine release relative to the placebo group was observed from application of a tandospirone tape agent.
Figure 6C:
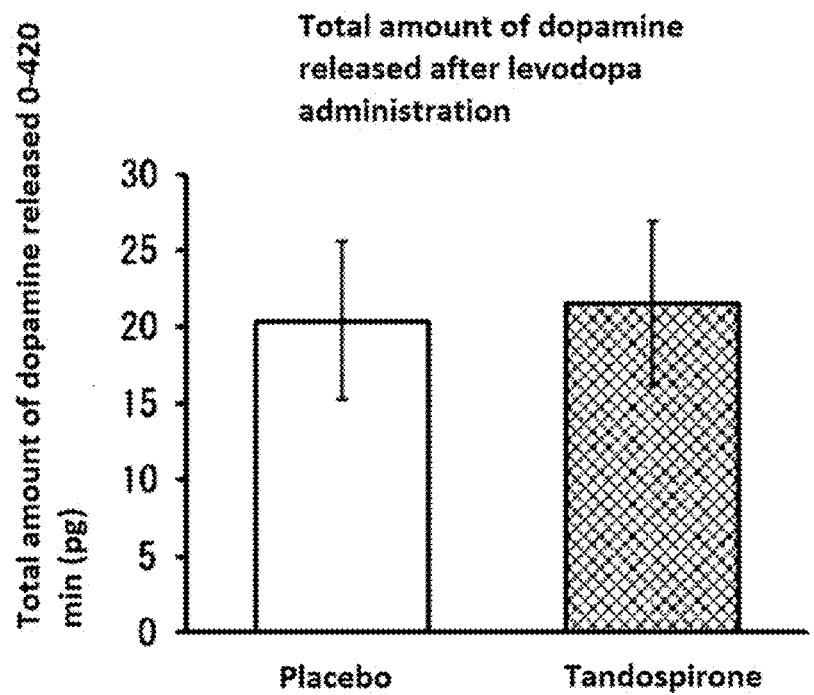
FIG. 6C is the resulting total released dopamine after levodopa administration. A difference in total released dopamine was not found.

The amount of change in dopamine (pg) was measured at every sampling point (every 10 minutes). The amount was calculated as the amount of change from a baseline (mean value of 4 samples before administration of levodopa containing solution), which was calculated up to 420 minutes after administration of levodopa containing solution. A tandospirone tape agent reduced the amount of dopamine released in the striatum from 30 minutes to 150 minutes after levodopa administration, and increased the amount of dopamine released after 150 minutes (FIG. 6A). The period of time during which the amount of change in released dopamine is 0.2 pg or greater was calculated. A significant prolongation was found relative to the placebo tape administration group by applying a tandospirone tape agent (FIG. 6B). Meanwhile, a difference in the total amount of dopamine released after levodopa administration was not found (FIG. 6C).

In view of the above results, a tandospirone tape agent exhibited a sustained action of releasing dopamine in the striatum in PD-LID. Specifically, a tandospirone tape agent was found to exhibit an action of suppressing excessive secretion of dopamine immediately after dopamine administration and maintaining a constant dopamine level in the synaptic cleft of the striatum for an extended period of time by gradually releasing dopamine in PD-LID.

While it is understood that motor complications associated with levodopa therapy for Parkinson's disease have an effect on the rapid increase/disease in the levodopa level in the synaptic cleft of the striatum, it was found that tandospirone is expected to have an effect of improving PD-LID or motor fluctuations associated with levodopa therapy for Parkinson's disease by suppressing rapid increase/decrease in the dopamine level in the synaptic cleft of the striatum, and has an ideal pharmacological action that can comprehensively treat motor complications.

Example 4: Evaluation of Change in the Plasma Concentration from Applying a Tandospirone Tape Agent to a Normal Rat (Test Method)

Wistar male rats (14-week old, Japan SLC, Inc.) were used. The abdominal regions of the rats were shaved prior to the tape agent evaluation date, and the tape agent of formula 1 was applied to the abdominal regions on the evaluation date (the size was 9 $cm^2$). Blood was collected over time after 2, 4, 6, and 24 hours from application to analyze the plasma tandospirone concentration. The results are indicated by mean value±standard deviation.

(Results)

Figure 7:
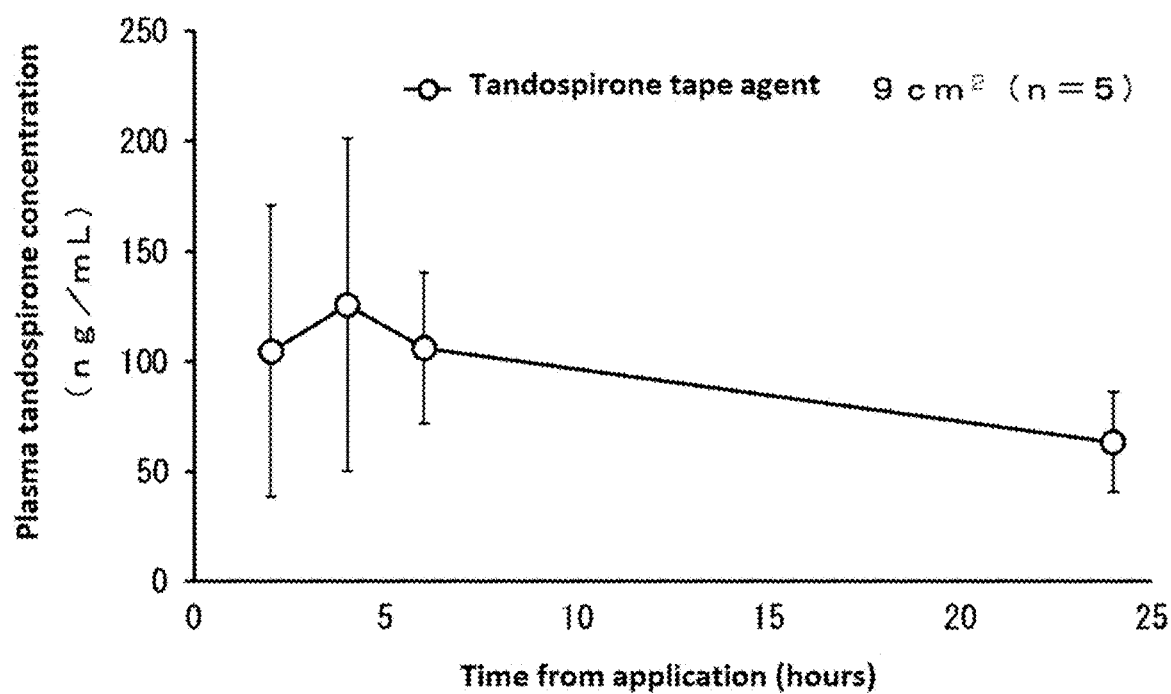
FIG. 7 shows evaluation of changes in plasma concentration when a tandospirone tape agent in Example 4 was applied to a normal rat. Specifically, changes in plasma tandospirone concentrations obtained by applying a tandospirone tape agent to a normal rat (9 cm$^2$: 31±2 cm$^2$/kg) are shown in terms of mean value±standard deviation. The x axis indicates the time from application, and the y axis indicates the plasma tandospirone concentration.

A change in the plasma tandospirone concentration shown in FIG. 7 was observed from applying a tandospirone tape agent (9 cm$^2$: 31±2 cm$^2$/kg). It was confirmed that a tape agent smooths out and sustains the blood tandospirone concentration.

Example 5: Evaluation of Tandospirone Tape Agent on Motor Complications (Transdermal Administration (Condition 1))

When evaluating a tape agent, the hair on the abdominal region of rats was shaved before the evaluation date. The tape agent of formulation 2 was applied to the abdominal regions of rats on the evaluation date at 60 cm$^2$/kg (37 mg/kg). After 4 hours from application, a levodopa containing solution was intraperitoneally administered to observe and evaluate the behavior. Individuals with 50% or more of the tape agent coming off during the test were excluded from analysis. After the completion of observation and evaluation of behavior, plasma was collected to analyze the plasma tandospirone concentration.

(Transdermal Administration (Condition 2))

When evaluating a tape agent under stratum corneum stripping conditions (tandospirone high exposure conditions), stripping was performed 10 times at the abdominal region of rats using a transpore surgical tape (3M) on the evaluation date, and a tape agent of formulation 3 was then applied at 60 cm$^2$/kg (45 mg/kg). After 4 hours from application, a levodopa containing solution was intraperitoneally administered to observe and evaluate the behavior. Individuals with 50% or more of the tape agent coming off during the test were excluded from analysis. After the completion of observation and evaluation of behavior, plasma was collected to analyze the plasma tandospirone concentration.

When evaluating dyskinesia-like symptoms, the sum of the Limb AIMs, Axial AIMs, and Orolingual AIMs at each evaluation point was used as the AIMs score. Statistical analysis on test results was performed by Wilcoxon rank sum test using the total dyskinesia-like symptom (AIMs) score, which is the sum of AIMs scores for 3 hours, and total dyskinesia-like symptom score in 100 to 180 minutes as parameters. ** indicates p<0.01, meaning that there is a significant difference compared to the placebo tape agent application group. The results in the drawings are indicated in terms of mean value±standard error.

(Results)

Figure 8A:
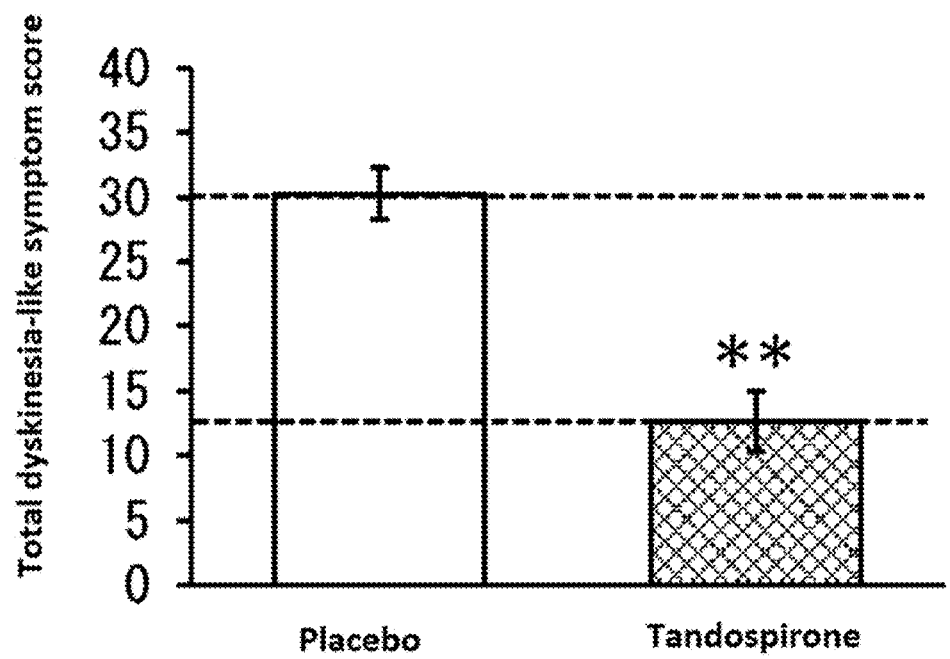
FIGS. 8A-8B shows results under administration condition 1 in Example 5. The total dyskinesia-like symptom (AIMs) score was 12.6 when tandospirone was transdermally absorbed after applying a tandospirone tape agent (formulation 2: drug dosage of 37 mg/kg) via transdermal administration (condition 1). The total AIMs score decreased 17.7 relative to application of a placebo tape agent free of tandospirone. Thus, a significant improvement in dyskinesia-like symptom was observed. Specifically, a tandospirone tape agent was transdermally administered to a PD-LID rat model and levodopa was administered 4 hours later to evaluate dyskinesia-like symptoms. The results are indicated an terms of mean value±standard error. ** indicates $p<0.01$, meaning that there is a significant difference compared to a placebo tape agent application group (Wilcoxon rank sum test).
Figure 8B:
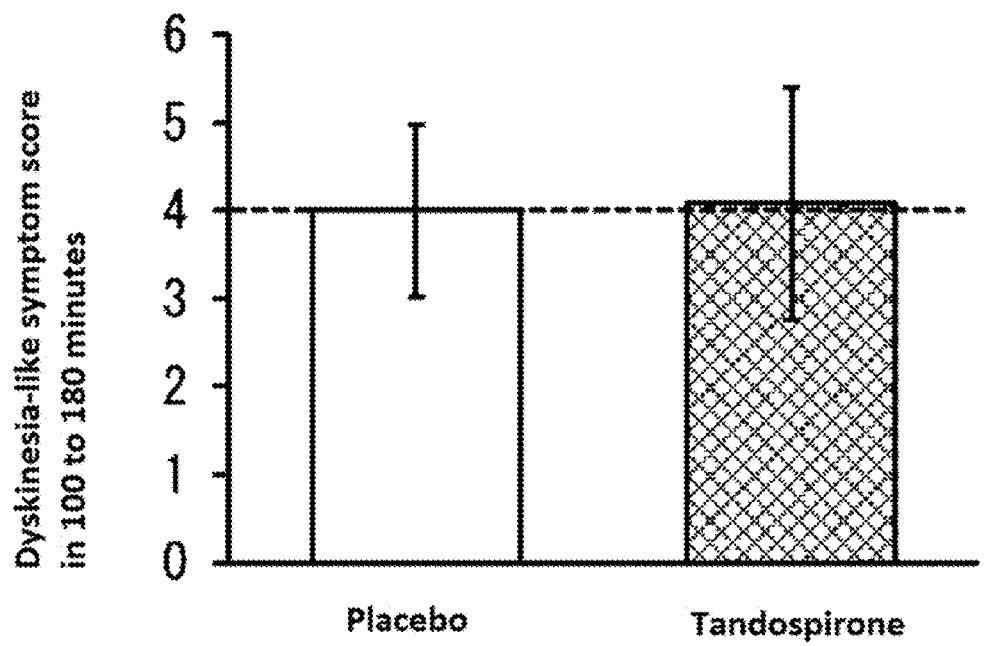

When tandospirone was transdermally absorbed by applying a tandospirone tape agent (formulation 2: drug dosage of 37 mg/kg) via transdermal administration (condition 1), the total AIMs score was 12.6. Compared to application of a placebo tape agent without tandospirone, the total AIMs score decreased 17.7, so that a significant improvement was observed in dyskinesia-like symptoms (FIG. 8A). Further, a clear dyskinesia-like symptom (mean AIMs score of 2 or greater) was not observed for the placebo tape agent application group or the tandospirone tape agent application group at 120 to 140 minutes after levodopa administration. A significant difference was not found between the two groups in the total dyskinesia-like symptom score in 100 to 180 minutes (FIG. 8B). The mean value of plasma tandospirone concentrations measured after the completion of observation and evaluation of behavior was 71.8 ng/mL.

Figure 9A:
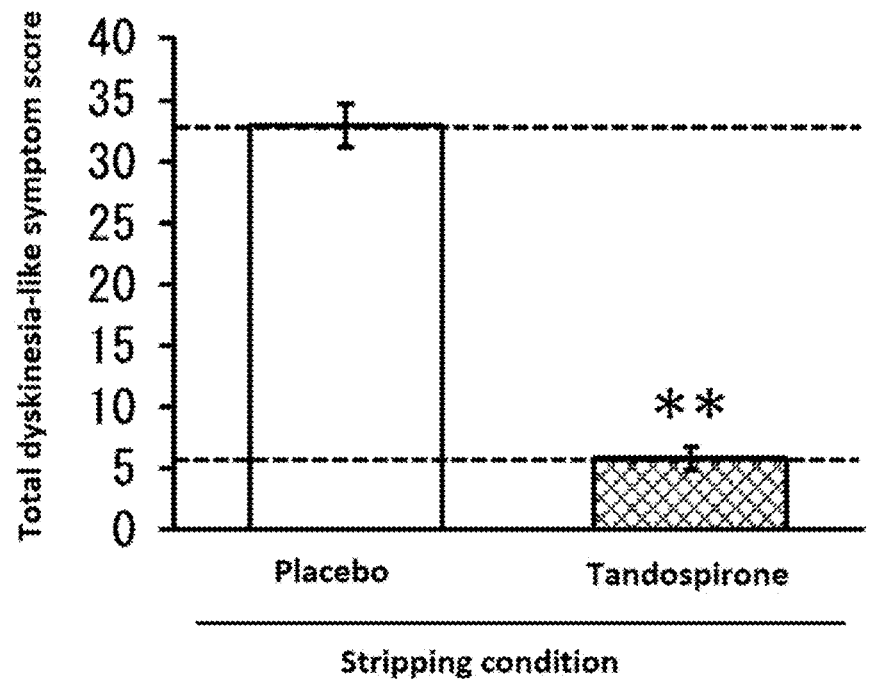
FIGS. 9A-9B show results under administration condition 2 in Example 5. The total dyskinesia-like symptom (AIMs) score was 5.8 when a high exposure tandospirone was transdermally absorbed after applying a tandospirone tape agent (formulation 3: drug dosage of 45 mg/kg) under stratum corneum stripping conditions. Specifically, a tandospirone tape agent was transdermally administered to a PD-LID rat model on which stratum corneum stripping was performed on the tape agent application site, and levodopa was administered 4 hours later to evaluate dyskinesia-like symptoms. The results are indicated in terms of mean value±standard error. ** indicates $p<0.01$, meaning that there is a significant difference compared to a placebo tape agent application group (Wilcoxon rank sum test).
Figure 9B:
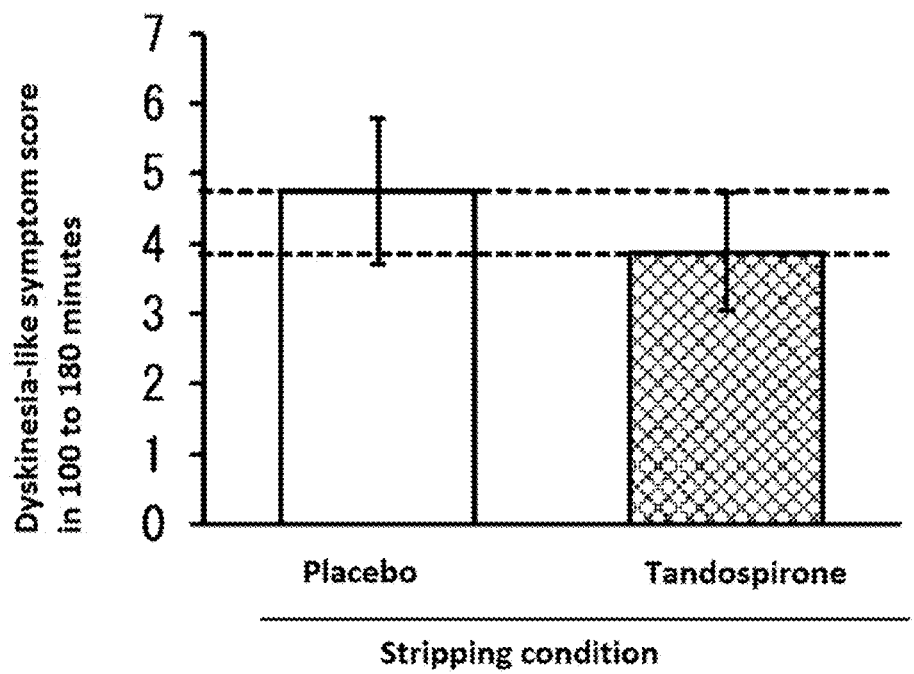

When a high exposure tandospirone was transdermally absorbed by applying a tandospirone tape agent (formulation 3: drug dosage of 45 mg/kg) under stratum corneum stripping conditions via transdermal administration (condition 2), the total AIMs score was 5.8. Compared to application of a placebo tape agent without tandospirone, the total AIMs score decreased 27.1, so that a significant improvement was observed in dyskinesia-like symptoms. A higher effect of improvement was observed under administration condition 2 than under administration condition 1 (FIG. 9A). Further, a clear dyskinesia-like symptom (mean AIMs score of 2 or greater) was not observed for the placebo tape agent application group or the tandospirone tape agent application group at 120 to 140 minutes after levodopa administration under stratum corneum stripping conditions. A significant difference was not found between the two groups in the total dyskinesia-like symptom score in 100 to 180 minutes (FIG. 9B). The mean value of plasma tandospirone concentrations measured after the completion of observation and evaluation of behavior was 269 ng/mL. The mean value of plasma tandospirone concentration under administration condition 2 was 3 times or higher than that under administration condition 1.

In view of the above results, tandospirone transdermally administered formulations improved motor fluctuation symptoms without a rebound symptom of dyskinesia.

Further, it was found that the effect on PD-LID and anxiolytic action of tandospirone is exerted at the same dosage in a non-clinical model. The anxiolytic action was evaluated using a rat Vogel conflict test model, and the effect on PD-LID was evaluated in 6-OHDA-lesioned rats. Therefore, the therapeutic effect in the present disclosure is exerted at the same blood concentration as tandospirone citrate tablets (Sediel tablets) commercially available as anxiolytic drugs.

Example 6: Evaluation of Motor Complications Upon Continuous Subcutaneous Infusion of Tandospirone (Testing Method)

As in Example 2, a levodopa containing solution was repeated administered to 6-OHDA-lesioned rats for 3 weeks or longer to observe and evaluate the behavior. The behavior was observed and evaluated before the drug evaluation date. The rats were assigned to each dosing group by using the 3 hour dyskinesia-like symptom (AIMs) score, Locomotive behavior score, and rat body weight as indicators, which were used for evaluation of drugs. However, individuals with a total AIMs score of less than 10 were excluded from the test as lacking manifestation of a dyskinesia-like symptom. Individuals with a body weight deviating 10% or more from the mean body weight were also excluded from the test to minimize variation in the dosage for each individual.

Tandospirone (free form) was dissolved in 1 M hydrochloric acid (Nacalai Tesque) and diluted with saline and adjusted to 0.05, 0.25, or 1.25 mg/kg/hour. The prepared solution was used after injection into an ALZET® Osmotic Pump MODEL 2ML1 (9.68 µL/hour; DURECT).

An osmotic pump injected with tandospirone or solvent was implanted under the skin of rats in each group with n=6. After 4 hours, a levodopa containing solution was administered to observe and evaluate the behavior. After the observation and evaluation of behavior, blood was collected from rats in the tandospirone administration group to analyze the plasma tandospirone concentration.

Figure 10A:
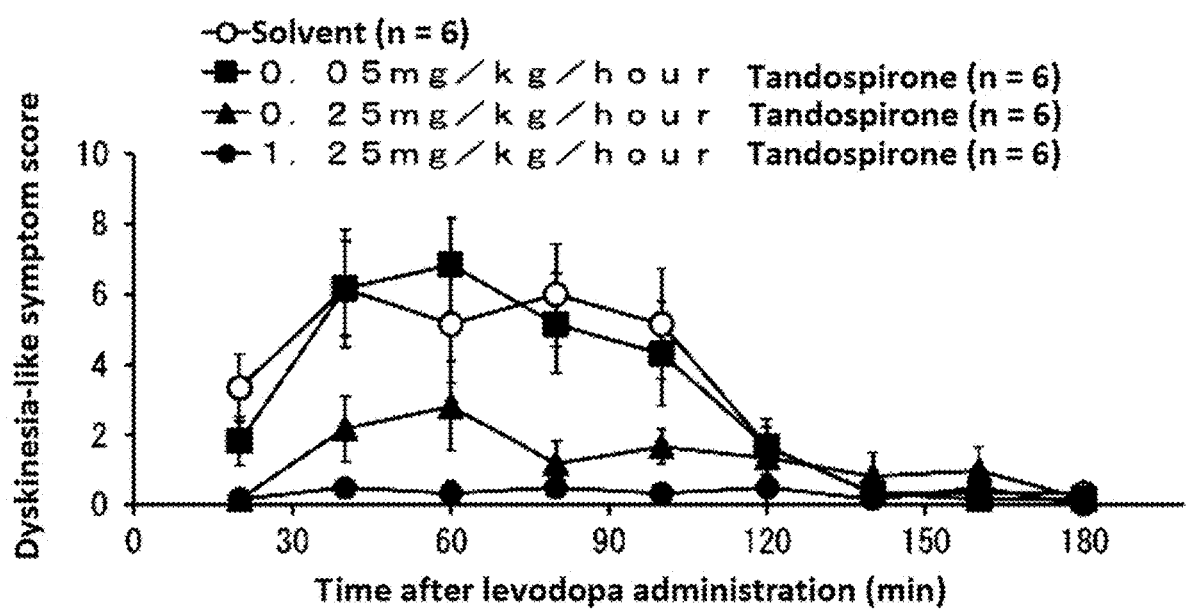
FIGS. 10A-10C show evaluation of improvement in dyskinesia-like symptoms upon continuous subcutaneous infusion of tandospirone in Example 6. Specifically, tandospirone was subcutaneously and sustainably administered to a PD-LID rat model, and levodopa was administered 4 hours later to evaluate the dyskinesia-like symptoms. The results are indicated in terms of mean value±standard error. * indicates $p<0.05$, meaning that there is a significant difference compared to the solvent administration group (Steel test). Continuous subcutaneous infusion of tandospirone dose-dependently improved dyskinesia-like symptoms, and significant improvement was observed at 1.25 mg/kg/hour (FIGS. 10A and 10B). Furthermore, the total dyskinesia-like symptom (AIMs) score dose-dependently decreased by continuous subcutaneous infusion of tandospirone, and a significant improvement was observed at 1.25 mg/kg/hour in the total dyskinesia-like symptoms in 100 to 180 minutes (FIG. 10C).
Figure 10B:
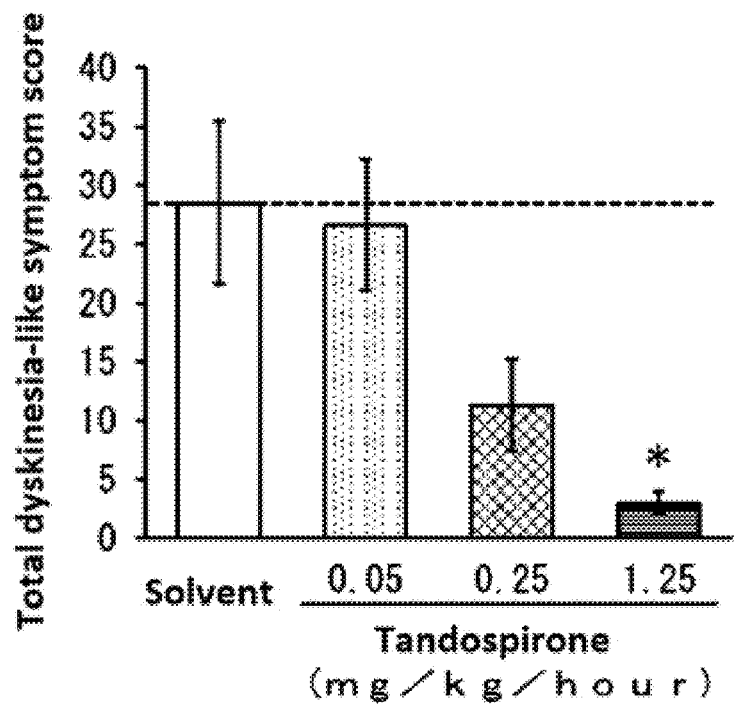
Figure 10C:
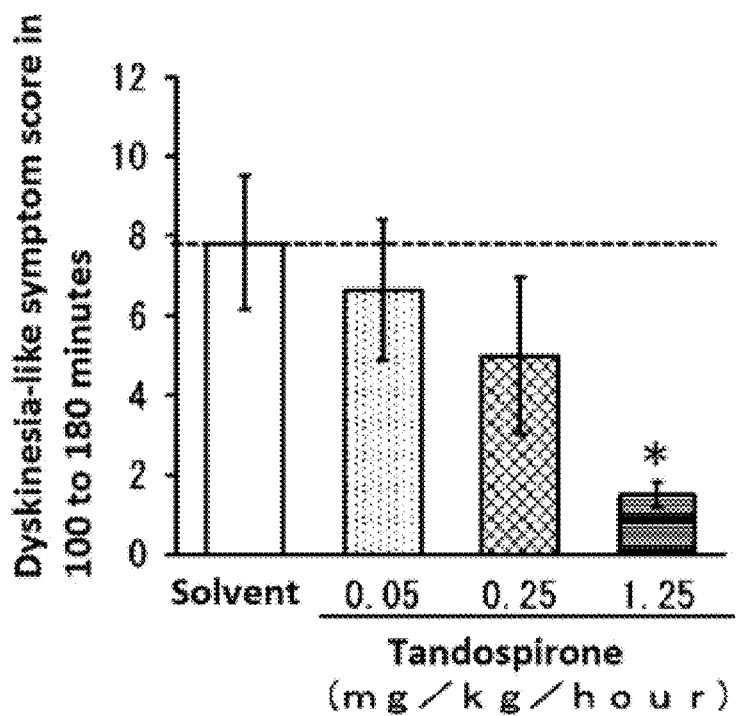

The results in FIGS. 10A-10C are indicated in terms of mean value±standard error. The test results were statistically analyzed by comparison with the solvent administration group by Steel test using the total dyskinesia-like symptom (AIMs) score in 3 hours and the total dyskinesia-like symptom score in 100 to 180 minutes as parameters. * indicates p<0.05, meaning that there is a significant difference.

(Results)

Continuous subcutaneous infusion of tandospirone dose-dependently improved dyskinesia-like symptoms, and significant improvement was observed at 1.25 mg/kg/hour (FIGS. 10A and 10B). A clear dyskinesia-like symptom (mean AIMs score of 2 or greater) was not found in both the solvent administration group and the tandospirone administration group at 120 to 140 minutes after levodopa administration. Furthermore, the total dyskinesia-like symptom (AIMs) score dose-dependently decreased by continuous subcutaneous infusion of tandospirone, and a significant improvement was observed at 1.25 mg/kg/hour in the total dyskinesia-like symptom score in 100 to 180 minutes (FIG. 10C). The mean value of plasma tandospirone concentration measured after the completion of the observation and evaluation of behavior was 23.5 ng/mL at 0.05 mg/kg/hour, 119 ng/mL at 0.25 mg/kg/hour, and 541 ng/mL at 1.25 mg/kg/hour.

In view of the results, continuous subcutaneous infusion of tandospirone dose-dependently improved dyskinesia-like symptoms. The administration did not lead to a rebound symptom at any of the dosages.

Example 7: Evaluation of Long-Term Motor Complications Under Continuous Subcutaneous Infusion of Tandospirone The sustainability of efficacy of tandospirone on dyskinesia-like symptoms was evaluated by continuous subcutaneous infusion of tandospirone to PD-LID rat model over 2 weeks.

(Testing Method)

A levodopa containing solution was repeatedly administered to 6-0HDA-lesioned rats for 3 weeks or more to observe and evaluate the behavior in the same manner as Example 5. Individuals with a total AIMs score of less than 15 were excluded from the test as not manifesting a dyskinesia-like symptom. The behavior was observed and evaluated before the drug evaluation date. The rats were assigned to each dosing group by using the 3 hour dyskinesia-like symptom (AIMs) score, Locomotive behavior score, and rat body weight as indicators, which were used for evaluation of drugs.

Tandospirone citrate was dissolved into 1 M hydrochloric acid (Nacalai Tesque) and diluted with saline and adjusted to a concentration of 60 mg/mL (concentration of citrate). The prepared solution was used after injection into an ALZET® Osmotic Pump MODEL 2ML2 (4.53 µL/hour; DURECT) for releasing a drug solution at a stable rate for 2 weeks.

An osmotic pump injected with tandospirone citrate or solvent was implanted under the skin of rats in each group with n=8. After 4 hours, a levodopa containing solution was administered to observe and evaluate the behavior (day 0 of implanting the pump). Once daily repeated administration of levodopa containing solution was continued thereafter. The behavior was also observed and evaluated on day 13 of implanting the pump. After each observation and evaluation of behavior, blood was collected from half of the rats (n=4) in the tandospirone administration group to analyze the plasma tandospirone concentration.

Figure 11A:
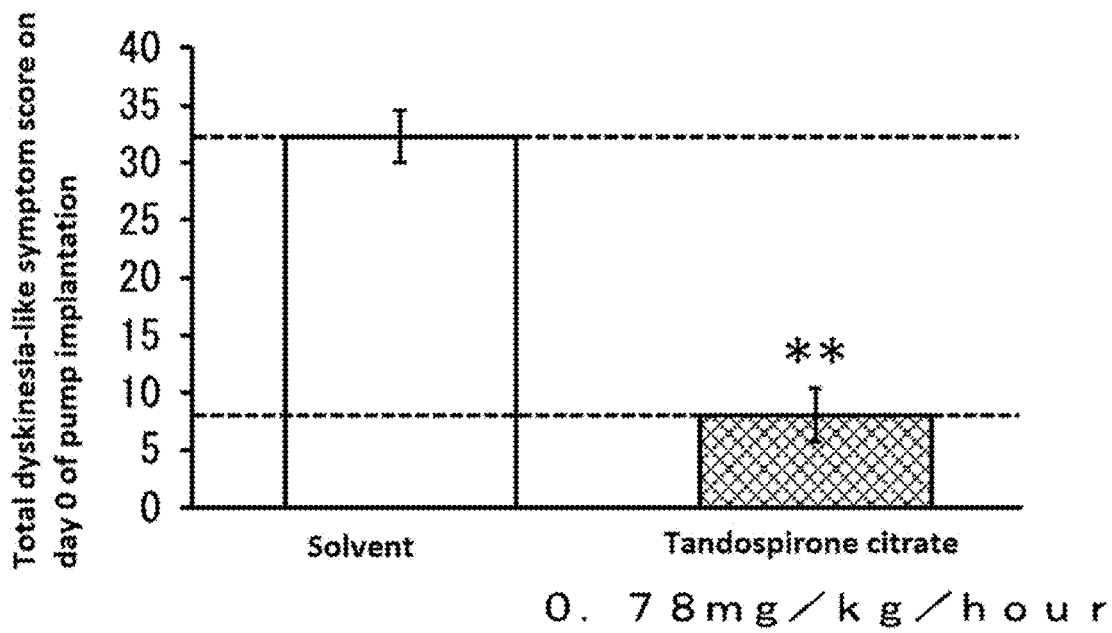
FIGS. 11A-11B show evaluation of long-term improvement in dyskinesia-like symptoms upon continuous subcutaneous infusion of tandospirone in Example 7. An osmotic pump injected with tandospirone citrate or solvent was implanted under the skin of rats in each group with n=8. After 4 hours, a levodopa containing solution was administered to observe and evaluate the behavior (day 0 of implanting the pump) (FIG. 11A). Once daily repeat administration of levodopa containing solution was continued thereafter. The behavior was also observed and evaluated on day 13 of implanting the pump (FIG. 11B). The results are indicated in terms of mean value±standard error of the total dyskinesia-like symptom (AIMs) scores in 3 hours. The test results were statistically analyzed using Wilcoxon rank sum test using the total AIMs score as a parameter. ** indicates $p<0.01$, meaning that there is a significant difference compared to the solvent administration group. After each observation and evaluation of behavior, blood was collected from half of the rats (n=4) in the tandospirone administration group to analyze the plasma tandospirone concentration.
Figure 11B:
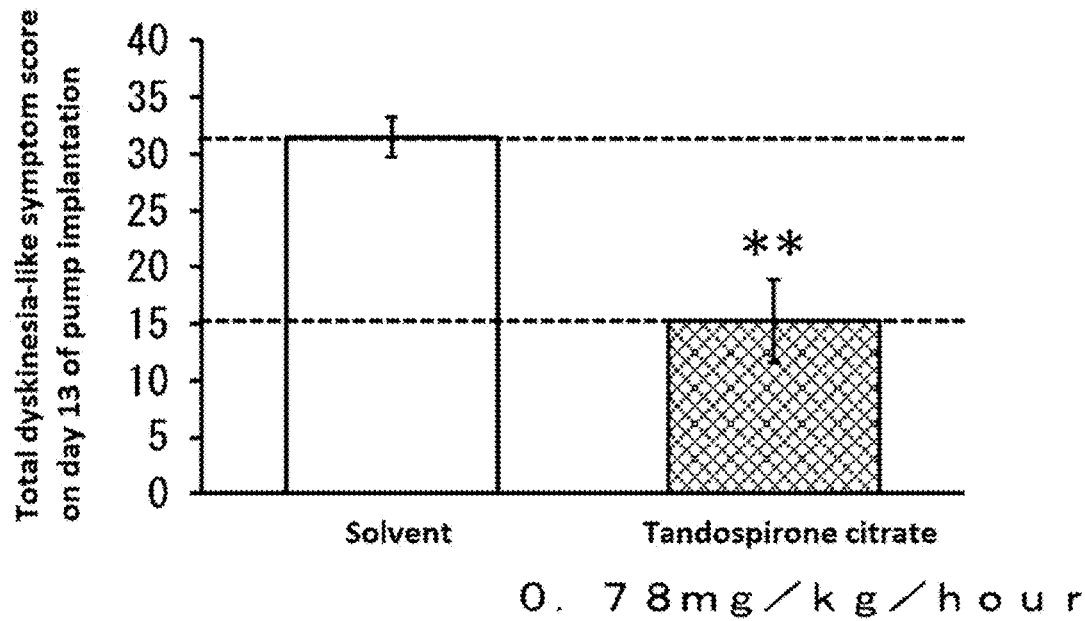

The results in FIGS. 11A and 11B are indicated in terms of mean value±standard error of the total dyskinesia-like symptom (AIMs) scores in 3 hours. The test results were statistically analyzed using Wilcoxon rank sum test using the total AIMs score as a parameter. ** indicates p<0.01, meaning that there is a significant difference compared to the solvent administration group.

(Results)

Significant improvement in dyskinesia-like symptoms was observed compared to the solvent group on day 0 of implanting the pump from continuous subcutaneous infusion of tandospirone citrate (60 mg/mL: mean 0.78 mg/kg/hour as tandospirone citrate) (FIG. 11A). The mean value of the plasma tandospirone concentrations (value converted in terms of free form) measured after the completion of observation and evaluation of behavior was 281 ng/mL. A significant improvement in dyskinesia-like symptoms relative to the solvent group was also observed on day 13 of implanting the pump (FIG. 11B). The mean value of the plasma tandospirone concentrations (value converted in terms of free form) measured after the completion of observation and evaluation of behavior was 143 ng/mL.

In view of the results, the effect of improving PD-LID symptoms was sustained even after continuous subcutaneous infusion of tandospirone for 13 days.

Example 8: Evaluation of the Effect of Continuous Subcutaneous Infusion of Tandospirone on Prevention/Suppression of Motor Complications (Testing method)

Tandospirone citrate was dissolved into 1 M hydrochloric acid (Nacalai Tesque) and diluted with saline and adjusted to a concentration of 60 mg/mL or 30 mg/mL. The prepared solution was used after injection into an ALZET® Osmotic Pump MODEL 2ML2 (4.53 µL/hour; DURECT).

6-OHDA-lesioned rats were assigned to each administration group using the number of apomorphine hydrochloride hemihydrate induced rotations and body weight as indicators. An osmotic pump injected with tandospirone citrate or solvent was implanted under the skin of rats on the day after starting repeated administration of a levodopa containing solution with the same composition as Example 2. The behavior was observed and evaluated using the same method as Example 2 on day 3, 5, 9, and 15 after starting the repeated administration of levodopa. The osmotic pump implanted subcutaneously was retrieved after the observation and evaluation of behavior on day 15. The behavior was also observed and evaluated on the following day (day 16 of repeated administration of levodopa).

Figure 12A:
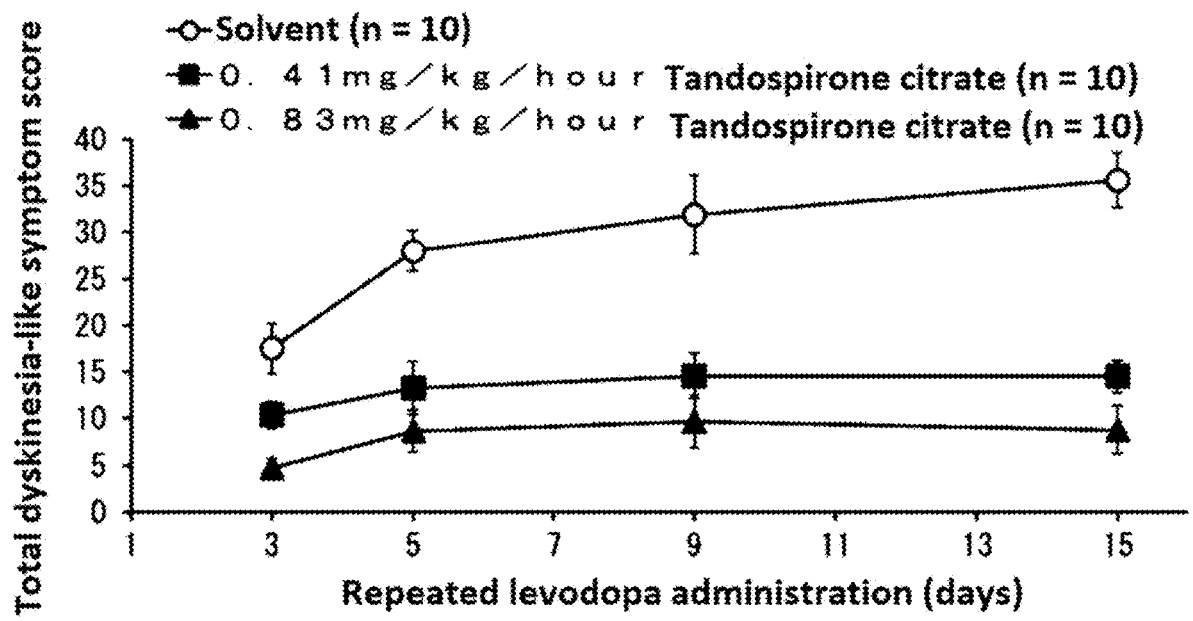
FIGS. 12A-12B show evaluation of the effect of preventing/suppressing dyskinesia-like symptoms upon continuous subcutaneous infusion of tandospirone in Example 8. 6-OHDA-lesioned rats were assigned to each administration group using the number of apomorphine hydrochloride hemihydrate induced rotations and body weight as indicators. An osmotic pump injected with tandospirone citrate or solvent was implanted under the skin of rats on the day after starting repeated administration of a levodopa containing solution with the same composition as Example 2. The behavior was observed and evaluated using the same method as Example 2 on day 3, 5, 9, and 15 after starting the repeated administration of levodopa. The osmotic pump implanted subcutaneously was retrieved after the observation and evaluation of behavior on day 15. The results of observing and evaluating behavior on the following day (day 16 of repeated administration of levodopa) are also shown. The results are indicated in terms of mean value±standard error of the total dyskinesia-like symptom (AIMs) scores in 3 hours.
Figure 12B:
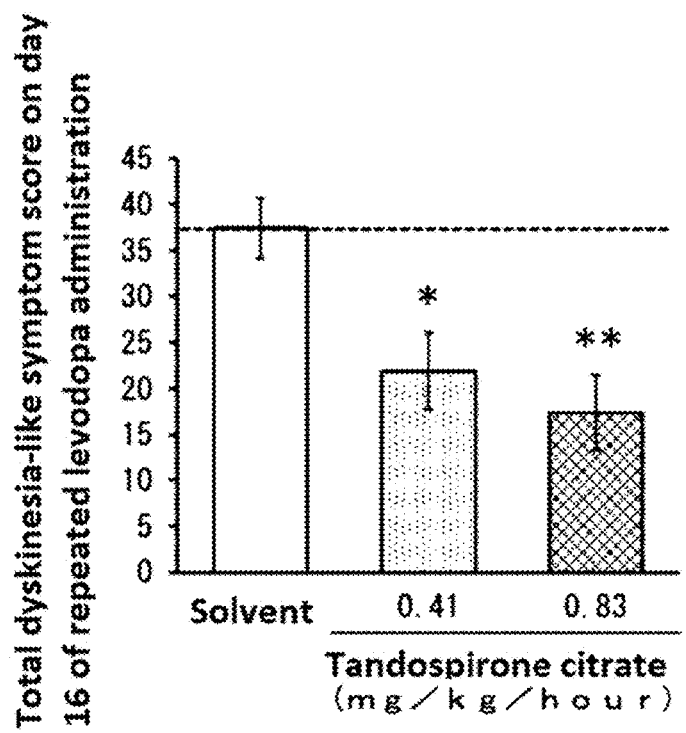

The results in FIGS. 12A and 12B are indicated in terms of mean value±standard error of the total dyskinesia-like symptom (AIMs) scores in 3 hours. The test results were statistically analyzed by comparison with the solvent administration group using Steel test with the total AIMs score on day 16 of repeated levodopa administration as the parameter. * indicates p<0.05 and ** indicates p<0.01, meaning that there is a significant difference compared to the solvent administration group.

(Results)

Continuous subcutaneous infusion of tandospirone citrate (30 mg/mL: mean of 0.41 mg/kg/hour or 60 mg/mL: mean of 0.83 mg/kg/hour) suppressed the increase in total AIMs score associated with repeated administration of levodopa compared to the solvent group (FIG. 12A). The total AIMs score was significantly lower in the group administered with tandospirone citrate compared to the solvent group on the day after the completion of tandospirone citrate administration (FIG. 12B).

In view of the results, continuous subcutaneous infusion of tandospirone prevented onset of PD-LID, and the effect thereof was also sustained to the day after the final dose of tandospirone.

Comparative Example 1: Evaluation of Oral Administration of Tandospirone on Dyskinesia Symptoms (Testing Method)

The behavior was observed and evaluated using the same method as Example 2. Tandospirone citrate was suspended in 0.5% methylcellulose solution and orally administered to rats. After 5 minutes, a levodopa containing solution was intraperitoneally administered, and the behavior was observed and evaluated. The results in the drawings are indicated in terms of mean value 1 standard error. The test results were statistically analyzed by comparison with the solvent administration group by Steel test using the total dyskinesia-like symptom (AIMs) score in 3 hours and total dyskinesia-like symptom score in 100 to 180 minutes as parameters. * indicates $p<0.05$, meaning that there is a significant difference.

(Results)

(1) Dyskinesia-Like Symptom

Figure 13A:
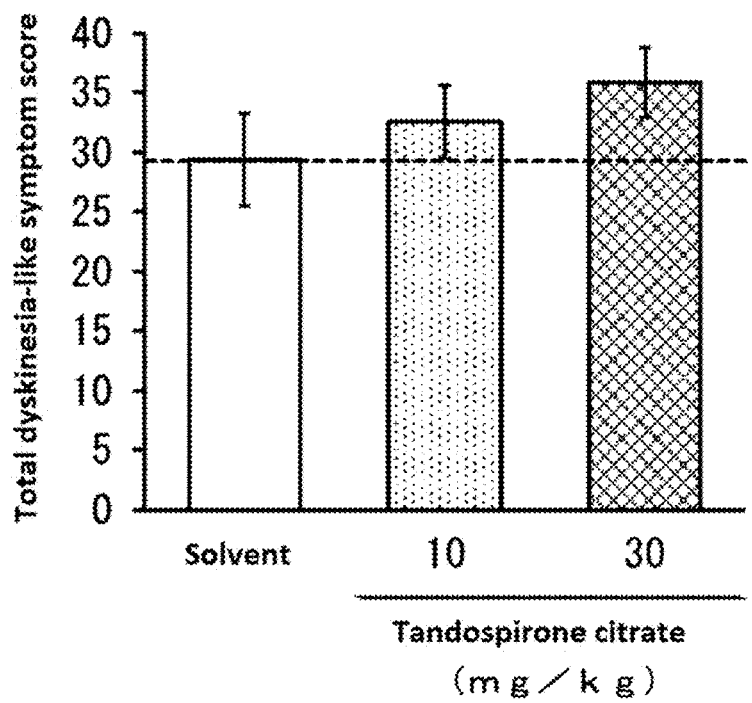
FIGS. 13A-13B show evaluation of oral administration of tandospirone on dyskinesia symptoms in Comparative Example 1. The behavior was observed and evaluated using the same method as Example 2. Tandospirone citrate (10 mg/kg, 30 mg/kg as citrate concentration) was suspended in 0.5% methylcellulose solution and orally administered to rats. After 5 minutes, a levodopa containing solution was intraperitoneally administered, and the behavior was observed and evaluated. The results in the drawings are indicated in terms of mean value±standard error. The test results were statistically analyzed by comparison with the solvent administration group using the Steel test with the total dyskinesia-like symptom (AIMs) score in 3 hours (FIG. 13A) and total dyskinesia-like symptom score in 100 to 180 minutes (FIG. 13B) as parameters. * indicates $p<0.05$, meaning that there is a significant difference.
Figure 14A:
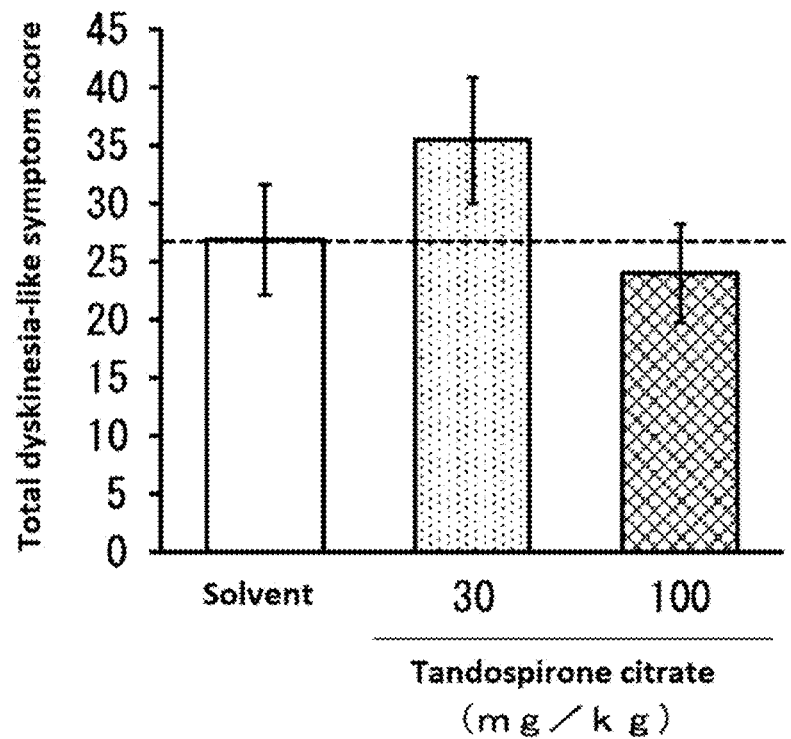
FIGS. 14A-14B show evaluation of oral administration of tandospirone on dyskinesia symptoms in Comparative Example 1. The behavior was observed and evaluated using the same method as Example 2. Tandospirone citrate (30 mg/kg, 100 mg/kg as citrate concentration) was suspended in 0.5% methylcellulose solution and orally administered to rats. After 5 minutes, a levodopa containing solution was intraperitoneally administered, and the behavior was observed and evaluated. The results in the drawings are indicated in terms of mean value±standard error. The test results were statistically analyzed by comparison with the solvent administration group using the Steel test with the total dyskinesia-like symptom (AIMs) score in 3 hours (FIG. 14A) and total dyskinesia-like symptom score in 100 to 180 minutes (FIG. 14B) as parameters. * indicates p<0.05, meaning that there is a significant difference.

In the tandospirone citrate (10, 30, or 100 mg/kg as citrate concentration) orally administered groups, a significant change in the total AIMs score was not observed in comparison to the solvent administration group (FIGS. 13A and 14A). The results suggest that the PD-LID cannot be improved with a tandospirone oral administration formulation.

Figure 13B:
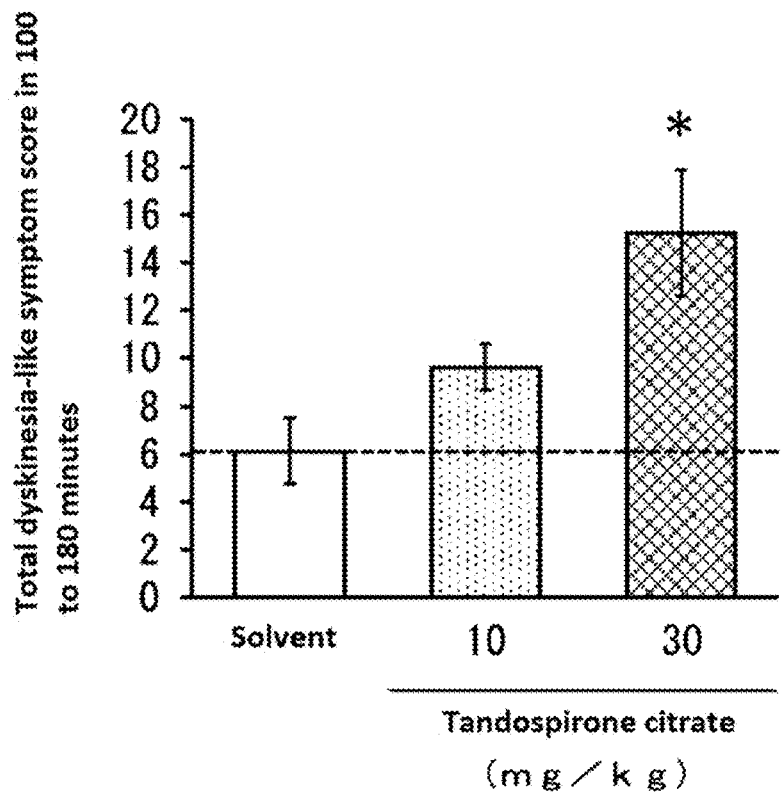
Figure 14B:
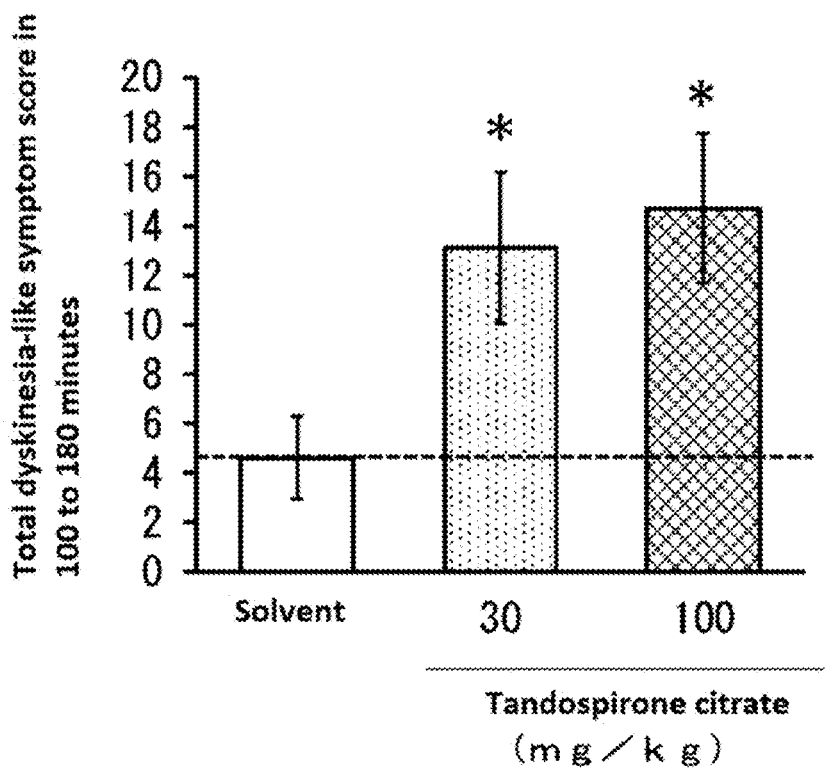

At 120 to 140 minutes after levodopa administration, dyskinesia-like symptoms subsided in the solvent administration group, but a clear dyskinesia-like symptom (mean AIMs score of 2 or greater) was observed in the tandospirone citrate oral administration group (30 or 100 mg/kg). Furthermore, when the solvent administration group and tandospirone citrate oral administration group were compared using the total dyskinesia-like symptom score in 100 to 180 minutes as the indicator, a significant increase in the total AIMs score was observed in the tandospirone citrate oral administration group (30 or 100 mg/kg) in comparison to the solvent administration group (FIGS. 13B and 14B). The result suggests the potential of manifestation of a phenomenon with delayed manifestation and exacerbation of dyskinesia-like symptoms (rebound symptom of dyskinesia) in a formulation for oral administration of tandospirone.

In view of the above, an improvement in dyskinesia symptoms was not observed in PD-LID rat models in the tandospirone oral administration group (Table 3-(i)). A rebound symptom of dyskinesia was observed in high dosage oral administration group (Table 3-(ii)). In view of the results, oral administration of tandospirone has an insufficient effect of improving dyskinesia, and has a risk of manifestation of a rebound symptom. Therefore, combined therapy with a levodopa formulation is possibly unsuitable.

As for the duration of action of levodopa without a dyskinesia symptom (ON time without dyskinesia) in PD-LID rat models, prolongation of action time was observed in high dose oral administration (100 mg/kg), but not at a low dose. Meanwhile, an effect of improvement was observed under either dosing conditions with transdermal administration. The time of prolongation was longer than oral administration under transdermal administration condition 2 (Table 3-(iii)). These results suggest that the therapeutic effect of tandospirone oral administration on motor complications is limited, and tandospirone transdermal administration is preferred.

Table 3

Comparison of action time related scores for transdermal and oral administration

| | Dosage (mg/kg) | (i) Degree of improvement in indicator of dyskinesia symptom | (ii) Indicator of rebound symptom of dyskinesia | (iii) Duration of action of levodopa without dyskinesia symptom (ON time without dyskinesia) |
|---|---|---|---|---|
| Transdermal administration (Condition 1) (Example 2) | 37 | Improvement 17.7 | No effect | Prolongation 21.7 min |
| Transdermal administration (Condition 2) (Example 2) | 4 5 | Improvement 27.1 | No effect | Prolongation 77.8 min |
| Oral administration (Comparative Example 1) | 6.7 | Ineffective | No effect | Ineffective |
| Oral administration (Comparative Example 1) | 20 | Ineffective | Exacerbation −9.1 (FIG. 7) −8.5 (FIGS. 8A-8B) | Ineffective |
| Oral administration (Comparative Example 1) | 67 | Ineffective | Exacerbation −10.1 | Prolongation 51.8 min |

(1) The total dyskinesia-like symptom (AIMs) score in three hours used as an indicator of dyskinesia symptoms (*1), (2) the total dyskinesia-like symptom score in 100 to 180 minutes used as an indicator of a rebound symptom of dyskinesia (*2), and (3) rotational behavior time without dyskinesia (*3) were compared. The dosage was described as a numerical value converted in terms of tandospirone free form. Numerical values were filled in only for indicators found to have a significant difference.

(*1) Total dyskinesia-like symptom (AIMs) score in 3 hours=(total dyskinesia-like symptom (AIMs) score for placebo tape agent or solvent administration group)−(total dyskinesia-like symptom (AIMs) score for tandospirone administration group)

(*2) Total dyskinesia-like symptom score in 100 to 180 minutes=(total dyskinesia-like symptom score in 100 to 180 minutes for placebo tape agent or solvent administration group)−(total dyskinesia-like symptom score in 100 to 180 minutes for tandospirone administration group)

(*3) Rotational behavior time without dyskinesia=rotational behavior time during which a dyskinesia-like symptom is not found Comparative Example 2: Evaluation of Tandospirone Metabolite on Dyskinesia Symptom The effect of a tandospirone metabolite 1-(2-Pyrimidyl) piperazine (hereinafter, also referred to as "1-PP") on dyskinesia-like symptoms was evaluated.

(Testing Method)

The behavior was observed and evaluated using the same method in Example 2. 1-PP dihydrochloride (Tokyo Chemical Industry) was dissolved in saline and subcutaneously administered to rats. After 5 minutes, a levodopa containing solution was intraperitoneally administered to observe and evaluate the behavior. The results in the drawings are indicated in terms of mean value±standard error. The test results were statistically analyzed by comparison with the solvent administration group by Steel test by using the total dyskinesia-like symptom (AIMs) score in 3 hours and total dyskinesia-like symptom score in 100 to 180 minutes as parameters.

(Results)

Figure 15A:
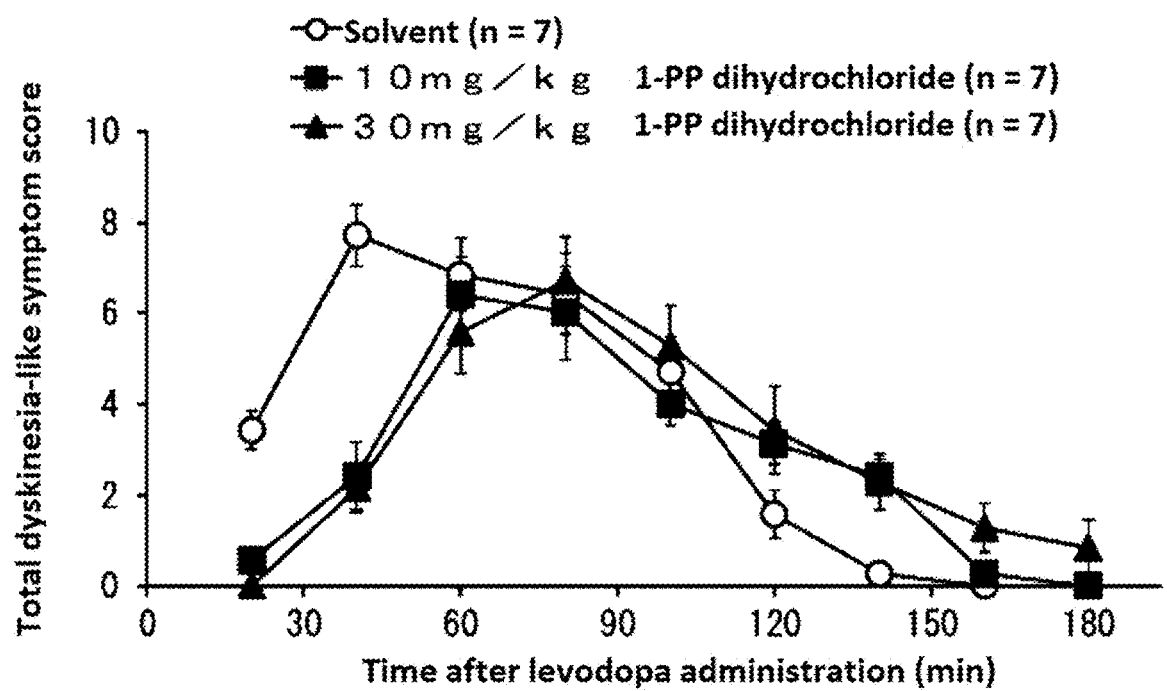
FIGS. 15A-15C show evaluation of tandospirone metabolite on dyskinesia symptoms in Comparative Example 2. The behavior was observed and evaluated using the same method in Example 2. 1-PP dihydrochloride (Tokyo Chemical Industry) was dissolved in saline and subcutaneously administered to rats (10, 30 mg/kg). After 5 minutes, a levodopa containing solution was intraperitoneally administered to observe and evaluate the behavior (FIG. 15A). The results in the drawings are indicated in terms of mean value±standard error. The test results were statistically analyzed by comparison with the solvent administration group using the Steel test with the total dyskinesia-like symptom (AIMs) score in 3 hours (FIG. 15B) and total dyskinesia-like symptom score in 100 to 180 minutes (FIG. 15C) as parameters.
Figure 15B:
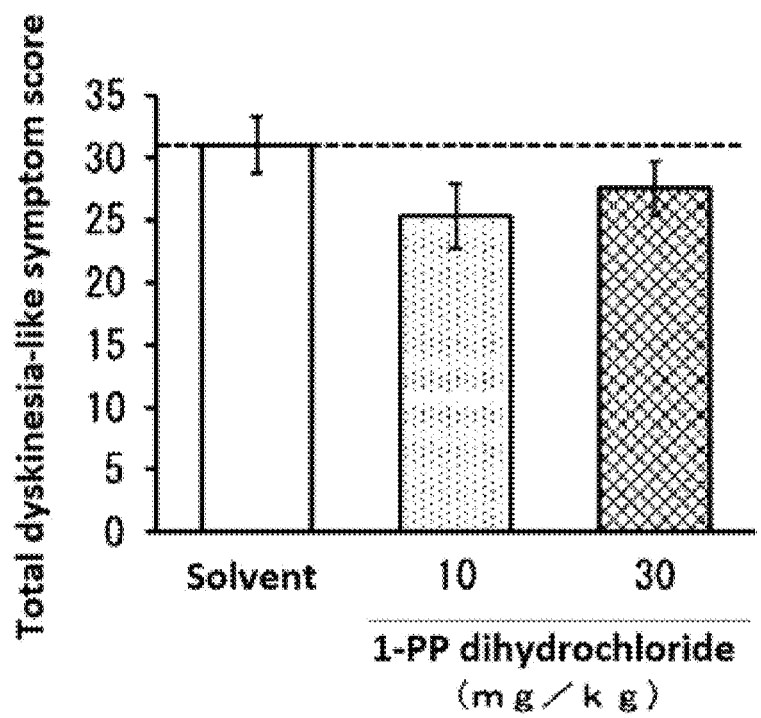

A significant change in the total AIMs score was not found in the 1-PP dihydrochloride (10 or 30 mg/kg) subcutaneous administration group, relative to the solvent administration group (FIGS. 15A and 15B).

Figure 15C:
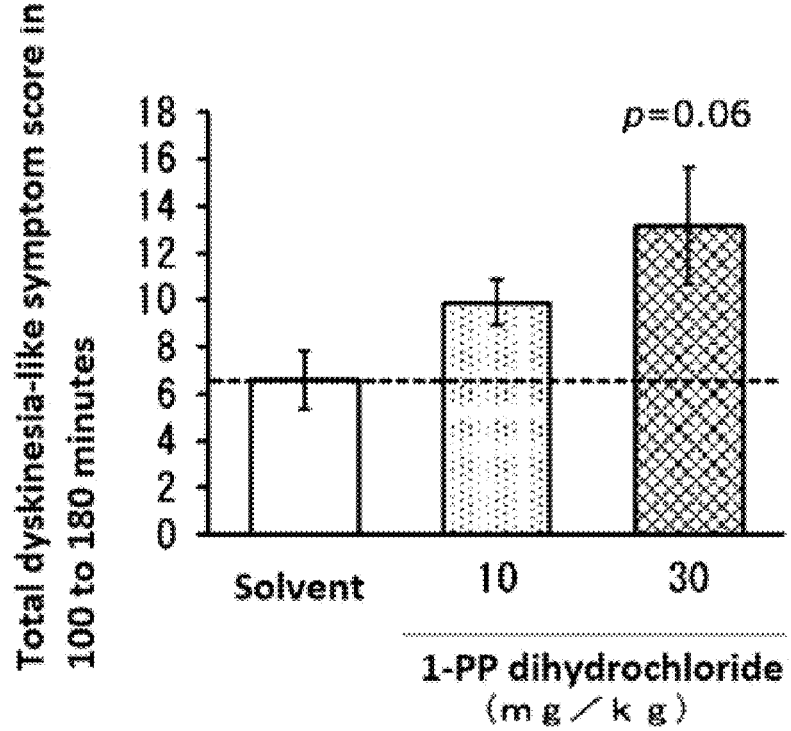

At 120 to 140 minutes after administration of levodopa, a clear dyskinesia-like symptom (mean AIMs score of 2 or greater) was observed in the 1-PP dihydrochloride subcutaneous administration group (10 or 30 mg/kg). When the solvent administration group and the 1-PP dihydrochloride administration group were compared by using the total dyskinesia-like symptom score in 100 to 180 minutes as an indicator, an increasing trend in the total AIMs score, albeit not significant, was observed in the 1-PP dihydrochloride administration group relative to the solvent administration group (FIG. 15C). The result suggests the potential of tandospirone metabolite 1-PP inducing a rebound symptom of dyskinesia.

The result suggests the potential of a rebound symptom of dyskinesia under administration conditions generating the tandospirone metabolite 1-PP. In other words, for tandospirone, a method of administration that can suppress the generation of 1-PP has less effect on rebound symptoms of dyskinesia and is preferable.

(Reference Example: Checking X-Ray Powder Diffraction Patterns of Tandospirone Free Form, Tandospirone Citrate (Hydrate), and Tandospirone Citrate (Anhydrate))

This Reference Example checked the X-ray powder diffraction patterns of a tandospirone free form, tandospirone citrate (hydrate), and tandospirone citrate (anhydrate)

X-ray powder diffraction was measured under the following conditions.

*Apparatus: X'pert-MPD (Spectris)
*X-ray: Cu K$\alpha_1$/45 kV/40 mA
*Irradiation width: 15 mm divergence slit: automatic
*Step size: 0.017°
*Scanning range: 4 to 40° (2θ)
*Integration time: 100 seconds/step
*Sample plate: non-reflective silicone sample plate The results are shown in FIG. 16.

Example 9: Clinical Test on Pharmacokinetics of Tandospirone Tape Agent

This Example tested and analyzed the pharmacokinetics such as blood concentration of tandospirone in a clinical test.

(Materials and Methods)

This Example performed measurement, prediction and analysis on plasma tandospirone concentration based on the following method.

(1) A single 24-hour dose of tandospirone tape agent (free form content of 4.4 mg, 8.8 mg, and 17.6 mg) was transdermally administered to the pectoral region of 9 healthy Japanese male subjects, and the plasma tandospirone concentration was measured.

(2) For 35.2 mg, 88 mg, and 176 mg, the plasma tandospirone concentration was predicted based on the results for 17.6 mg. The steady state plasma tandospirone concentration was also predicted using Phoenix® WinNonlin® (Certara).

(Formulations Used)

As the tandospirone tape agent, an acrylic adhesive tape agent, which has a sheet-like structure consisting of three layers (a support, adhesive layer, and a detachable film (liner)) and comprises tandospirone (free form) as an active ingredient, was used. The amount of drug penetration from a 24 hour application was about ⅓ to ½ of the tandospirone free form content (drug dosage) in the tape agent. Although not wishing to be bound by any theory, it is understood in the art that if the amount of drug penetration upon 24 hour application is the same, any tape agent can achieve a similar plasma tandospirone concentration as the present Example.

(Results)

FIGS. 17A to 19B show the results of this Example (plasma tandospirone concentration and prediction under steady state). This data is based on preliminary analysis results.

Figure 17A:
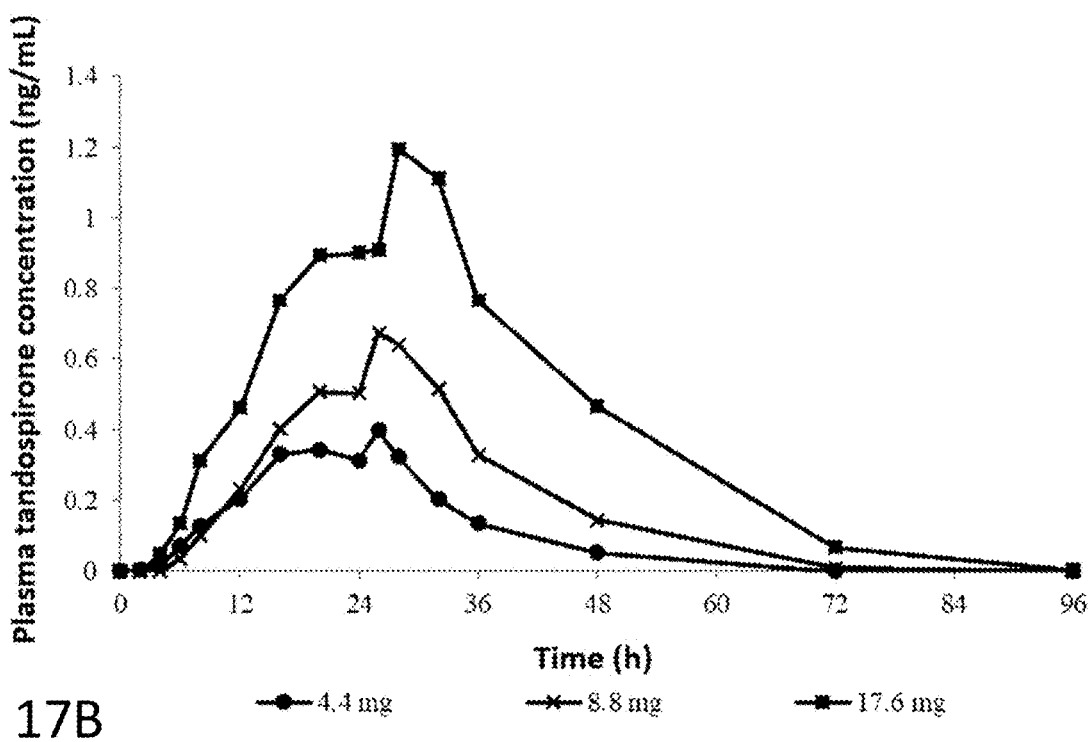
FIG. 17A shows results in Example 9, which shows the change in the concentration of plasma tandospirone free form upon transdermal administration of a single 24-hour dose of a tandospirone tape agent (mean value).
Figure 17B:
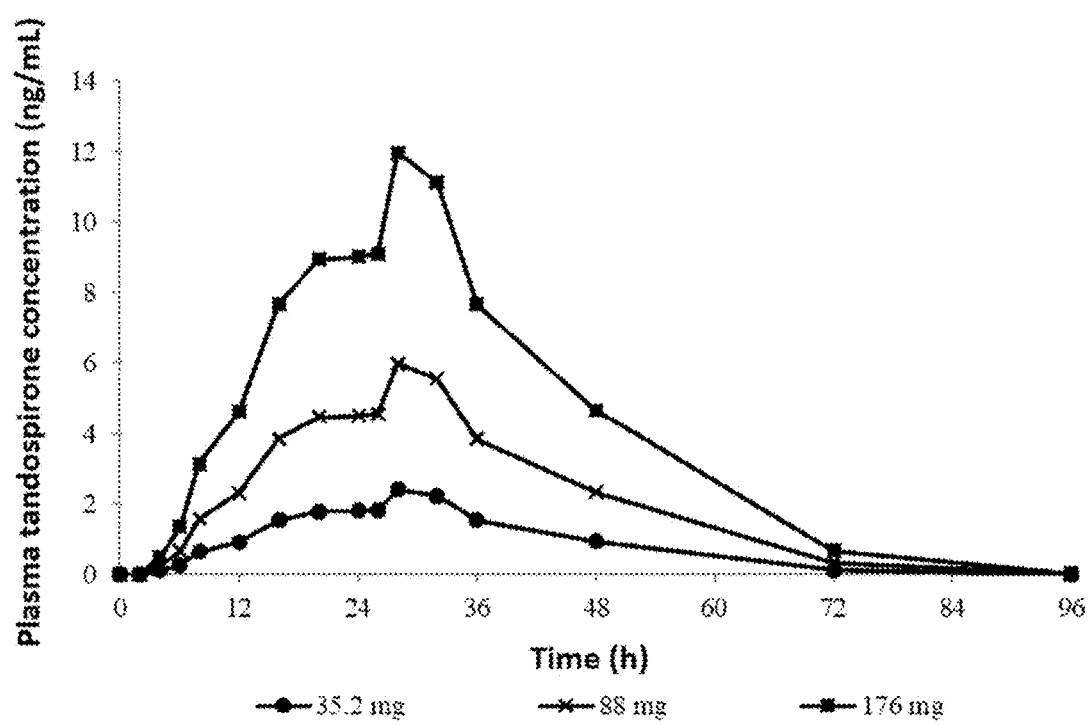
FIG. 17B shows values of prediction and analysis from actual measurement values for 17.6 mg.

FIGS. 17A and 17B show the change in the concentration of plasma tandospirone upon transdermal administration of a single 24-hour dose of a tandospirone tape agent used in this Example (mean value) (the plasma tandospirone concentration is a concentration as a tandospirone free form). FIG. 17A shows the actual measurement value based on a preliminary analysis result for plasma tandospirone concentrations for 4.4 mg, 8.8 mg, and 17.6 mg. FIG. 17B shows values of prediction and analysis from actual measurement values for 17.6 mg.

Figure 18A:
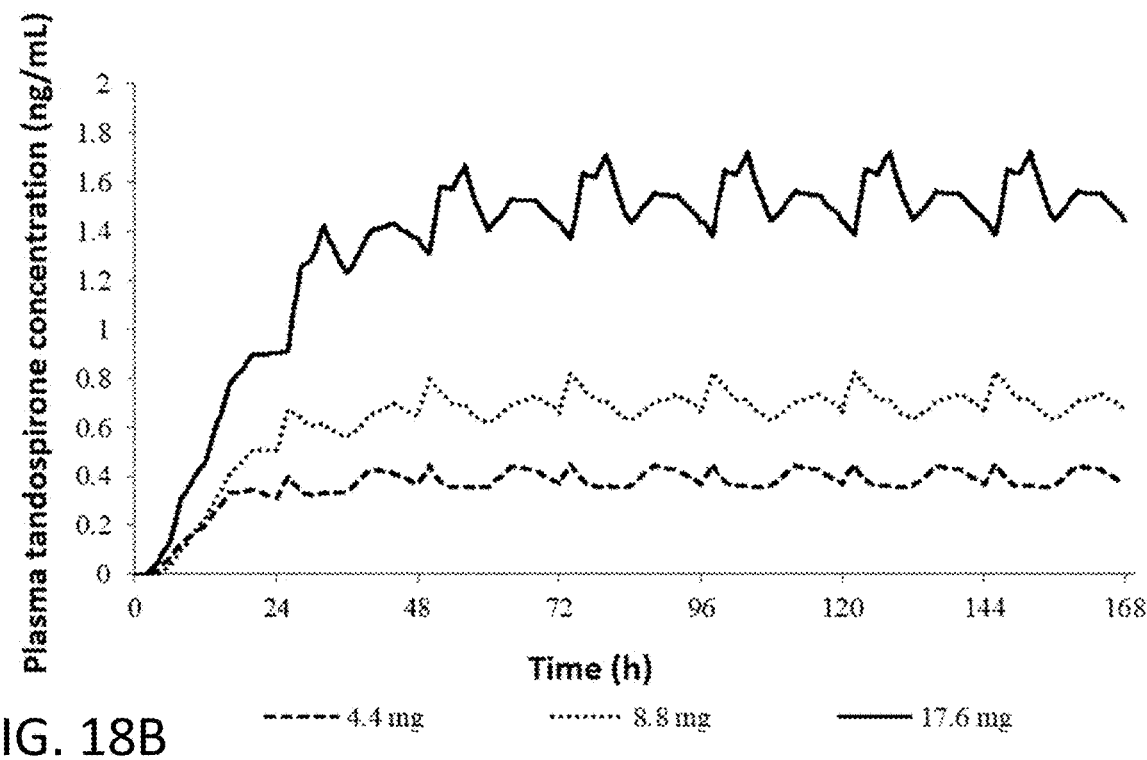
FIGS. 18A-18B also show results in Example 9, which shows a predicted value for the change in the concentration of plasma tandospirone upon once daily repeated transdermal administration of a tandospirone tape agent.
Figure 18B:
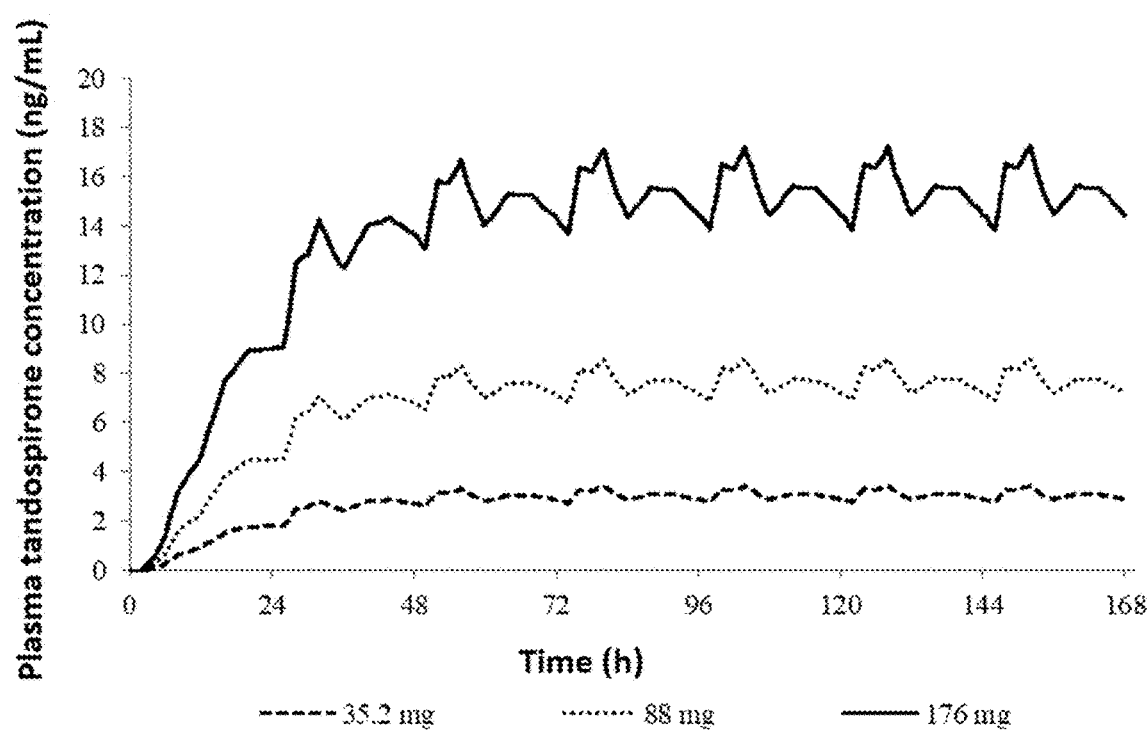

FIGS. 18A and 18B show a predicted value for the change in the concentration of plasma tandospirone upon once daily repeated transdermal administration of a tandospirone tape agent of this Example. The results shown in FIG. 18A show values predicted based on the plasma tandospirone concentrations upon a 24-hour single administration of 4.4 mg, 8.8 mg, and 17.6 mg. The results shown in FIG. 18B show values predicted based on the plasma tandospirone concentration upon a 24-hour single administration of 17.6 mg.

Figure 19A:
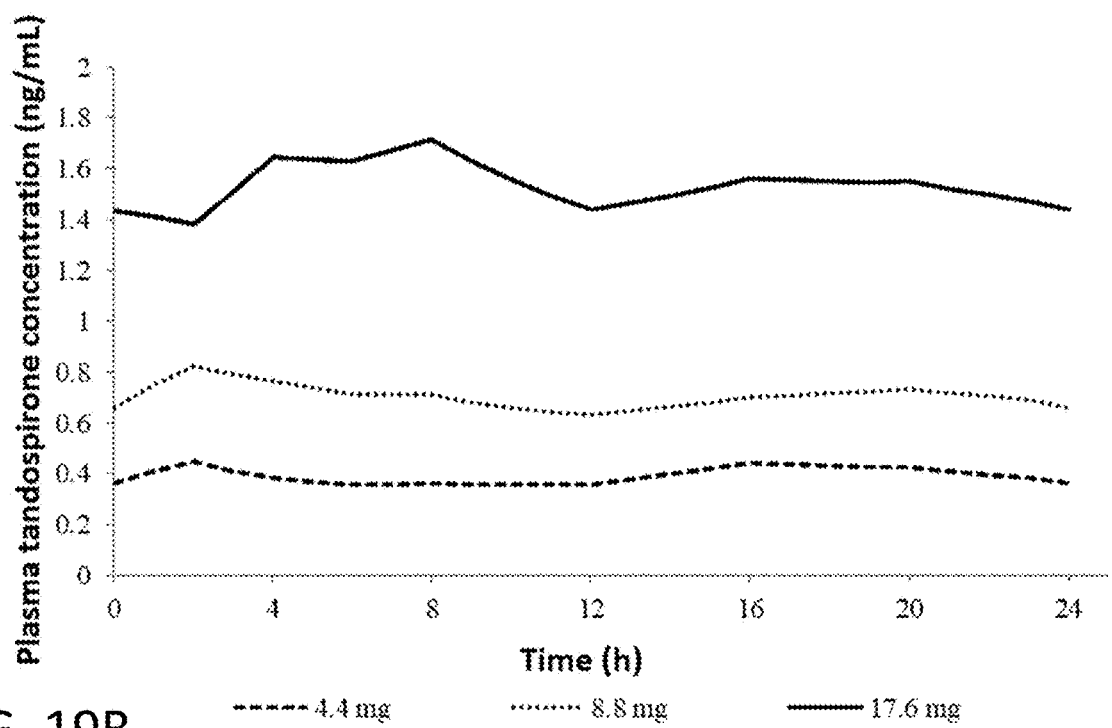
FIGS. 19A-19B also shows results in Example 9, which shows a predicted value for the change in the concentration of plasma tandospirone in a steady state upon once daily repeated transdermal administration of a tandospirone tape agent.
Figure 19B:
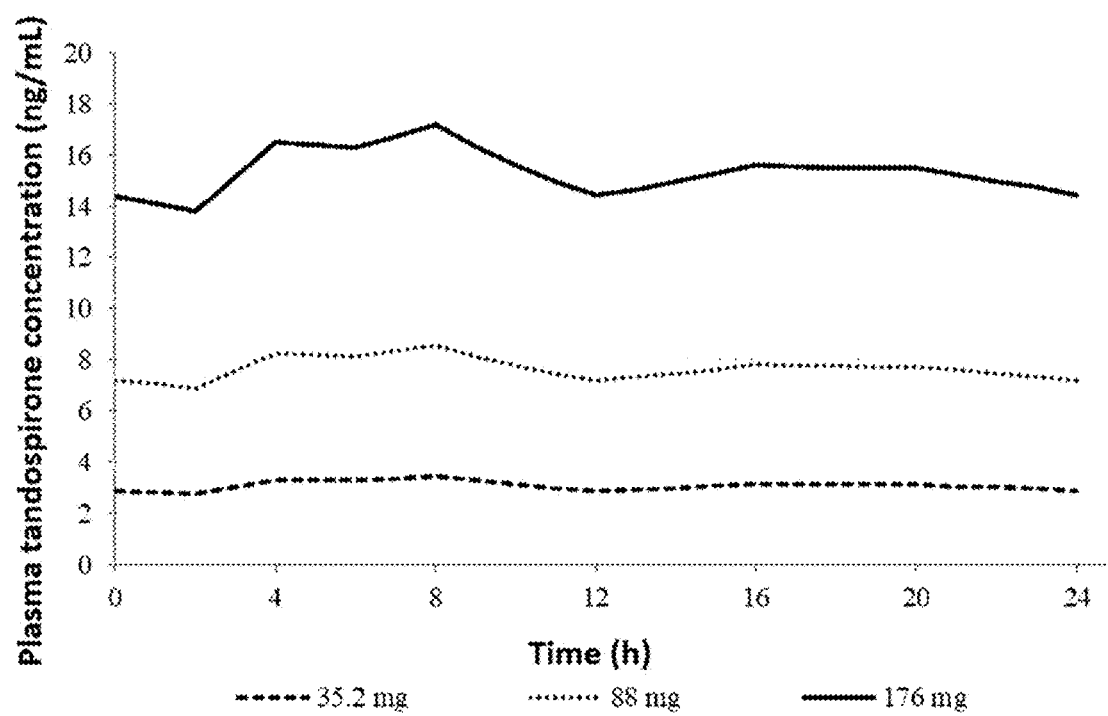

FIGS. 19A and 19B show a predicted value for the change in the concentration of plasma tandospirone in a steady state upon once daily repeated transdermal administration of a tandospirone tape agent in this Example. FIG. 19A is a prediction based on the plasma tandospirone concentration upon a 24-hour single administration of 4.4 mg, 8.8 mg, and 17.6 mg. FIG. 19B is a prediction based on the plasma tandospirone concentration upon a 24-hour single administration of 17.6 mg.

(Discussion)

It is understood that motor fluctuations can be suppressed by using a daily dose (drug dosage per day) of 4 mg to 180 mg of active ingredient.

Example 10: Study in MPTP Induced PD-LID Rhesus Monkey Model

This Example studied the effect of improvement of PD-LID by transdermal administration of tandospirone in a rhesus monkey model with PD-LID induced with 1-methyl-4-phenyl-1,2,3,6-tetrahydropyridine (MPTP) that is used to create a Parkinson's disease animal model.

(Materials and Methods)

MPTP induced Parkinson's disease levodopa induced dyskinesia (PD-LID) rhesus monkey models were created as follows. To male rhesus monkeys (Hamri Co., Ltd.), 0.4 or 0.6 mg/kg of MPTP was administered once or twice a week continuously until Parkinson's disease symptoms manifested stably, and then levodopa (20 or 30 mg/kg) was administered once or twice a week continuously until dyskinesia manifested stably to create PD-LID rhesus monkey models.

levodopa/Benserazide (levodopa at 22 mg/kg, and Benserazide at ¼ the weight of levodopa) was orally administered to the PD-LID rhesus monkey models, and dyskinesia symptoms were evaluated every 30 minutes from 5 minutes after administration for 150 minutes. A tandospirone containing paste or a tandospirone free placebo paste was transdermally administered to the monkey models. The back of the rhesus monkeys was shaved. A paste was applied to a 4 cm×10 cm area 19 hours before the test. The paste was covered with a tape and clean fabric, and the monkeys were fitted with a jacket. Dyskinesia was evaluated (dyskinesia score) by analyzing a video capturing the monkey models and giving scores by an evaluator experienced in behavioral evaluation. Dyskinesia scores were evaluated based on Revised non-human primate dyskinesia rating scale (J Neurosci 2001; 21: 6853-6861.) A score of 0 was given if dyskinesia was not observed at all; a score of 1 was given if dyskinesia was observed in less than 30% of the evaluation period, which is deemed as a mild dyskinesia; a score of 2 was given if dyskinesia was observed in 30% or more of the evaluation period but normal behavior was not inhibited, which is deemed as a moderate dyskinesia; a score of 3 was given if dyskinesia was observed in 30% or more and less than 70% of the evaluation period and normal behavior was inhibited, which is deemed as a significant dyskinesia; and a score of 4 was given if dyskinesia was observed in 70% or more of the evaluation period and normal behavior was inhibited, which is deemed as a severe dyskinesia. Systemic dyskinesia was also evaluated as a particularly severe dyskinesia. Systemic dyskinesia was defined as manifestation of dyskinesia at 4 or more of the face, right arm, left arm, body trunk, right leg, and left leg by referring to UDysRS, which is a clinical evaluation scale using dyskinesia by parts in the evaluation. A score of 1 was given if systemic dyskinesia was found in 30% or more of the evaluation period, and a score of 2 was given if systemic dyskinesia was found in 70% or more of the evaluation period.

(Results)

Figure 20A:
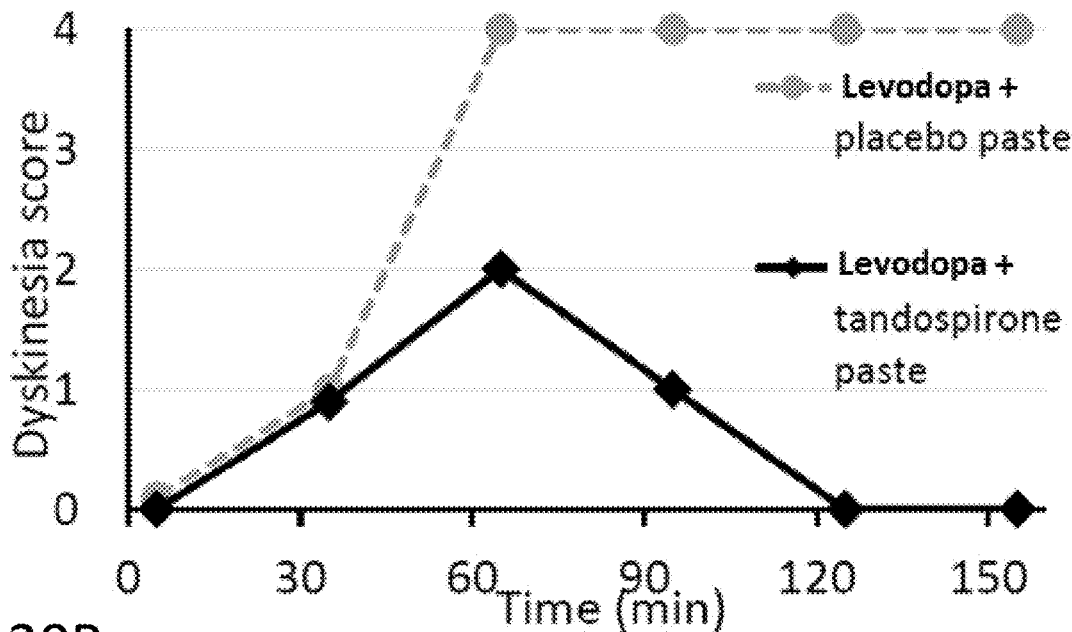
FIGS. 20A-20B show the results in Example 10.
Figure 20B:
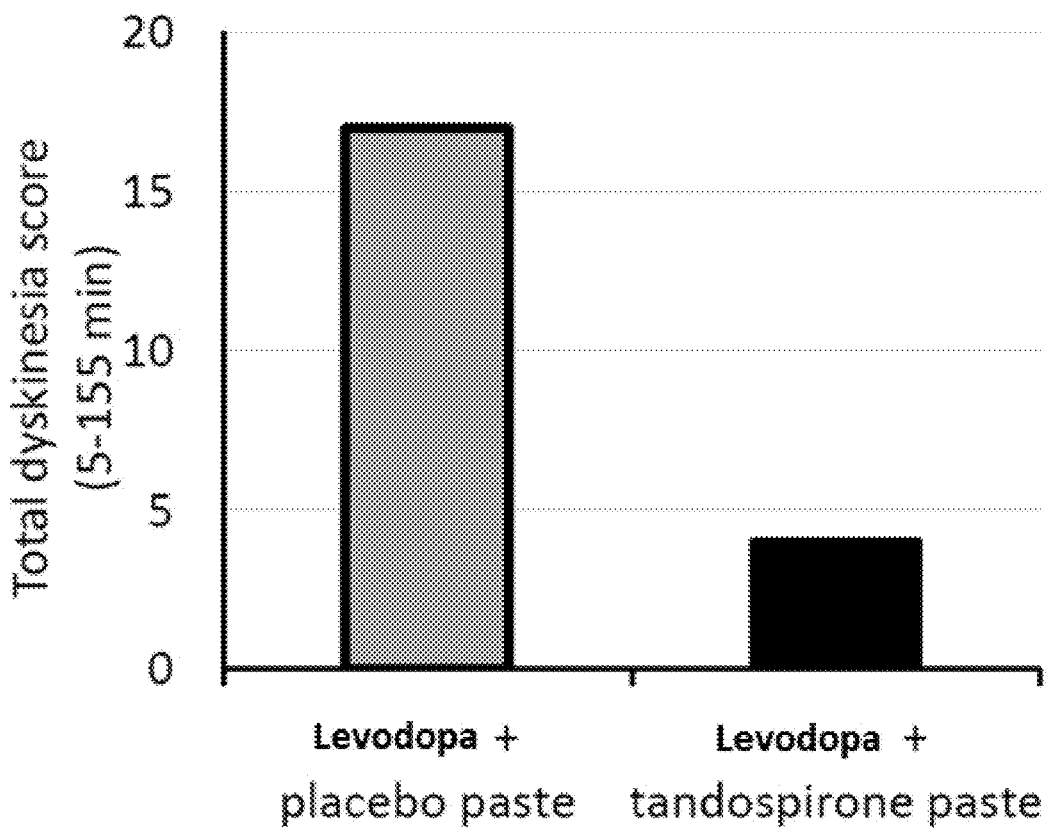

FIGS. 20A and 20B show the results of this Example (sustained suppression of development of dyskinesia symptoms in monkey models). levodopa/Benserazide (levodopa at 22 mg/kg, and Benserazide at ¼ the weight of levodopa) was orally administered to the PD-LID rhesus monkey models, and dyskinesia symptoms (dyskinesia score) were evaluated every 30 minutes from 5 minutes after levodopa/Benserazide administration for 155 minutes. A dyskinesia score of 4 was exhibited at 65 to 155 minutes after levodopa/Benserazide administration with placebo paste administration, while sustained suppression of the dyskinesia score was observed with administration of tandospirone containing paste (FIG. 20A). The total dyskinesia score during 155 minutes after levodopa/Benserazide administration was suppressed 76.5% (FIG. 20B).

The results show that a sustained effect of improving a dyskinesia symptom is found from transdermal administration of tandospirone in PD-LID rhesus monkey models.

Example 11: Demonstration in Clinical Protocol

The effect of improving PD-LID of the compound of the invention or the combined drug of the present disclosure can be confirmed by a clinical study in accordance with the method described in the following Reference Document 1 (amantadine P3) as clinical study with a suitable design that can evaluate PD-LID (Reference Document 1: JAMA Neurology 2017; 74 (8) 941-949; Reference Document 2: Movement Disorders 2015; 30 (19) 1343-1350).

More specifically, the effect of improving motor complications such as PD-LID or motor fluctuations can be confirmed by, for example, administering the tandospirone or a pharmaceutically acceptable salt or prodrug thereof of the invention or a combined drug of the present disclosure for a certain dosing period (examples thereof include, but are not limited to, 8 to 12 weeks) in 20-year-old or older patients diagnosed as having Parkinson's disease and comparing clinical evaluation scales such as UPDRS, MDS-UPDRS, UDysRS, CDRS, Rush DRS, AIMS, EQ-5D-5L, PDQ-39, CGI, or PGI before and after the dosing period, ON time or OFF time described in a patient diary, a scale calculated from locomotive movement information obtained from a wearable device such as an accelerometer and/or angular velocimeter, or the like.

The conditions such as the target patient, dosing period, dosage of agent, and evaluation method can be appropriately changed in the above test.

(Note)

As disclosed above, the present disclosure is exemplified by the use of its preferred embodiments. However, it is understood that the scope of the present disclosure should be interpreted solely based on the Claims. It is also understood that any patent, any patent application, and any other references cited herein should be incorporated herein by reference in the same manner as the contents are specifically described herein. The present application claims priority to Japanese Patent Application No. 2020-145967 filed on Aug. 31, 2020 with the Japan Patent Office. It is understood that the content thereof should be incorporated herein by reference in the same manner as the contents are specifically described herein.

INDUSTRIAL APPLICABILITY

A tandospirone formulation of the present disclosure is useful as a therapeutic drug that improves monitor complications such as motor fluctuations in Parkinson's disease.

What is claimed is:

1. A method of treating or improving motor fluctuations in Parkinson's disease, wherein the motor fluctuations are selected from the group consisting of wearing-off, on-off phenomenon, no-on phenomenon, delayed on phenomenon and a combination thereof, wherein the method comprises transdermally administering an effective amount of tandospirone or a pharmaceutically acceptable salt thereof to a subject in need thereof.

2. The method of claim 1, wherein the subject is undergoing drug therapy for Parkinson's disease.

3. The method of claim 1, wherein the subject is undergoing drug therapy selected from the group consisting of drug therapy for Parkinson's disease using a levodopa containing formulation, a levodopa metabolite inhibitor, or a dopamine receptor agonist and therapy using an adjunct agent for Parkinson's disease.

4. The method of claim 1, wherein the subject is undergoing dopamine replacement therapy for Parkinson's disease.

5. The method of claim 1, wherein the subject is undergoing levodopa therapy for Parkinson's disease.

6. The method of claim 1, wherein the method does not cause troublesome dyskinesia.

7. The method of claim 1, wherein the method does not exacerbate a dyskinesia symptom in Parkinson's disease.

8. The method of claim 1, wherein the method does not exacerbate a levodopa induced dyskinesia (PD-LID) symptom.

9. The method of claim 1, wherein the method does not cause a rebound symptom of levodopa induced dyskinesia (PD-LID).

10. The method of claim 1, wherein the method does not cause a troublesome dyskinesia symptom.

11. The method of claim 1, wherein the administration is accomplished with a transdermally administered formulation.

12. The method of claim 1, wherein a drug dosage of the tandospirone or a pharmaceutically acceptable salt thereof is 0.1 to 500 mg per day as a free form of tandospirone.

13. The method of claim 1, wherein a drug dosage of the tandospirone or a pharmaceutically acceptable salt thereof is 3 to 250 mg per day as a free form of tandospirone.

14. The method of claim 1, wherein an amount of drug penetration for the tandospirone or a pharmaceutically acceptable salt thereof is 0.1 to 100 mg per day as a free form of tandospirone.

15. The method of claim 1, wherein an amount of drug penetration for the tandospirone or a pharmaceutically acceptable salt thereof is 1 to 60 mg per day as a free form of tandospirone.

16. The method of claim 1, wherein the tandospirone or a pharmaceutically acceptable salt thereof is provided as a transdermally administered formulation, and a total applied area per dose is 1 to 100 cm$^2$.

17. The method of claim 1, wherein the tandospirone or a pharmaceutically acceptable salt thereof is provided as a transdermally administered formulation, and a total applied area per dose is 9 to 60 cm$^2$.

18. The method of claim 1, wherein the tandospirone or a pharmaceutically acceptable salt thereof is administered so that a human blood (plasma) tandospirone concentration is 0.1 to 15 ng/mL for 12 hours or longer per day; and/or 0.1 to 15 ng/mL for 8 to 16 hours after administration of the tandospirone or a pharmaceutically acceptable salt thereof.

19. The method of claim 1, wherein the tandospirone or a pharmaceutically acceptable salt thereof is administered so that an amount of change in striatal [$^{11}$C] raclopride receptor binding from before levodopa administration to 1 hour after administration (amount of change B/1 h) after administering the tandospirone or a pharmaceutically acceptable salt thereof is less than 10%.

20. The method of claim 1, wherein the tandospirone or a pharmaceutically acceptable salt thereof is provided as an adjunct of levodopa.

21. The method of claim 1, wherein the tandospirone or a pharmaceutically acceptable salt thereof is administered so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% after administration of the tandospirone or a pharmaceutically acceptable salt thereof.

22. The method of claim 1, wherein the size of the formulation ranges from 1 cm$^2$ to 160 cm$^2$.

23. The method of claim 1, wherein the size of the formulation ranges from 9 cm$^2$ to 160 cm$^2$.

24. The method of claim 1, wherein the method comprises reducing OFF time without troublesome dyskinesia and/or without exacerbating a dyskinesia symptom in Parkinson's disease.

* * * * *